US012633375B2

(12) United States Patent
Mossman et al.

(10) Patent No.: US 12,633,375 B2
(45) Date of Patent: May 19, 2026

(54) METHODS OF PREDICTING DOPAMINE PRODUCTION CAPABILITY OF DIFFERENTIATED NEURONAL CELLS

(71) Applicant: Aspen Neuroscience, Inc., San Diego, CA (US)

(72) Inventors: Jim Mossman, San Diego, CA (US); Daniel Fremgen, San Diego, CA (US)

(73) Assignee: Aspen Neuroscience, Inc., San Diego, CA (US)

( * ) Notice: Subject to any disclaimer, the term of this patent is extended or adjusted under 35 U.S.C. 154(b) by 0 days.

(21) Appl. No.: 18/946,698

(22) Filed: Nov. 13, 2024

(65) Prior Publication Data

US 2025/0157580 A1      May 15, 2025

Related U.S. Application Data

(60) Provisional application No. 63/598,533, filed on Nov. 13, 2023.

(51) Int. Cl.
| | |
|---|---|
| *G16B 25/10* | (2019.01) |
| *C12Q 1/6881* | (2018.01) |
| *C12Q 1/6888* | (2018.01) |
| *G06N 20/00* | (2019.01) |
| *G16B 40/00* | (2019.01) |

(52) U.S. Cl.
CPC ........... *G16B 25/10* (2019.02); *C12Q 1/6881* (2013.01); *C12Q 1/6888* (2013.01); *G06N 20/00* (2019.01); *G16B 40/00* (2019.02); *C12Q 2600/158* (2013.01)

(58) Field of Classification Search
None
See application file for complete search history.

(56) References Cited

U.S. PATENT DOCUMENTS

| | | | |
|---|---|---|---|
| 2018/0258170 A1 | 9/2018 | Gholamin | |
| 2019/0211306 A1 | 7/2019 | Studer | |
| 2021/0093673 A1 | 4/2021 | Kim | |
| 2022/0254448 A1* | 8/2022 | Loring | G16B 25/10 |
| 2023/0059010 A1 | 2/2023 | Bratt-Leal | |

| | | |
|---|---|---|
| 2023/0377685 A1 | 11/2023 | Mossman |
| 2024/0219375 A1 | 7/2024 | Mcmahon |
| 2024/0417683 A1 | 12/2024 | Tastad |

FOREIGN PATENT DOCUMENTS

| | | | |
|---|---|---|---|
| KR | 2023-0165846 | * | 4/2020 |
| WO | 2019031595 | | 2/2019 |
| WO | 2021016607 | | 1/2021 |
| WO | 2021100829 | | 5/2021 |
| WO | 2022131322 | | 6/2022 |
| WO | 2023004371 | | 1/2023 |

OTHER PUBLICATIONS

Poulin et al. in Trends in Neuroscience (2020) vol. 43, No. 3:155-169.*
Yao et al. (Parkinson's Disease (2021) vol. 79:8 pages).*
Kirkeby Agnete et al, "Predictive Markers Guide Differentiation to Improve Graft Outcome in Clinical Translation of hESC-Based Therapy for Parkinson's Disease", Cell Stem Cell, Amsterdam, NL, (Jan. 1, 2017), vol. 20, No. 1, doi:10.1016/j.stem.2016.09.004, ISSN 1934-5909, pp. 135-148, XP055974965.
Written Opinion of the International Searching Authority, PCT2024/055715, Mar. 24, 2025.
International Search Report, PCT/US2024/055715, Mar. 24, 2025.
Ramirez et al. "Increased Expression of 1ncRNA AC000120.7 and SENP3-EIF4A1 in Patients with Acute Respiratory Distress Syndrome induced by SARS-CoV-2 Infection," Microorganisms 2023 11:2342, 11 pages.
Zhu et al., "Cuproptosis-related 1ncRNA signature for prognostic prediction in patients with acute myeloid leukemia," BMC Bioinformatics 2023 24:37, 17 pages.
Linsley et al., "Cell death assays for neurodegenerative disease drug discovery," Expert Opin Drug Discov. 2019 14:901-913.

* cited by examiner

*Primary Examiner* — Lori A. Clow

(74) *Attorney, Agent, or Firm* — Timothy L Smith

(57) ABSTRACT

Provided herein are methods for predicting characteristics, such as activity, function and/or differentiation state of an in vitro population of neuronal cells, for instance a population of neuronal progenitor cells, as well as methods for selecting and/or implanting an in vitro population of neuronal progenitor cells having desired characteristics. Also provided herein are computing devices for performing the provided methods as well as related compositions, articles of manufacture, and kits, including for use in methods of treating a subject having a neurodegenerative disease, for instance Parkinson's disease.

22 Claims, 16 Drawing Sheets

Figure 1:
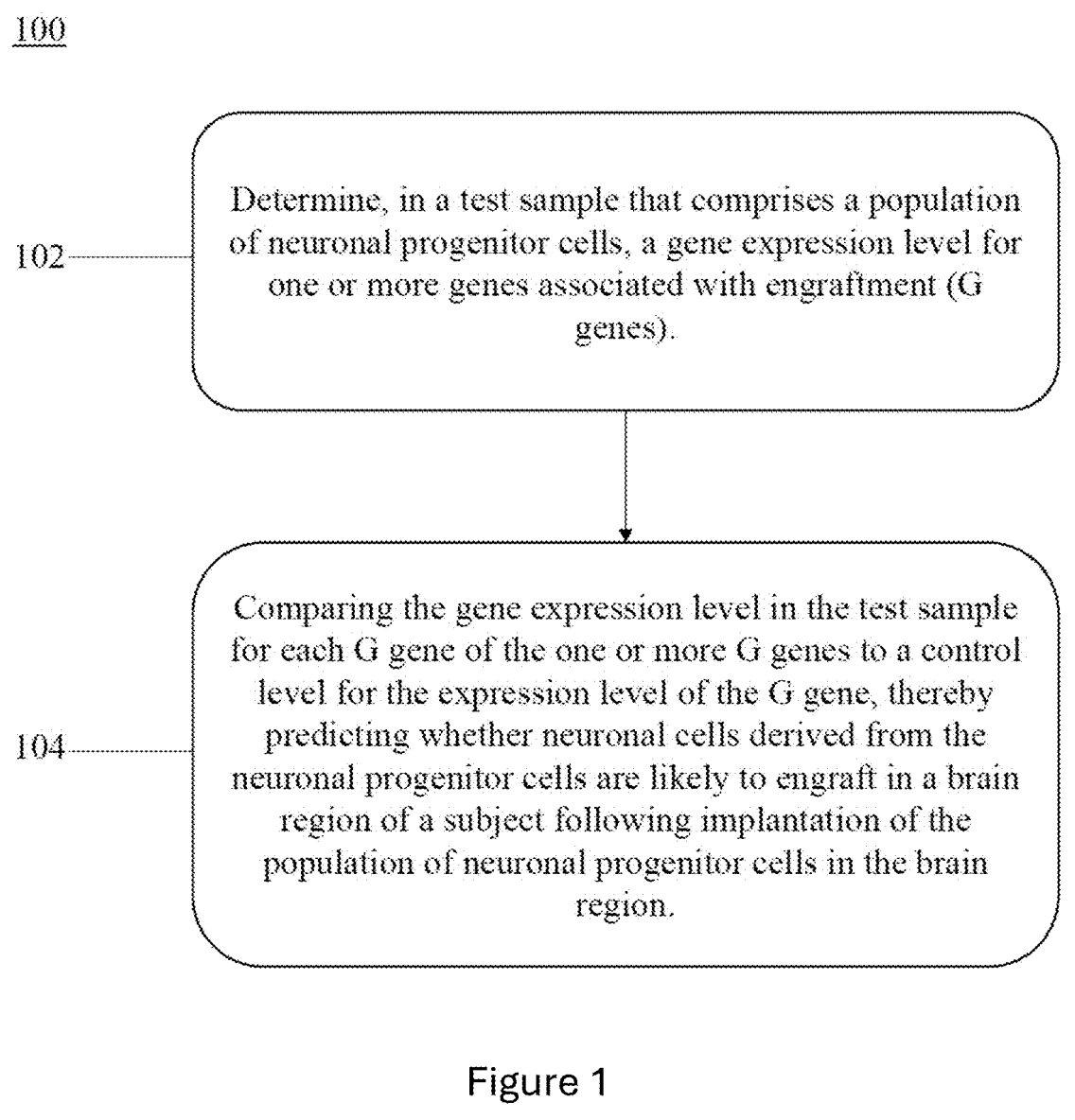

100

```
┌──────────────────────────────────────────────┐
│                                                │
│   Determine, in a test sample that comprises   │
│   a population of neuronal progenitor cells,    │
│   a gene expression level for one or more      │
│   genes associated with engraftment (G         │
│   genes).                                       │
│                                                │
└──────────────────────────────────────────────┘
```
102

```
┌──────────────────────────────────────────────┐
│                                                │
│   Comparing the gene expression level in the   │
│   test sample for each G gene of the one or    │
│   more G genes to a control level for the      │
│   expression level of the G gene, thereby      │
│   predicting whether neuronal cells derived    │
│   from the neuronal progenitor cells are       │
│   likely to engraft in a brain region of a     │
│   subject following implantation of the        │
│   population of neuronal progenitor cells in   │
│   the brain region.                             │
│                                                │
└──────────────────────────────────────────────┘
```
104

Figure 2:
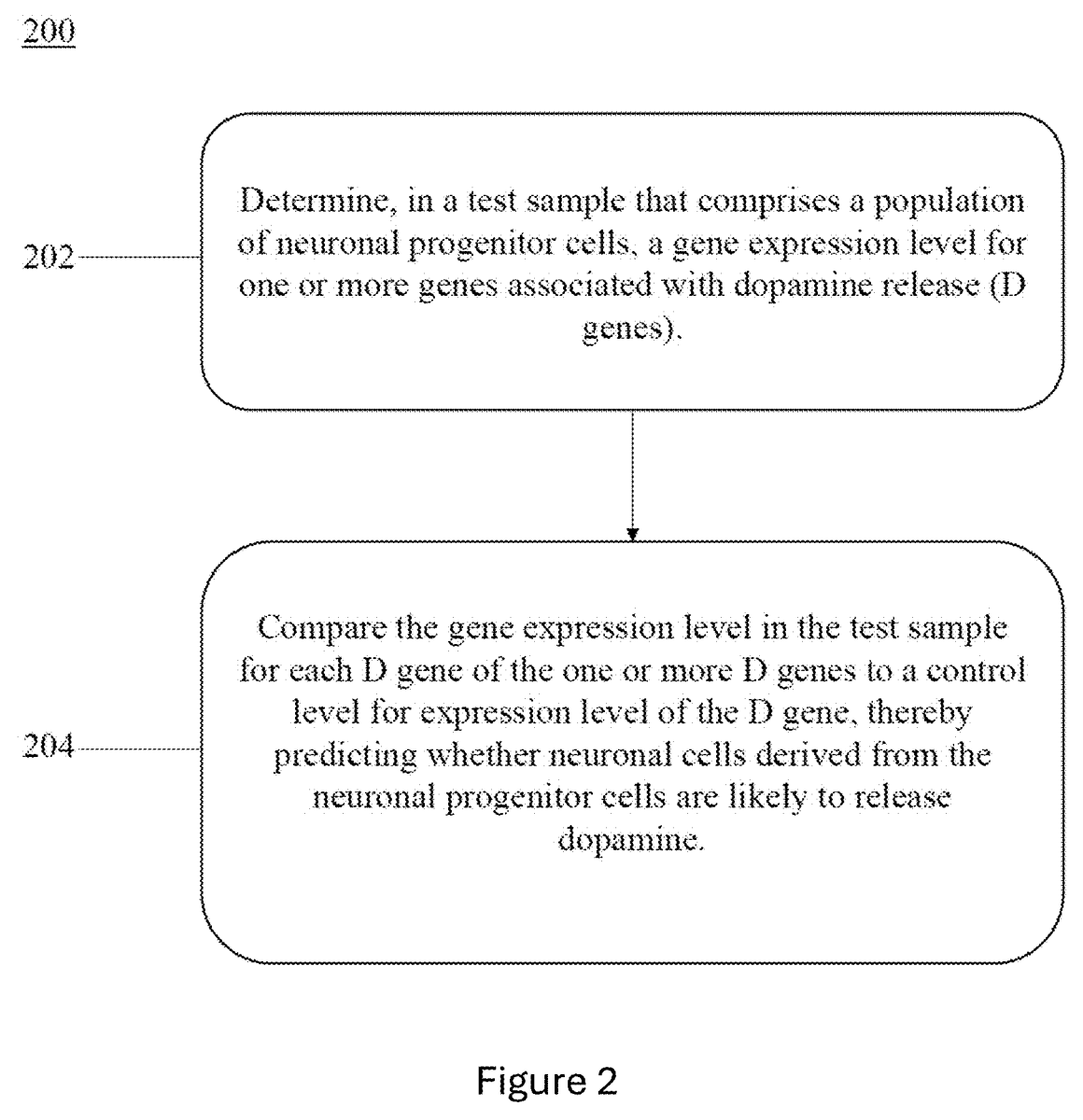

202 ——
> Determine, in a test sample that comprises a population of neuronal progenitor cells, a gene expression level for one or more genes associated with dopamine release (D genes).

204 ——
> Compare the gene expression level in the test sample for each D gene of the one or more D genes to a control level for expression level of the D gene, thereby predicting whether neuronal cells derived from the neuronal progenitor cells are likely to release dopamine.

PROCESSOR(S)

460

COMMUNICATION
DEVICE

420

INPUT
DEVICE

430

OUTPUT
DEVICE

440

MEMORY
STORAGE

450

SOFTWARE

470

DATA
STORAGE

480

System
500

Network 504

Communications
508

Communications
508

Communications
508

Device 400

Device 506

Figure 6

| Performance measure | PCA model Value |
|---|---|
| Accuracy | 0.8636 |
| AUC | 0.875 |
| $R^2$ | 0.7353 |
| Sensitivity | 0.9 |
| Specificity | 0.8333 |
| Precision | 0.8182 |
| Recall | 0.9 |
| F1 | 0.8571 |

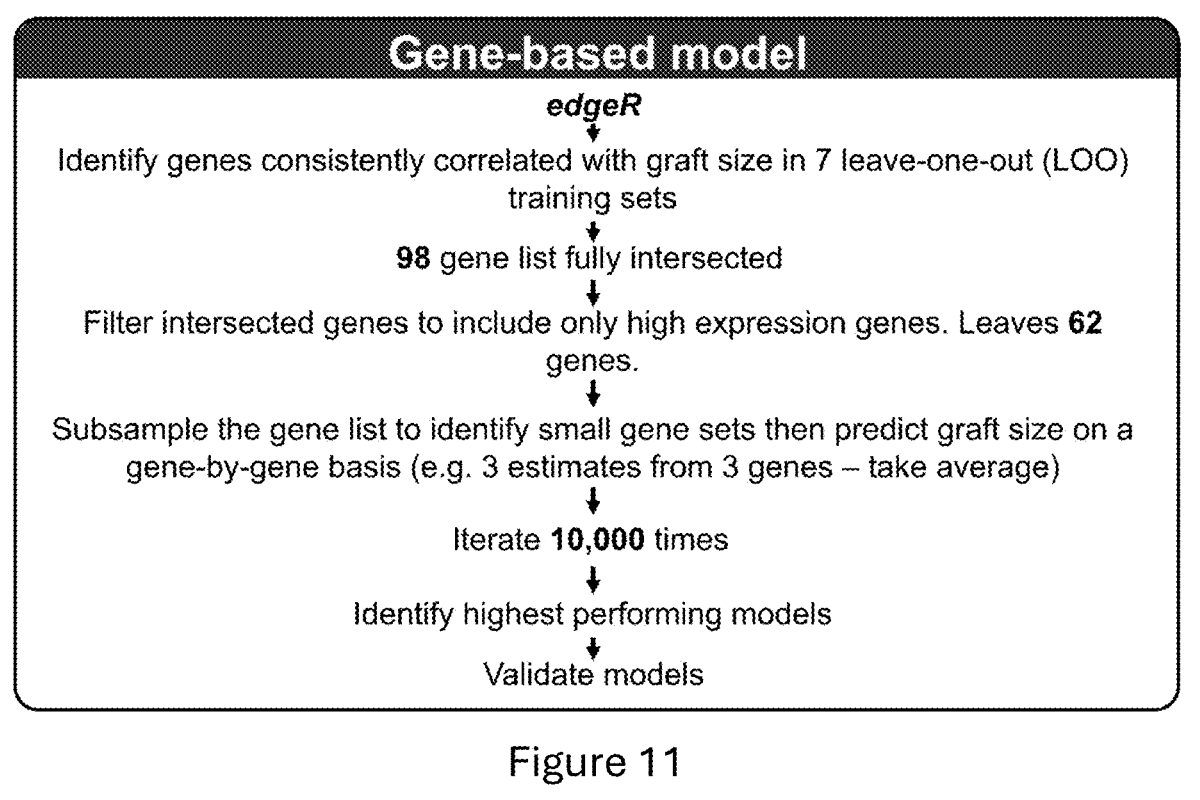

Gene-based model

*edgeR*

↓

Identify genes consistently correlated with graft size in 7 leave-one-out (LOO) training sets

↓

98 gene list fully intersected

↓

Filter intersected genes to include only high expression genes. Leaves 62 genes.

↓

Subsample the gene list to identify small gene sets then predict graft size on a gene-by-gene basis (e.g. 3 estimates from 3 genes – take average)

↓

Iterate 10,000 times

↓

Identify highest performing models

↓

Validate models

Figure 11

| Performance measure | 3-gene model Value |
|---|---|
| *Accuracy* | 0.8636 |
| *AUC* | 0.917 |
| *$R^2$* | 0.5278 |
| *Sensitivity* | 0.9 |
| *Specificity* | 0.8333 |
| *Precision* | 0.8182 |
| *Recall* | 0.9 |
| *F1* | 0.8571 |

Figure 14

Gene-Based Model

Nuclei in 21-day grafts

C

Performance Metrics      Model specifications

DA cut-off = 15      MinPC = 24.5
Sensitivity = 0.955      MaxPC = 34.5
Specificity = 0.957      MinR^2 = 0.45
Pos Predictive Value = 0.955      MaxR^2 = 0.55
Neg Predictive Value = 0.957      PCAs = 1000
Precision = 0.955
Recall = 0.955
F1 = 0.955
Prevalence = 0.489
Detection Rate = 0.467
Detection Prevalence = 0.489
Balanced Accuracy = 0.956
Accuracy = 0.956
Kappa = 0.911

METHODS OF PREDICTING DOPAMINE PRODUCTION CAPABILITY OF DIFFERENTIATED NEURONAL CELLS

CROSS-REFERENCE TO RELATED APPLICATIONS

This application claims priority to U.S. Provisional Application No. 63/598,533, filed Nov. 13, 2023, entitled "METHODS OF PREDICTING CHARACTERISTICS OF DIFFERENTIATED NEURONAL CELLS AND RELATED COMPOSITIONS OF DIFFERENTIATED CELLS," the contents of which are incorporated herein by reference in its entirety for all purposes.

FIELD

The present disclosure relates to methods for predicting characteristics, such as activity, function and/or differentiation state of an in vitro population of neuronal cells, for instance a population of neuronal progenitor cells, as well as methods for selecting and/or implanting an in vitro population of neuronal cells having desired characteristics. Also provided herein are computing devices for performing the provided methods as well as related compositions, articles of manufacture, and kits, including for use in methods of treating a subject having a neurodegenerative disease, for instance Parkinson's disease.

BACKGROUND

Parkinson's Disease leads to debilitating motor complications and currently no restorative treatments are available. Parkinson's disease trails only Alzheimer's disease as the most common neurodegenerative disorder, affecting about 0.3% of the general population and 1-2% of the population over age 65. The prevalence of PD is expected to double or triple as the developed world population ages. (Cha et al. (2023) *J. Mov. Disord.* 16:22-41; Rong et al. (2021) *Neurology* 97: e1986-e1993; Dorsey and Bloem (2018) *JAMA Neurol.* 75:9-10; de Lau and Breteler (2006) *Lancet Neurol.* 5:525-535).

Dopamine (DA) deficiency resulting from progressive loss of dopaminergic neurons in the substantia nigra is a common characteristic of PD. By the time of diagnosis, patients have already experienced significant nigrostriatal degeneration. Currently available treatments, such as dopamine replacement therapy (e.g., with L-dopa or dopamine agonists) benefit some patients, but have a limited therapeutic window due to side effects and decreasing efficacy. Cha et al., Weiss et al. (1971) *Lancet.* 1:1016-1017; Kang and Fahn (1988) *Ration. Drug Ther.* 22:1-7.

Cell replacement therapies that aim to restore lost dopamine producing neurons have been in development for many years. A challenge in developing a cell-based therapy for Parkinson's Disease (PD) has been the identification of an appropriate cell source for use in neuronal replacement. One approach was the transplantation of fetal midbrain DA neurons, such as was performed in over 300 patients worldwide. Brundin et al. (2010) *Prog. Brain Res.* 184:265-94; Lindvall, & Kokaia (2010) *J. Clin. Invest* 120:29-40. Therapy using human fetal tissue in these patients demonstrated evidence of DA neuron survival and in vivo DA release up to 10 or 20 years after transplantation in some patients. In many patients, though, fetal tissue transplantation fails to replace DA neuronal function. Moreover, Parkinson's disease patients who were treated with fetal cell transplants sometimes experience off-medication graft-induced dyskinesias. Evidence demonstrates that this serious side effect is caused by serotonin (5-HT) that is produced by the transplanted fetal cells. Politis et al. (2011) *Mov. Disord.* 26:1997-2003. Further, fetal tissue transplantation is plagued by challenges including low quantity and quality of donor tissue, ethical and practical issues surrounding tissue acquisition, and the poorly defined heterogeneous nature of transplanted cells, which are some of the other factors contributing to the variable clinical outcomes. Mendez et al. (2008) *Nature Med.* 14:507-509; Kordower et al. (1995) *N. Engl. J. Med.* 332:1118-24; and Piccini et al. (1999) *Nature Neuroscience* 2:1137-40. Hypotheses as to the limited efficacy observed in the human fetal grafting trials include that fetal grafting may not provide a sufficient number of cells at the correct developmental stage and that fetal tissue is quite poorly defined by cell type and variable with regard to the stage and quality of each tissue sample. Bjorklund et al. (2003) *Lancet Neurol.* 2:437-45. A further contributing factor may be inflammatory host response to the graft. Id.

Another approach is to use stem cell-derived cells, such as pluripotent stem cells (PSCs) as a source of cells for applications in regenerative medicine. Pluripotent stem cells can undergo self-renewal and give rise to all cells of the issues of the body. PSCs include two broad categories of cells: embryonic stem (ES) cells and induced pluripotent stem cells (iPSCs). ES cells are derived from the inner cell mass of preimplantation embryos and can be maintained indefinitely and expanded in their pluripotent state in vitro. Romito and Cobellis (2016) *Stem Cells Int.* 2016:9451492. Recently, preliminary results were reported for a phase I clinical trial that involved implanting dopaminergic neuronal cells obtained by differentiation of ES cells into the brains of patients with Parkinson's disease (2023 International Congress of Parkinson's Disease and Movement Disorders, held August 27-31 in Copenhagen, Denmark). The results showed that the strategy was well tolerated, with no serious adverse effects related to the treatment. Preliminary efficacy data indicated improvements in motor functions. Despite these advances, the use of embryonic stem cells is plagued by ethical concerns, as well as the possibility that such cells may form tumors in patients. Finally, ES cell-derived transplants may cause immune reactions in patients in the context of allogeneic stem cell transplant.

The use of induced pluripotent stem cells (iPSCs), rather than ES-derived cells, has the advantages of avoiding ethical concerns. Further, derivation of iPSCs from a patient to be treated (i.e., the patient receives an autologous cell transplant) avoids risks of immune rejection inherent in the use of embryonic stem cells. iPSCs can be obtained by reprogramming ("dedifferentiating") adult somatic cells to become more ES cell-like, including having the ability to expand indefinitely and differentiate into all three germ layers. Id. Such reprogramming is often accomplished using the "Yamanaka factors. (Oct 3/4, Sox2, Klf4, and a Myc family member). See, e.g., U.S. Pat. No. 8,530,238.

Various methods for differentiating pluripotent stem cells into lineage specific cell populations and the resulting cellular compositions are contemplated to find use in cell replacement therapies for patients with diseases resulting in a loss of function of a defined cell population. However, in some cases, such methods are limited in their ability to produce cells with consistent physiological characteristics, and cells resulting from such methods may be limited in their ability to engraft and innervate other cells in vivo. As an example, neural cells obtained by differentiation from pluripotent stem cells may be more amenable to engraftment into the brain of a subject undergoing treatment when the neural cells are at an intermediate stage between earlier stages (e.g., that of precursor or progenitor cells) and later stages (e.g., that of differentiated cells). Moreover, there is a need for improving the manufacturability of lineage-specific cell populations, e.g., for therapeutic purposes, that are derived from pluripotent stem cells, such as by reducing the time and/or resources, including cost, required for such manufacturing.

While many differentiation protocols can generate cells expressing dopaminergic markers, identifying such cells that are suitable for implantation into a subject remains a challenge. For example, it is desirable that the cells successfully engraft into the subject's brain after implantation, and that the cells will produce dopamine after implantation and engraftment. In some cases, regulatory agencies such as the US Food and Drug Administration (FDA) in the United States and the European Medicines Agency (the EMEA) in Europe require that cell therapy products have a potency test for licensure. The FDA, for example, and states that potency tests should be based on the product's mechanism of action (MOA) (Draft Guidance for Industry—Potency Assurance for Cellular and Gene Therapy Products, US Food and Drug Administration (December 2023), available on the FDA website under regulatory guidance documents. For cell therapies that have a complex spectrum of mechanisms, it is desirable to have a potency assay matrix that can quantitatively and accurately characterize the various important functions of the cells after they have matured.

Accordingly, a need exists for methods to assess the potency of neuronal progenitor cells such as those obtained by differentiation of stem cells for use in treating neurodegenerative diseases. Among such potency measures that are needed are ways to predict whether a population of neuronal progenitor cells is likely to engraft successfully after implantation into a brain of a subject, and also to predict whether neuronal cells that are differentiated from a population of neuronal progenitor cells are likely to produce dopamine. The present invention fulfils these and other needs.

SUMMARY OF THE INVENTION

The present invention provides, in some embodiments, methods for predicting whether a population of neuronal progenitor cells are likely to successfully engraft when implanted into a brain region. These methods can include, in some embodiments: (a) determining a gene expression level for one or more genes associated with predicted engraftment potential (G genes) in a test sample that includes a population of neuronal progenitor cells, wherein the one or more G genes are selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; and (b) predicting the neuronal engraftment capability of the neuronal progenitor cells by correlating the determined gene expression level of the one or more G genes in the test sample with a reference plot for each G gene that associates graft size with gene expression levels of the G gene in a training set that comprises one or more reference samples. In some embodiments, the one or more G genes are selected from the group consisting of TTR, PRR16, CMTM8, APOA1, CD47, CDO1, KIR26A and CNTN2. In some embodiments, the one or more G genes are selected from the group consisting of TTR, PRR16, and CD47. In some embodiments, the one or more G genes are TTR, PRR16, and CD47. In some embodiments, the expression levels are determined for at least 2, 3, 4, 5, 6, 7, 8, 9, 10, 11, 12, 13, 14, 15, 16, 17, 18, 19 or 20 of the G genes.

In some embodiments, the reference plot includes one or more data points, wherein each data point on the reference plot is determined by: (a) measuring the gene expression level of the G gene in a reference sample that comprises a population of neuronal progenitor cells; (b) implanting neuronal progenitor cells from the reference sample of into a brain region of a test animal and measuring the size of a graft formed by the implanted neuronal progenitor cells after an incubation period; and (c) plotting the graft size against the expression level of the G gene to obtain a data point for the training sample. In some embodiments, the reference plot includes a plurality of data points that are obtained for each of a plurality of reference samples. In some embodiments, the reference plot is obtained by differential expression analysis or linear regression analysis of the plurality of datapoints.

In some embodiments, the methods for predicting whether a population of neuronal progenitor cells are likely to successfully engraft when implanted into a brain region involve obtaining the reference plot by applying the gene expression levels of the one or more G genes in the test sample as input to a machine learning model configured to predict whether neuronal cells derived from the neuronal progenitor cells are likely to engraft in a brain region of a subject following implantation of the population of neuronal progenitor cells into the brain region, wherein the machine learning model is trained using gene expression levels of the G genes in a plurality of reference populations of neuronal progenitor cells. In some embodiments, the machine learning includes principal component analysis.

In some embodiments, the predicted graft size is expressed as a number of neuronal cells derived from the neuronal progenitor cells within a cross section of the brain region of the test animal. In some embodiments, the brain region is the substantia nigra, and in some embodiments, the cross section of the substantia nigra includes approximately one sixth of the substantia nigra. In some embodiments, a high engraftment capability is indicated if the predicted graft size is greater than 1,000 cells in the one sixth cross section of the substantia nigra.

In some embodiments, the predicted engraftment capability is determined for two or more G genes and an overall engraftment capability prediction for the test sample is based on a combined assessment of the predicted engraftment capabilities for each of the two or more G genes. In some embodiments the combined assessment comprises determining a mean or median predicted engraftment capability for each of the two or more G genes.

In some embodiments, the population of neuronal progenitor cells is from a culture of cells differentiated from pluripotent stem cells under conditions to neurally differentiate the cells. In some embodiments, the pluripotent stem cells are induced pluripotent stem cells (iPSCs). In some embodiments, the pluripotent stem cells are autologous to the subject to which the neuronal progenitor cells are implanted. In some embodiments, the differentiation conditions comprise adherent cell culture and the test sample of neuronal progenitor cells is obtained between day 18 and day 24 after initiation of the differentiation process. In some embodiments, the differentiation conditions comprise suspension cell culture and the test sample of neuronal progenitor cells is obtained between day 13 and day 20 after initiation of the differentiation process. In some embodiments, the test sample of neuronal progenitor cells is obtained on about day 16 after initiation of the differentiation process. In some embodiments, the reference sample includes a pooled sample of neuronal progenitor cells derived from multiple donors.

In some embodiments, the gene expression level of each of the at least one G gene is determined by RNA sequencing (RNAseq). In some embodiments, the gene expression level of each of the at least one G gene is determined by polymerase chain reaction (PCR), and in some embodiments the PCR is quantitative PCR (qPCR). In some embodiments, the gene expression level of the one or more G gene is determined by: (a) obtaining an RNA sample from the test sample of neuronal progenitor cells; (b) synthesizing complementary DNA from the RNA sample using reverse transcription; (c) amplifying a specific nucleic acid fragment corresponding to the G gene using quantitative polymerase chain reaction (qPCR), wherein the qPCR comprises the use of a pair of primers specific to the G gene, and optionally a probe specific to the G gene; and (d) determining the expression level of the G gene based on the normalized quantified amount.

In some embodiments, the gene expression level of the one or more G genes is normalized as a ratio of the relative expression level of the G gene to a housekeeping gene. An example of a suitable housekeeping gene is GAPDH.

In some embodiments, the invention provides methods for predicting neuronal engraftment capability of neuronal cells derived from a test population of neuronal progenitor cells after implantation of the neuronal progenitor cells into a brain that include: (a) determining a gene expression level for one or more genes associated with engraftment (G genes) in a test sample that includes a population of neuronal progenitor cells, wherein the one or more G genes are selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; and (b) comparing the expression level of each of the one or more G genes in the test population of neuronal progenitor cells to a predetermined threshold value for the particular G gene, wherein high engraftment capability of the neuronal progenitor cells is indicated if the expression level is either: (i) above the predetermined threshold value for that G gene; or (ii) below the predetermined threshold value for that G gene, wherein "above" or "below" is defined by the known biological relevance of the G gene in the context of engraftment capability.

In some embodiments, the predetermined threshold value for the particular G gene is based on the expression level of the G gene in a training sample that includes neuronal progenitor cells that are known to exhibit high engraftment levels when implanted into a brain, and a gene expression level for the G gene in the test sample that is similar to the expression level of the G gene in the training sample is predictive of high engraftment potential for neuronal cells derived from the neuronal progenitor cells in the test sample.

In some embodiments, the predetermined threshold value for the particular G gene is based on the expression level of the G gene in a training sample that includes neuronal progenitor cells that are known to exhibit low engraftment levels when implanted into a brain, and a gene expression level for the G gene in the test sample that is similar to the expression level of the G gene in the control sample is predictive of low engraftment potential for neuronal cells derived from the neuronal progenitor cells in the test sample.

In some embodiments, the neuronal progenitor cells are predicted to have high engraftment capability after implantation into the brain if: (a) the gene expression level of at least one first G gene selected from the group consisting of AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2 is lower than the predetermined threshold value for the first G gene; and/or (b) the gene expression level of at least one second G gene selected from the group consisting of DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2 is higher than the predetermined threshold value for the second G gene.

In some embodiments, the predetermined threshold value for the particular G gene is based on a ratio of the relative expression levels in the test sample of a) the G gene, and b) a control gene. In some embodiments, the control gene is GAPDH and the predetermined threshold value is selected from the group consisting of: (a) a ratio of AC000120.3 to GAPDH expression of less than about 0.14; (b) a ratio of KRT77 to GAPDH expression of less than about 0.68; (c) a ratio of TTR to GAPDH expression of less than about 1.11; (d) a ratio of PRR16 to GAPDH expression of less than about 0.43; (e) a ratio of MEGF10 to GAPDH expression of less than about 0.79; (f) a ratio of PDE3A to GAPDH expression of less than about 1.00; (g) a ratio of GDPD2 to GAPDH expression of less than about 0.78; (h) a ratio of CMTM8 to GAPDH expression of less than about 1.02; (i) a ratio of APOA1 to GAPDH expression of less than about 0.68; (j) a ratio of CMTM7 to GAPDH expression of less than about 0.88; (k) a ratio of CDHR3 to GAPDH expression of less than about 1.09; (1) a ratio of CORIN to GAPDH expression of less than about 1.24; (m) a ratio of VTN to GAPDH expression of less than about 0.98; (n) a ratio of CPNE8 to GAPDH expression of less than about 0.79; (o) a ratio of EFEMP1 to GAPDH expression of less than about 0.83; (p) a ratio of CD47 to GAPDH expression of less than about 1.16; (q) a ratio of SPARC to GAPDH expression of less than about 1.29; (r) a ratio of JAM2 to GAPDH expression of less than about 0.82; (s) a ratio of CDO1 to GAPDH expression of less than about 1.00; (t) a ratio of PLXDC2 to GAPDH expression of less than about 1.00; (u) a ratio of DYNLL2 to GAPDH expression of greater than about 0.56; (v) a ratio of ITGA3 to GAPDH expression of greater than about 0.26; (w) a ratio of RPS6KL1 to GAPDH expression of greater than about 0.21; (x) a ratio of CHRNB2 to GAPDH expression of greater than about 0.23; (y) a ratio of SULT4A1 to GAPDH expression of greater than about 0.22; (z) a ratio of PTPN3 to GAPDH expression of greater than about 0.03; (aa) a ratio of LZTS1 to GAPDH expression of greater than about 0.19; (ab) a ratio of RUNX1T1 to GAPDH expression of greater than about 0.24; (ac) a ratio of TMEM145 to GAPDH expression of greater than about 0.05; (ad) a ratio of EPHA10 to GAPDH expression of greater than about 0.16; (ae) a ratio of CAR-MIL3 to GAPDH expression of greater than about 0.16; (af) a ratio of MANEAL to GAPDH expression of greater than about 0.24; (ag) a ratio of TMEM176B to GAPDH expression of greater than about 0.11; (ah) a ratio of MPP3 to GAPDH expression of greater than about 0.12; (ai) a ratio of DRAXIN to GAPDH expression of greater than about 0.27; (aj) a ratio of ADGRB1 to GAPDH expression of greater than about 0.07; (ak) a ratio of KIF26A to GAPDH expression of greater than about 0.23; (al) a ratio of CELF5 to GAPDH expression of greater than about 0.25; (am) a ratio of CNTN2 to GAPDH expression of greater than about 0.23; (an) a ratio of ASPHD1 to GAPDH expression of greater than about 0.08; (ao) a ratio of SVOP to GAPDH expression of greater than about 0.16; (ap) a ratio of ANGPT2 to GAPDH expression of greater than about 0.06; (aq) a ratio of SLC22A15 to GAPDH expression of greater than about 0.04; (ar) a ratio of SRRM3 to GAPDH expression of greater than about 0.17; (as) a ratio of GRIN2D to GAPDH expression of greater than about 0.02; (at) a ratio of DACH2 to GAPDH expression of greater than about 0.06; (au) a ratio of CHST1 to GAPDH expression of greater than about 0.04; (av) a ratio of GRIN1 to GAPDH expression of greater than about 0.26; (aw) a ratio of LHX5 to GAPDH expression of greater than about 0.06; and (ax) a ratio of NOS2 to GAPDH expression of greater than about 0.08.

The invention also provides, in some embodiments, methods for training a machine learning model for predicting whether a population of neuronal progenitor cells are likely to successfully engraft when implanted into a brain region. These methods can include: (a) obtaining gene expression levels for one or more genes in each of a plurality of reference populations of neuronal progenitor cells; (b) receiving engraftment fitness information for each of the plurality of reference populations, wherein the engraftment fitness information of a reference population indicates whether or not, or the degree to which, neuronal progenitor cells of the reference population engrafted in a brain region of a subject following implantation of the neuronal progenitor cells into the brain region; and (c) applying the gene expression levels of (a) and applying the engraftment fitness information of (b) as input to train a machine learning model, wherein the machine learning model is trained to predict based on the gene expression levels of the plurality of genes if a population of neuronal progenitor cells will engraft in a brain region of a subject following implantation of the population of neuronal progenitor cells into the brain region.

In some embodiments, the invention provides computing device configured to predict the engraftment potential of a population of neuronal progenitor cells when the neuronal progenitor cells are implanted into a brain region, the computing device comprising: (a) a processor; (b) a memory comprising instructions executable by the processor, the instructions configured to execute the steps of: (i) receiving a test sample that includes gene expression data for one or more genes associated with predicted engraftment potential (G genes) in a population of neuronal progenitor cells, wherein the one or more G genes are selected from the group consisting of AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; (ii) determining, based on the test sample, a gene expression level for each of the one or more G genes; (iii) comparing the determined gene expression level for each of the one or more G genes in the test sample to a reference plot for each respective G gene, wherein each reference plot correlates gene expression levels of the G gene with graft size data obtained from a training set comprising one or more reference samples; and (iv) predicting the neuronal engraftment capability of the neuronal progenitor cells in the test sample by correlating the determined gene expression levels of the one or more G genes in the test sample with the reference plot data, thereby generating a predictive assessment of engraftment potential for the population of neuronal progenitor cells.

Also provided by the invention, in some embodiments, are kits for predicting engraftment potential of neuronal cells derived from neuronal progenitor cells. Such kits can include one or more of: (a) a first pair of oligonucleotide primers suitable for amplification of a first gene; (b) a second pair of oligonucleotide primers suitable for amplification of a second gene and; (c) a third pair of oligonucleotide primers suitable for amplification of a third gene; wherein each of the first gene, the second gene, and the third gene is selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2 (G Genes). In some embodiments, the first gene, the second gene, and the third gene are each selected from the group consisting of: TTR, PRR16, CMTM8, APOA1, CD47, CD01, KIR26A and CNTN2. In some embodiments, kit comprises at least three pairs of oligonucleotide primers and the first gene is TTR, the second gene is PRR16, and the third gene is CD47. In some embodiments, the expression levels are determined for at least 2, 3, 4, 5, 6, 7, 8, 9, 10, 11, 12, 13, 14, 15, 16, 17, 18, 19 or 20 of the G genes. In some embodiments, reference sample includes a pooled sample of neuronal progenitor cells derived from multiple donors In some embodiments, the invention provides methods for predicting whether neuronal cells derived from a population of neuronal progenitor cells will produce dopamine. These methods involve, in some embodiment: (a) determining a gene expression level for one or more gene associated with predicted dopamine production (D genes) in a test sample that comprises a population of neuronal progenitor cells, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; and (b) predicting the dopamine production capability of neuronal cells derived from the neuronal progenitor cells by correlating the determined gene expression level of the one or more D genes in the test sample with a reference plot for each D gene that associates dopamine production by the neuronal cells with gene expression levels of the D gene in a training set that includes one or more reference samples. In some embodiments, the one or more D genes are selected from the group consisting of CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the one or more D genes are selected from the group consisting of B3GALT5, FRMPD3, and GREM2. In some embodiments, the one or more D genes are B3GALT5, FRMPD3 and GREM2.

In some embodiments, each data point on the reference plot is determined by: (a) measuring the gene expression level of the D gene in a reference sample that includes a population of neuronal progenitor cells; (b) differentiating the neuronal progenitor cells to produce neuronal cells and measuring the amount of dopamine produced by neuronal cells derived from the neuronal progenitor cells; and (c) plotting the dopamine production against the expression level of the D gene to obtain a data point for the training sample. In some embodiments, the reference plot includes a plurality of data points that are obtained for each of a plurality of reference samples. In some embodiments, the reference plot is obtained by differential expression analysis or linear regression analysis of the plurality of data points.

In some embodiments, the reference plot is obtained by applying the gene expression levels of the one or more D genes in the test sample as input to a machine learning model configured to predict whether neuronal cells derived from a population of neuronal progenitor cells will produce dopamine, wherein the machine learning model is trained using gene expression levels of the D genes in a plurality of reference populations of neuronal progenitor cells. In some embodiments the machine learning model includes principal component analysis.

In some embodiments, the population of neuronal progenitor cells is predicted to have a high dopamine production capability if the predicted amount of dopamine produced by the neuronal cells derived from the neuronal progenitor cells is at least 15 nM dopamine per $10^5$ neuronal cells.

In some embodiments, the predicted dopamine production capability is determined for two or more D genes and an overall dopamine production capability prediction for the test sample is based on a combined assessment of the predicted dopamine production capabilities for each of the two or more D genes. In some embodiments, the combined assessment includes determining a mean or median predicted engraftment capability.

In some embodiments, the invention provides methods for predicting whether neuronal cells derived from a population of neuronal progenitor cells will produce dopamine that include: (a) determining a gene expression level for one or more genes associated with predicted dopamine production capability (D genes) in a test sample that comprises a population of neuronal progenitor cells, wherein the one or more D genes are selected from the group consisting of: CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; and (b) comparing the expression level of each of the one or more D genes in the test population of neuronal progenitor cells to a predetermined threshold value for the particular D gene. High predicted dopamine production capability of the neuronal progenitor cells is indicated if the expression level is either: (i) above the predetermined threshold value for that D gene; or (ii) below the predetermined threshold value for that D gene; wherein "above" or "below" is defined by the known biological relevance of the D gene in the context of predicted dopamine production capability.

In some embodiments, the predetermined threshold value for the particular D gene is based on the expression level of the D gene in a training sample that comprises neuronal progenitor cells that are known to produce neuronal cells that produce high levels of dopamine, and a gene expression level for the D gene in the test sample that is similar to the expression level of the D gene in the training sample is predictive of high dopamine production potential for neuronal cells derived from the neuronal progenitor cells in the test sample. In some embodiments, wherein the predetermined threshold value for the particular D gene is based on the expression level of the D gene in a training sample that comprises neuronal progenitor cells that are known to produce neuronal cells that produce low levels of dopamine, and a gene expression level for the D gene in the test sample that is similar to the expression level of the D gene in the control sample is predictive of low dopamine production potential for neuronal cells derived from the neuronal progenitor cells in the test sample.

In some embodiments, the neuronal progenitor cells are predicted to produce neuronal cells that have a high dopamine production capability if: (a) the gene expression level of at least one first D gene selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1 and ZHX1 is lower than the predetermined threshold value for the first D gene; and/or (b) the gene expression level of at least one second D gene selected from the group consisting of BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1 is higher than the predetermined threshold value for the second D gene.

In some embodiments, the predetermined threshold value for the particular D gene is based on a ratio of the relative expression levels in the test sample of a) the D gene, and b) a control gene. In some embodiments, the control gene is GAPDH and the predetermined threshold value is selected from the group consisting of: (a) a ratio of CNTNAP5 to GAPDH expression of less than about 0.12; (b) a ratio of KLHL1 to GAPDH expression of less than about 0.10; (c) a ratio of NHLH2 to GAPDH expression of less than about 0.56; (d) a ratio of GREM2 to GAPDH expression of less than about 0.35; (e) a ratio of BRINP2 to GAPDH expression of less than about 0.97; (f) a ratio of GRIN3A to GAPDH expression of less than about 0.48; (g) a ratio of LRRC4C to GAPDH expression of less than about 0.39; (h) a ratio of IRX3 to GAPDH expression of less than about 0.55; (i) a ratio of CPNE4 to GAPDH expression of less than about 0.28; (j) a ratio of PTPN3 to GAPDH expression of less than about 0.25; (k) a ratio of PMEL to GAPDH expression of less than about 0.29; (l) a ratio of PCDH20 to GAPDH expression of less than about 0.20; (m) a ratio of LRRC37A2 to GAPDH expression of less than about 0.68; (n) a ratio of TMEM246 to GAPDH expression of less than about 0.53; (o) a ratio of B3GALNT1 to GAPDH expression of less than about 0.67; (p) a ratio of ZHX1 to GAPDH expression of less than about 0.55; (q) a ratio of BCAS4 to GAPDH expression of greater than about 0.42; (r) a ratio of SLC25A37 to GAPDH expression of greater than about 0.38; (s) a ratio of GRINA to GAPDH expression of greater than about 0.60; (t) a ratio of MID1 to GAPDH expression of greater than about 0.62; (u) a ratio of FRMD4A to GAPDH expression of greater than about 0.57; (v) a ratio of PARP10 to GAPDH expression of greater than about 0.25; (w) a ratio of WHAMMP2 to GAPDH expression of greater than about 0.37; (x) a ratio of EYA1 to GAPDH expression of greater than about 0.32; (y) a ratio of CORO2B to GAPDH expression of greater than about 0.40; (z) a ratio of WHAMMP3 to GAPDH expression of greater than about 0.34; (aa) a ratio of B3GALT5 to GAPDH expression of greater than about 0.40; (ab) a ratio of GPR35 to GAPDH expression of greater than about 0.19; (ac) a ratio of ABCD2 to GAPDH expression of greater than about 0.35; (ad) a ratio of ITIH3 to GAPDH expression of greater than about 0.17; (ae) a ratio of AC107464.1 to GAPDH expression of greater than about 0.20; (af) a ratio of CAMK2N1 to GAPDH expression of greater than about 0.52; (ag) a ratio of CAMK2A to GAPDH expression of greater than about 0.37; (ah) a ratio of PRPS1 to GAPDH expression of greater than about 0.52; (ai) a ratio of GOLGA6L10 to GAPDH expression of greater than about 0.21; (aj) a ratio of AMOT to GAPDH expression of greater than about 0.50; (ak) a ratio of SULT1A1 to GAPDH expression of greater than about 0.18; (al) a ratio of CD83 to GAPDH expression of greater than about 0.29; (am) a ratio of SPON1 to GAPDH expression of greater than about 0.76; (an) a ratio of FRMPD3 to GAPDH expression of greater than about 0.31; (ao) a ratio of AC096570.1 to GAPDH expression of greater than about 0.14; (ap) a ratio of TCAF2 to GAPDH expression of greater than about 0.30; (aq) a ratio of GOLGA8M to GAPDH expression of greater than about 0.003; (ar) a ratio of VWA5B2 to GAPDH expression of greater than about 0.22; (as) a ratio of CA8 to GAPDH expression of greater than about 0.19; (at) a ratio of AC017050.1 to GAPDH expression of greater than about 0.08; (au) a ratio of KRT77 to GAPDH expression of greater than about 0.14; (av) a ratio of AP000350.6 to GAPDH expression of greater than about 0.31; (aw) a ratio of LINC02751 to GAPDH expression of greater than about 0.19; and (ax) a ratio of ARHGAP5-AS1 to GAPDH expression of greater than about 0.26.

In some embodiments, the invention provides methods of training a machine learning model for predicting whether neuronal cells derived from a population of neuronal progenitor cells will produce dopamine. These methods can include: (a) obtaining gene expression levels for one or more genes in each of a plurality of reference populations of neuronal progenitor cells; (b) receiving dopamine production information for neuronal cells derived from each of the plurality of reference populations, wherein the dopamine production information of a reference population indicates whether or not, or the degree to which, cells derived from the neuronal progenitor cells produced dopamine; and (c) applying the gene expression levels of (a) and applying the dopamine production information of (b) as input to train a machine learning model, wherein the machine learning model is trained to predict based on the gene expression levels of the plurality of genes if neuronal cells derived from a population of neuronal progenitor cells will produce dopamine.

In some embodiments, the invention provides kits for predicting dopamine production by neuronal cells derived from a population of neuronal progenitor cells. The kits of the invention include one or more of: (a) a first pair of oligonucleotide primers suitable for amplification of a first gene; (b) a second pair of oligonucleotide primers suitable for amplification of a second gene and (c) a third pair of oligonucleotide primers suitable for amplification of a third gene; wherein each of the first gene, the second gene, and the third gene is selected from the group consisting of: CNT-NAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1. In some embodiments, the first gene, the second gene, and the third gene are each selected from the group consisting of CNT-NAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the first gene is B3GALT5, the second gene is GREM2, and the third gene is FRMPD3.

In some embodiments, the invention provides a computing device configured to predict whether neuronal cells differentiated from a population of neuronal progenitor cells will produce dopamine. The computing device includes: (a) a processor; (b) a memory comprising instructions executable by the processor, the instructions configured to execute the steps of: (i) receiving a test sample that includes gene expression data for one or more genes associated with predicted dopamine production potential (D genes) in a population of neuronal progenitor cells, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; (ii) determining, based on the test sample, a gene expression level for each of the one or more D genes; (iii) comparing the determined gene expression level for each of the one or more D genes in the test sample to a reference plot for each respective D gene, wherein each reference plot correlates gene expression levels of the D gene with dopamine production levels obtained from a training set comprising one or more reference samples; and (iv) predicting the dopamine production capability of neuronal cells derived from the neuronal progenitor cells in the test sample by correlating the determined gene expression levels of the one or more D genes with the reference plot data, thereby generating a predictive assessment of dopamine production potential for the derived neuronal cells.

In some embodiments, the invention provides a potency assay matrix for determining the potency of a population of neuronal progenitor cells for treatment of a neurodegenerative disease. The potency assay matrix includes subjecting the population of neuronal progenitor cells to a method that includes at least two of the following steps (a), (b) and (c):

(a) classifying an in vitro population of neuronal progenitor cells to determine whether the neural progenitor cells comprise determined dopaminergic precursor cells by: (i) receiving as input a test dataset that comprises expression levels for one or more genes that are expressed in a first test sample that comprises the neuronal progenitor cells; (ii) calculating a first similarity score for the first test sample using the test dataset and a first reference dataset, wherein: (1) the first reference dataset comprises a representation of gene expression levels for one or more genes that are differentially expressed between cells at a first differentiation state and cells at a second differentiation state, wherein the second differentiation state is that of a determined dopaminergic neuronal cell, and wherein the first differentiation state is earlier or later in a stem cell differentiation pathway than the second differentiation state; (2) the expression levels in the test dataset comprise expression levels for one or more of the genes for which a representation of expression levels are included in the first reference dataset, and (3) the first similarity score indicates whether the differentiation state of the test cells is more similar to the first differentiation state or to the second differentiation state; (iii) determining a novelty score for the neuronal progenitor cells in the first test sample, wherein the novelty score indicates the degree to which the gene expression levels in the test dataset deviate from gene expression levels in the reference database; and (iv) determining, based on the similarity score and the novelty score, whether the first test sample comprises determined dopaminergic neuronal cells;

(b) predicting whether the neuronal progenitor cells are likely to successfully engraft when implanted into a brain region by: (i) determining a gene expression level for one or more genes associated with predicted engraftment potential (G genes) in a second test sample that comprises the neuronal progenitor cells, wherein the one or more G genes are selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; and (ii) predicting the neuronal engraftment capability of the neuronal progenitor cells by correlating the determined gene expression level of the one or more G genes in the second test sample with a reference plot for each G gene that associates graft size with gene expression levels of the G gene in a training set that comprises one or more reference samples; and (c) predicting whether neuronal cells derived from the population of neuronal progenitor cells will produce dopamine by: (i) determining a gene expression level for one or more gene associated with predicted dopamine production (D genes) in a third test sample that comprises a population of neuronal progenitor cells, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; and (ii) predicting the dopamine production capability of neuronal cells derived from the neuronal progenitor cells by correlating the determined gene expression level of the one or more D genes in the third test sample with a reference plot for each D gene that associates dopamine production by the neuronal cells with gene expression levels of the D gene in a training set that comprises one or more reference samples of neuronal progenitor cells.

In some embodiments, the potency assay matrix includes steps (a) and (b). In some embodiments, the potency assay matrix includes steps (b) and (c). In some embodiments, the potency assay matrix includes steps (a) and (c). In some embodiments, the potency assay matrix includes all three of steps (a), (b) and (c).

In some embodiments, the potency assay matrix includes step (b) and the G genes are selected from the group consisting of TTR, PRR16, CMTM8, APOA1, CD47, CD01, KIR26A and CNTN2. In some embodiments, the one or more G genes are TTR, PRR16 and CD47.

In some embodiments, the potency assay matrix includes step (c) and the one or more D genes is selected from the group consisting of CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the one or more D genes are B3GALT5, FRMPD3, and GREM2.

Also provided herein is a therapeutic composition comprising a population of neuronal progenitor cells selected by any of the methods disclosed therein.

Also provided herein is a therapeutic composition that contains neuronal progenitor cells derived from pluripotent stem cells, wherein the therapeutic composition includes neuronal progenitor cells from at least two populations selected from the group consisting of: (a) a first population of neuronal progenitor cells that are classified as determined dopaminergic precursor cells using a method that comprises classifying the neuronal progenitor cells based on a probability score and a deviation score; (b) a second population of neuronal progenitor cells that are predicted to produce neuronal cells that have high engraftment potential; and (c) a third population of neuronal progenitor cells that are predicted to produce neuronal cells that have high dopamine production.

In some embodiments, the therapeutic composition comprises a pharmaceutically acceptable carrier.

In some embodiments, the therapeutic composition comprises a cryoprotectant.

In some embodiments, the cryoprotectant is selected from among the group consisting of glycerol, propylene glycol, and dimethyl sulfoxide (DMSO).

In some embodiments, the composition is for use in treatment of a neurodegenerative disease or condition in a subject, optionally wherein the neurodegenerative disease or condition comprises a loss of dopaminergic neurons.

In some embodiments, the composition is for use in the manufacture of a medicament for treatment of a neurodegenerative disease or condition in a subject, optionally wherein the neurodegenerative disease or condition comprises a loss of dopaminergic neurons.

Also provided herein is a method of treatment, comprising implanting in a brain region of a subject having a neurodegenerative disease or condition a therapeutically effective amount of any therapeutic composition disclosed herein, optionally wherein the neurodegenerative disease or condition comprises a loss of dopaminergic neurons.

Also provided herein is a method of engrafting neuronal cells in a brain region of a subject, comprising implanting in a brain region of a subject having a neurodegenerative disease or condition a therapeutically effective amount of any therapeutic composition disclosed herein.

Also provided herein is a method of increasing dopamine production in a brain region of a subject, comprising implanting in a brain region of a subject having a neurodegenerative disease or condition a therapeutically effective amount of any therapeutic composition disclosed herein.

In some embodiments, the neurodegenerative disease or condition comprises a loss of dopaminergic neurons in the substantia nigra, optionally in the SNc. In some embodiments, the neurodegenerative disease or condition is Parkinson's disease. In some embodiments, the neurodegenerative disease or condition is a Parkinsonism. In some embodiments, the brain region is the substantia nigra.

In some embodiments, the implanting is by stereotactic injection. In some embodiments, the neuronal progenitor cells of the therapeutic composition are autologous to the subject.

BRIEF DESCRIPTION OF THE DRAWINGS

Various aspects of the disclosed methods, devices, and systems are set forth with particularity in the appended claims. A better understanding of the features and advantages of the disclosed methods, devices, and systems will be obtained by reference to the following detailed description of illustrative embodiments and the accompanying drawings, of which:

FIG. 1 depicts a non-limiting exemplary method for predicting whether a population of neuronal progenitor cells are likely to successfully engraft when implanted into a region of a brain, in accordance with some embodiments of the present disclosure.

FIG. 2 depicts a non-limiting exemplary method for predicting whether neuronal cells derived from a population of neuronal progenitor cells will produce dopamine after the neuronal progenitor cells are implanted into a brain region, in accordance with some embodiments of the present disclosure.

FIG. 6 depicts a non-limiting exemplary schematic for deriving linear regression models from principal component analysis (PCA), to predict, from the gene expression levels of neuronal progenitor cells, the size of neuronal cell grafts derived from the neuronal progenitor cells after implantation of the neuronal progenitor cells into a subject brain region.

FIG. 11 depicts a non-limiting exemplary schematic for deriving linear regression models without using PCA, to predict, from the gene expression levels of a population of neuronal progenitor cells, the sizes of grafts obtained from the neuronal progenitor cells when the neuronal progenitor cells are implanted into a subject brain.

FIG. 14 depicts a non-limiting example of data that depicts the summary statistics of a linear regression model without using PCA, that is predictive of the size of grafts obtained from implantation of neuronal progenitor cells into a subject brain, based on gene expression levels in the neuronal progenitor cells.

DETAILED DESCRIPTION

Figure 3:
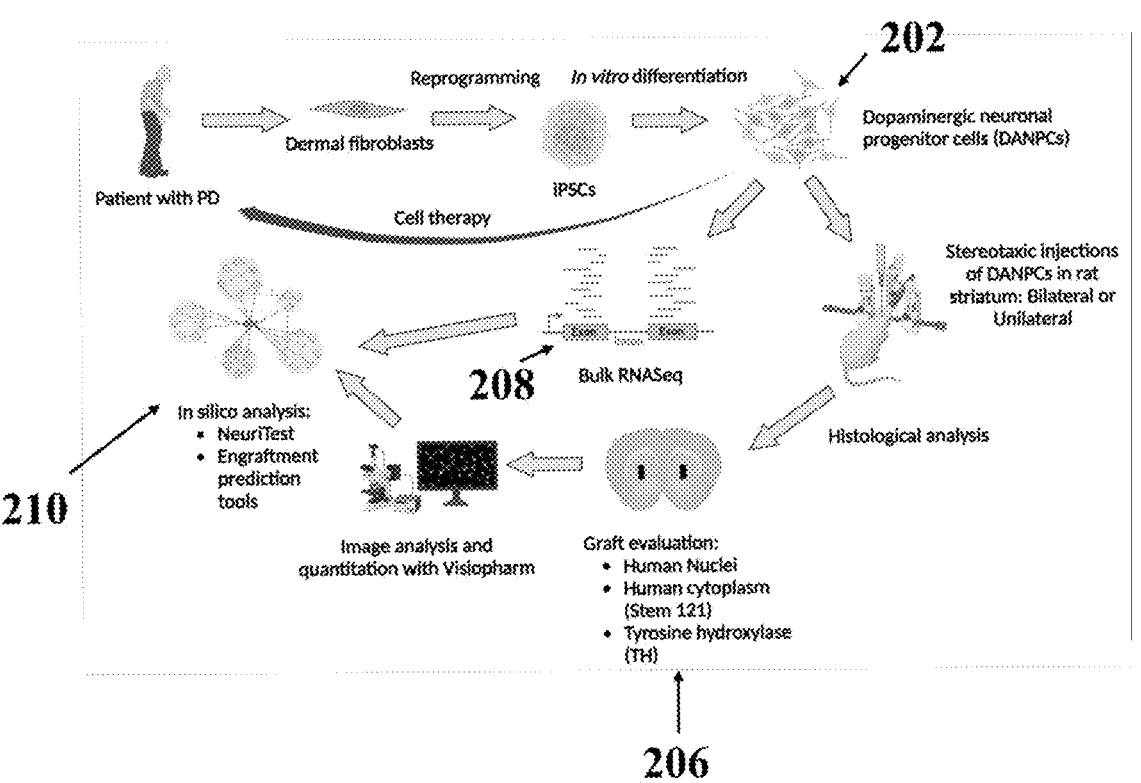
FIG. 3 depicts a non-limiting exemplary schematic for generating neuronal progenitor cells from a subject, to be used for engraftment into rodent brains and to be quantified for gene expression levels.

Provided herein in some embodiments are methods for characterizing a population of neuronal progenitor cells (hereinafter also called dopaminergic neuronal progenitor cells (DANPCs)), such as by predicting whether the population of neuronal progenitor cells or neuronal cells derived from the population of neuronal progenitor cells, is likely to exhibit one more functions or activities or differentiation state. Also provided herein in some embodiments are methods for selecting a population of neuronal progenitor cells in which such cells have one or more desired characteristics that predict whether such neuronal progenitor cells, or neuronal cells derived from the population of neuronal progenitor cells, are likely to exhibit one more functions or activities or differentiation state. Also provided herein in some embodiments are methods for implanting a population of any of such selected population of neuronal progenitor cells to a subject. In some embodiments, the one or more characteristics reflect the mechanism of action of neuronal cells following implantation of neuronal progenitor cells to a subject. In some embodiments, a desired characteristic is the capability of neuronal cells derived from the neuronal progenitor cells to engraft in a brain region of the subject following implantation of the neuronal progenitor cells. In some embodiments, a desired characteristic is the capability of neuronal cells derived from the neuronal progenitor cells to produce dopamine after the neuronal progenitor cells are implanted into a brain. In some embodiments, the methods also can be used to identify or select populations of neuronal progenitor cells that have a characteristic that relates to having a differentiation state that is that of a determined dopaminergic neuron.

Also provided herein in some embodiments are computing devices, including for performing any of the provided methods. Also provided herein in some embodiments are compositions, articles of manufacture, and kits including populations of cells, including populations of cells classified by any of the provided methods as having a desired differentiation state. Also provided herein in some embodiments are methods for implanting into a subject a population of cells having a desired differentiation state, for instance as classified according to any of the provided methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known. Reference to "about" a value or parameter herein includes (and describes) embodiments that are directed to that value or parameter per se. For example, description referring to "about X" includes description of "X".

As used herein, a statement that a cell or population of cells "express" or is "positive" for a particular marker refers to the detectable presence on or in the cell of a particular marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker. When referring to a marker in the cell, such as a transcriptional or translational product, the term refers to the presence of detectable transcriptional or translational product, for example, wherein the product is detected at a level substantially above the level detected carrying out the same procedure with a control under otherwise identical conditions and/or at a level substantially similar to that for a cell known to be positive for the marker, and/or at a level substantially higher than that for a cell known to be negative for the marker.

As used herein, a statement that a cell or population of cells "does not express" or is "negative" for a particular marker refers to the absence of substantial detectable presence on or in the cell of a particular marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker. When referring to a marker in the cell, such as a transcriptional or translational product, the term refers to the absence of detectable transcriptional or translational product, for example, wherein the product is not detected at a level substantially above the level detected carrying out the same procedure with a control under otherwise identical conditions, and/or at a level substantially lower than that for cell known to be positive for the marker, and/or at a level substantially similar as compared to that for a cell known to be negative for the marker.

The term "expression" or "expressed" as used herein in reference to a gene refers to the transcriptional and/or translational product of that gene. The level of expression of a DNA molecule in a cell may be determined on the basis of either the amount of corresponding mRNA that is present within the cell or the amount of protein encoded by that DNA produced by the cell RNA sequencing (RNAseq) is commonly used to determine the level of expression of a gene. See, e.g., Conesa et al. (2016) *Genome Biology* 17:13 (doi.org/10.1186/s13059-016-0881-8) for a review of RNAseq methods.

As used herein, the term "stem cell" refers to a cell characterized by the ability of self-renewal through mitotic cell division and the potential to differentiate into any of multiple cell types. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

"Self renewal" refers to the ability of a cell to divide and generate at least one daughter cell with the self-renewing characteristics of the parent cell. The second daughter cell may commit to a particular differentiation pathway. For example, a self-renewing hematopoietic stem cell can divide and form one daughter stem cell and another daughter cell committed to differentiation in the myeloid or lymphoid pathway.

As used herein, the term "progenitor cell" refers to a cell having the potential to differentiate into any of multiple cell types, but that has lost self-renewal capacity relative to stem cells. For instance, a progenitor cell upon cell division may produce two daughter cells that display a more differentiated (e.g., restricted) phenotype.

As used herein, the term "non-self-renewing cell" refers to a cell that undergoes cell division to produce daughter cells, neither of which have the differentiation potential of the parent cell type, for instance generating differentiated daughter cells.

As used herein, the term "adult stem cell" refers to an undifferentiated cell found in an individual after embryonic development. Adult stem cells multiply by cell division to replenish dying cells and regenerate damaged tissue. An adult stem cell has the ability to divide and create another cell like itself or to create a more differentiated cell. Even though adult stem cells are associated with the expression of pluripotency markers such as Rex1, Nanog, Oct4 or Sox2, they do not have the ability of pluripotent stem cells to differentiate into the cell types of all three germ layers.

As used herein, the term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism.

As used herein, the term "pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

As used herein, the terms "induced pluripotent stem cell," "iPS" and "iPSC" refer to a pluripotent stem cell artificially derived (e.g., through man-made manipulation) from a non-pluripotent cell. A "non-pluripotent cell" can be a cell of lesser potency to self-renew and differentiate than a pluripotent stem cell. Cells of lesser potency can be adult stem cells, tissue specific precursor cells, primary or secondary cells.

The term "specification" or "specified" as provided herein refers to the fate of a cell or tissue narrowed to a limited number of specific cell types. A specified cell can still change its specific fate until it reaches the determined state. A specified cell can be capable of differentiating autonomously (e.g., by itself) when placed in an environment that is neutral with respect to the developmental pathway, such as in a petri dish or test tube. At the stage of specification, cell commitment may still be capable of being altered. If a specified cell is transplanted to a population of differently specified cells, the fate of the transplant can be altered by its interactions with its new neighbors.

A "determined state" as used herein refers to a cell having only one cell type it can differentiate into. For example, determined dopaminergic cells cannot become other types of neurons, though they may not yet be dopaminergic neurons themselves and may or may not express definitive markers of dopaminergic neurons. A determined cell may also be capable of differentiating autonomously when placed into a region of an embryo that is unrelated to said cell. For example, an unrelated region for a determined dopaminergic cell is any organ or tissue other than the brain. A determined cell can also be capable of differentiating autonomously when placed into a cluster of differently specified cells in a petri dish.

The term "differentiated" or "committed" as used herein refers to a cell or cells that have acquired a cell type-specific function.

A "neuronal precursor cell" is a cell that has a tendency to differentiate into a neuronal or glial cell and does not have the pluripotent potential of a stem cell. A neuronal precursor is a cell that is committed to the neuronal or glial lineage and is characterized by expressing one or more marker genes that are specific for the neuronal or glial lineage. The terms "neural" and "neuronal" are used according to their common meaning in the art and can be used interchangeably throughout.

A "dopaminergic cell" or a "differentiated dopaminergic cell" as used herein refers to a cell capable of synthesizing the neurotransmitter dopamine. In embodiments, the dopaminergic cell is an A9 dopaminergic cell. The term "A9 dopaminergic cell" refers to the most densely packed group of dopaminergic cells in the human brain, which are located in the pars compacta of the substantia nigra in the midbrain of healthy, adult humans.

The term "determined dopaminergic cell" as used herein refers to a cell that will differentiate into a dopaminergic neuron and cannot differentiate into a non-dopaminergic cell. A "determined dopaminergic cell" is a cell able to differentiate into a dopaminergic neuron independently of its environment. A determined dopaminergic cell may express Foxa2 or Nurr1. A determined dopaminergic cell may not express serotonin.

As used herein, the term "reprogramming" refers to the process of dedifferentiating a non-pluripotent cell into a cell exhibiting pluripotent stem cell characteristics.

As used herein, the term "cell culture" may refer to an in vitro population of cells residing outside of an organism. The cell culture can be established from primary cells isolated from a cell bank or animal, or secondary cells that are derived from one of these sources and immortalized for long-term in vitro cultures.

As used herein, the terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division.

As used herein, the term "adherent culture vessel" refers to a culture vessel to which a cell may attach via extracellular matrix molecules and the like, and requires the use of an enzyme (e.g., trypsin, dispase, etc.) for detaching cells from the culture vessel. An "adherent culture vessel" is opposed to a culture vessel to which cell attachment is reduced and does not require the use of an enzyme for removing cells from the culture vessel.

As used herein, the term "non-adherent culture vessel" refers to a culture vessel to which cell attachment is reduced or limited, such as for a period of time. A non-adherent culture vessel may contain a low attachment or ultra-low attachment surface, such as may be accomplished by treating the surface with a substance to prevent cell attachment, such as a hydrogel (e.g., a neutrally charged and/or hydrophilic hydrogel) and/or a surfactant (e.g., pluronic acid). A non-adherent culture vessel may contain rounded or concave wells, and/or microwells (e.g., Aggrewells™). In some embodiments, a non-adherent culture vessel is an Aggrewell™ plate. For non-adherent culture vessels, use of an enzyme to remove cells from the culture vessel may not be required.

As used herein, a composition refers to any mixture of two or more products, substances, or compounds, including cells. It may be a solution, a suspension, liquid, powder, a paste, aqueous, non-aqueous or any combination thereof.

The term "pharmaceutical composition" refers to a composition suitable for pharmaceutical use, such as in a mammalian subject (e.g., a human). A pharmaceutical composition typically comprises an effective amount of an active agent (e.g., cells) and a carrier, excipient, or diluent. The carrier, excipient, or diluent is typically a pharmaceutically acceptable carrier, excipient or diluent, respectively.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, a "subject" is a mammal, such as a human or other animal, and typically is human.

Methods for Obtaining Neuronal Progenitor Cells and Determining Gene Expression Levels Provided herein in some embodiments are methods for predicting one or more characteristics of an in vitro population of neuronal progenitor cells. In some embodiments, the provided methods are for identifying or selecting an in vitro population of neuronal progenitor cells having or having the capability of producing cells with one or more characteristics. For example, in some embodiments, the invention provides methods for predicting a population of neuronal progenitor cells will successfully engraft after the neuronal progenitor cells are implanted into the brain of a subject. In some embodiments, the invention provides methods for predicting whether neuronal cells derived from a population of neuronal progenitor cells will produce dopamine.

Pluripotent Stem Cells

In some embodiments, the population of neuronal progenitor cells is obtained by differentiating pluripotent stem cells. In some embodiments, the pluripotent stem cells are embryonic stem (ES) cells, induced pluripotent stem cells (iPSCs), or a combination thereof. In some embodiments, the pluripotent stem cells are human induced pluripotent stem cells. In some embodiments, the pluripotent stem cells are autologous to the subject. In some embodiments, the pluripotent stem cells are allogeneic to the subject. In some embodiments, the pluripotent stem cells are from a healthy human subject. In some embodiments, the pluripotent stem cells are from a human subject with a neurodegenerative disease or condition. In some embodiments, the neurodegenerative disease or condition includes the loss of dopaminergic neurons. In some embodiments, the neurodegenerative disease or condition is a Parkinsonism. In some embodiments, the neurodegenerative disease or condition is Parkinson's disease.

Methods for generating iPSCs are known. For example, one may generate iPSCs by a process known as reprogramming, wherein non-pluripotent cells are effectively "dedifferentiated" to an embryonic stem cell-like state by engineering them to express genes such as OCT4, SOX2, and KLF4. Takahashi and Yamanaka (2006) *Cell* 126:663-76. In some embodiments, fibroblasts may be reprogrammed to iPSCs by transforming fibroblasts with genes (OCT4, SOX2, NANOG, LIN28, and KLF4) cloned into a plasmid (for example, see, Yu et al. (2007) *Science* 318:1917-1920. In some embodiments, non-pluripotent cells such as fibroblasts are reprogrammed to become induced pluripotent stem cells by use of the non-integrating Sendai virus to reprogram the cells (e.g., use of CTS™ CytoTune™-iPS 2.1 Sendai Reprogramming Kit). In some embodiments, the pluripotent stem cells are iPSCs that were artificially derived from non-pluripotent cells of a subject. In some embodiments, the non-pluripotent cells are fibroblasts.

Methods for Differentiating Neuronal Cells

In some embodiments, the population of neuronal progenitor cells are differentiated from pluripotent stem cells under conditions to neurally differentiate the cells. Suitable differentiation methods for obtaining neuronal progenitor cells are known to those of skill in the art. Such methods can involve manipulating gene expression either directly (e.g., by delivery of a genetic payload into a cell) or indirectly (e.g., by using a variety of pharmacological agents to tilt the differentiation pathway towards a neuronal fate (Telias (2023) *Neural Regen. Res.* 18:1273-1274)). The dual-SMAD inhibition protocol is an example of the latter method of neurally differentiating pluripotent stem cells to neuronal progenitor cells (see, e.g., US Patent Publication US2019/0211306). This process can involve exposing pluripotent stem cells to (a) an inhibitor of bone morphogenetic protein (BMP) signaling; (b) an inhibitor of TGF-β/activin-Nodal signaling; and (c) at least one activator of Sonic Hedgehog (SHH) signaling. The method can further include exposing the pluripotent stem cells to at least one inhibitor of GSK3β signaling. Methods for neurally differentiating pluripotent stem cells are also described in, for example, US Patent Publication US2023/0059010, entitled METHODS OF DIFFERENTIATING NEURAL CELLS AND RELATED COMPOSITIONS AND METHODS OF USE, US Patent Publication 2024/0329032 entitled "METHODS OF DIFFERENTIATING NEURAL CELLS AND PREDICTING ENGRAFTMENT THEREOF AND RELATED COMPOSITIONS, and U.S. patent application Ser. No. 18/742,917, filed Jun. 13, 2024, entitled METHODS FOR DIFFERENTIATING DOPAMINERGIC NEURONS FROM STEM CELLS. Additional exemplary methods for differentiating stem-cells into neuronal cells in vitro are described in, for example, WO2014/176606, U.S. Pat. Nos. 8,460,931, 10,273,453, WO2012/095730, U.S. Pat. No. 9,309,495, US2019/0249140, US2018/0298326, WO2009/148170, WO2021/146349, WO2021/216623, WO2021/216622. WO2013/104752, WO2010/096496, WO2013/067362, WO2016/196661, WO2015/143342, and US2016/0348070.

Direct genetic manipulation of stem cells to induce neuronal differentiation can involve introducing a nucleic acid that encodes a neuronal gene, and/or regulatory sequences such as promoters and enhancers. Such methods can involve introducing a nucleic acid construct into the pluripotent stem cells by either (i) plasmid transfection, lipofection, or electroporation, or (ii) use of viral vectors such as adeno-associated virus or lentiviral vectors. Lentiviral-based neuronal differentiation methods are described in, for example, Zhang et al. (2013) *Neuron* 78:785-798.

In some embodiments, the differentiation conditions are by culture that includes an adherent cell culture, such as using methods as described in, for example, US Patent Publication US2019/0211306. In these embodiments, the neuronal progenitor cells are sometimes obtained between day 18 and day 24 after initiation of the differentiation process. In some embodiments, the differentiation conditions include suspension cell culture, such as described herein and in US Patent Publication 2023/0059010 and U.S. patent application Ser. No. 18/742,917. In these embodiments, the neuronal progenitor cells are sometimes obtained between day 13 and day 20 after initiation of the differentiation process, such as on or about day 16. In some embodiments, the pluripotent stem cells are induced pluripotent stem cells (iPSCs). In some embodiments, the pluripotent stem cells are autologous to the subject to which the neuronal progenitor cells are implanted.

Determining Gene Expression Levels

In some embodiments, the gene expression levels, e.g., of cells of any of the test samples or reference cell populations described herein, are determined based on the levels of a gene product synthesized using information encoded by a gene or genes. In some embodiments, a gene product is any biomolecule that is assembled, generated, and/or synthesized with information encoded by a gene, and may include polynucleotides and/or polypeptides. In some embodiments, assessing, measuring, and/or determining gene expression includes determining or measuring the level, amount, or concentration of the gene product. In some embodiments, the level, amount, or concentration of the gene product may be transformed (e.g., normalized) or directly analyzed (e.g., raw).

In some embodiments, the gene product includes a protein, i.e., a polypeptide, that is encoded by and/or expressed by the gene. In particular embodiments, the gene product encodes a protein that is localized and/or exposed on the surface of a cell. In some embodiments, the protein is a soluble protein. In certain embodiments, the protein is secreted by a cell. In particular embodiments, the gene expression is the amount, level, and/or concentration of a protein that is encoded by the gene. In certain embodiments, one or more protein gene products are measured by any suitable means. Suitable methods for assessing, measuring, determining, and/or quantifying the level, amount, or concentration or more or more protein gene products include detection with immunoassays, nucleic acid-based or protein-based aptamer techniques, HPLC (high precision liquid chromatography), peptide sequencing (such as Edman degradation sequencing or mass spectrometry (such as MS/MS), optionally coupled to HPLC), and microarray adaptations of any of the foregoing (including nucleic acid, antibody or protein-protein (i.e., non-antibody) arrays). In some embodiments, the immunoassay is or includes methods or assays that detect proteins based on an immunological reaction, e.g., by detecting the binding of an antibody or antigen binding antibody fragment to a gene product. Immunoassays include quantitative immunocytochemistry or immunohistochemistry, ELISA (including direct, indirect, sandwich, competitive, multiple and portable ELISAs (see, e.g., U.S. Pat. No. 7,510,687), western blotting (including one, two or higher dimensional blotting or other chromatographic means, optionally including peptide sequencing), enzyme immunoassay (EIA), RIA (radioimmunoassay), and SPR (surface plasmon resonance).

In certain embodiments, the gene product is a polynucleotide, e.g., an mRNA or a protein, that is encoded by the gene. In some embodiments, the gene product is a polynucleotide that is expressed by and/or encoded by the gene. In certain embodiments, the polynucleotide is an RNA. In some embodiments, the gene product is a messenger RNA (mRNA), a transfer RNA (tRNA), a ribosomal RNA, a small nuclear RNA, a small nucleolar RNA, an antisense RNA, long non-coding RNA, a microRNA, a Piwi-interacting RNA, a small interfering RNA, and/or a short hairpin RNA. In particular embodiments, the gene product is an mRNA.

In particular embodiments, assessing, measuring, determining, and/or quantifying amount or level of an RNA gene product includes a step of generating, polymerizing, and/or deriving a cDNA polynucleotide and/or a cDNA oligonucleotide from the RNA gene product. In certain embodiments, the RNA gene product is assessed, measured, determined, and/or quantified by directly assessing, measuring, determining, and/or quantifying a cDNA polynucleotide and/or a cDNA oligonucleotide that is derived from the RNA gene product.

In particular embodiments, the amount or level of a polynucleotide in a sample may be assessed, measured, determined, and/or quantified by any suitable means. For example, in some embodiments, the amount or level of a polynucleotide gene product can be assessed, measured, determined, and/or quantified by polymerase chain reaction (PCR), including reverse transcriptase (rt) PCR, droplet digital PCR, real-time and quantitative PCR (qPCR) methods (including, e.g., TAQMAN®, molecular beacon, LIGHTUP™, SCORPION™, SIMPLEPROBES®; see, e.g., U.S. Pat. Nos. 5,538,848; 5,925,517; 6,174,670; 6,329,144; 6,326,145 and 6,635,427); northern blotting; Southern blotting, e.g., of reverse transcription products and derivatives; array based methods, including blotted arrays, microarrays, or in situ-synthesized arrays; and sequencing, e.g., sequencing by synthesis, pyrosequencing, dideoxy sequencing, or sequencing by ligation, or other methods such as discussed in Shendure et al. (2004) *Nat. Rev. Genet.* 5:335-44 or Nowrousian (2010) *Euk. Cell* 9 (9): 1300-1310, including such specific platforms as HELICOS®, ROCHE® 454, ILLUMINA®/SOLEXA®, ABI SOLID® and POLONATOR® sequencing. In particular embodiments, the levels of nucleic acid gene products are measured by quantitative PCR (qPCR) methods, such qRT-PCR.

In particular embodiments, the method for determining gene expression is a quantitative method. In some embodiments, the methods provide a relative gene expression level. In some embodiments, a method for measuring relative amounts of mRNA expression is reverse transcription quantitative polymerase chain reaction (RT-PCR followed with qPCR). RT-PCR initially generates a complementary DNA (cDNA) template from the mRNA by reverse transcription. The cDNA template is then used for qPCR where fluorescence of a probe changes as the DNA amplification progresses. Using a standard curve, qPCR is able to quantitate the relative levels of mRNA species within the sample. RT-qPCR assays employ fluorescent reporter probes (i.e.

TaqMan, Life Technologies) that can be designed for specific mRNA targets which results in minimal cross reactivity and high specificity.

In some embodiments, Total RNA is isolated using standard protocols such as for example using the RNeasy mini kit with gDNA eliminator column (Qiagen Inc.). Total mRNA from each sample is converted to complementary DNA (cDNA) by available methods such as for example using the High Capacity RNA to cDNA kit (Life Technologies). Depending on the estimated numbers of cells collected, the cDNA may undergo preamplification such as for example using the TaqMan PreAmp Master Mix Kit (Invitrogen) prior to qPCR to amplify the cDNA targets equally without introducing bias while increasing the amount of total cDNA that may be required when assaying for multiple targets. In some embodiments, expression levels G genes TTR, PRR16 and CD47 are assessed using TaqMan Gene Expression Assay kits specific for these target proteins (Life Technologies). In some embodiments, expression levels D genes B3GALT5, GREM2 and FRMPD3 are assessed using TaqMan Gene Expression Assay kits specific for these target proteins (Life Technologies).

In some embodiments, gene expression of the target genes may be expressed in a number of ways including as an aggregate score of target gene expression over control gene expression or as expression of an individual target gene. In certain embodiments, the RT-qPCR data is expressed in "Cycles to Threshold" (Ct). As understood by those of skill in the art, Ct is a relative value representing the cycle number at which the fluorescent signals of the amplified DNA reaches a determined threshold level that exceeds background. Because of inter-assay variability and differences in cell numbers from which mRNA is extracted, Ct values are typically normalized against Ct amplification values for a constitutively expressed reference sequence such as a housekeeping gene. Thus, differential expression is considered gene by gene and expressed as normalized Ct values (ACt) of biological replicates between groups of samples. As stated herein, the normalized CT values are also referred to as AACt. In resulting expression, Ct levels are inversely proportional to the amount of target nucleic acid in the sample such that high ACt values represent low expression of a given gene while highly expressed genes have low ACt values.

In some embodiments, the gene expression relative gene expression. In some embodiments, the relative gene expression of a target gene is determined as the ratio of the respective target gene (e.g., G gene or D gene) to that of a reference gene. In some embodiments, the reference gene is a housekeeping gene. In some embodiments, the reference gene is selected from PRS18, IPO8, RPL113A, HSP90AB1, UBC, PSMC4, SDHA, HPRT1, HMBS, TFRC, PPIA, RPL30, GUSB, ACTB, LDHA, RPS17, GAPDH, PPIH, NONO, PUM1, HBB, G6PD, TBP, ALAS1, PGK1, CDKN1A, YWHAZ, POP4, RPLP0 or B2M. In some embodiments, the reference gene is a housekeeping gene that is GAPDH.

Levels of mRNA can also be quantitatively measured by other several methods including northern blotting which gives size and sequence information about the mRNA molecules including discrimination of alternately spliced transcripts. Other methods known in the art include use of DNA microarrays and techniques such as Serial Analysis of Gene Expression (SAGE), which provides relative measures of different mRNAs.

In particular embodiments, the expression of two or more of the genes are measured or assessed simultaneously.

In certain embodiments, a multiplex PCR, e.g., a multiplex rt-PCR assessing or a multiplex quantitative PCR (qPCR) for, measuring, determining, and/or quantifying the level, amount, or concentration of two or more gene products. In some embodiments, microarrays (e.g., AFFYMETRIX®, AGILENT® and ILLUMINA®-style arrays) are used for assessing, measuring, determining, and/or quantifying the level, amount, or concentration of two or more gene products. In some embodiments, the qRT-PCR uses three nucleic acid sets for each gene, where the three nucleic acids comprise a primer pair together with a probe that binds between the regions of a target nucleic acid where the primers bind-known commercially as a TAQMAN® assay.

In some embodiments, microarrays are used for assessing, measuring, determining, and/or quantifying the level, amount, or concentration of a cDNA polynucleotide that is derived from an RNA gene product.

In some embodiments, the expression of one or more gene products, e.g., polynucleotide gene products, is determined by sequencing the gene product and/or by sequencing a cDNA polynucleotide that is derived from the from the gene product. In some embodiments, the sequencing is performed by a non-Sanger sequencing method and/or a next generation sequencing (NGS) technique. Examples of Next Generation Sequencing techniques include Massively Parallel Signature Sequencing (MPSS), Polony sequencing, pyrosequencing, Reversible dye-terminator sequencing, SOLID sequencing, Ion semiconductor sequencing, DNA nanoball sequencing, Helioscope single molecule sequencing, Single molecule real time (SMRT) sequencing, Single molecule real time (RNAP) sequencing, and Nanopore DNA sequencing.

In some embodiments, the NGS technique is RNA sequencing (RNA-Seq). In particular embodiments, the expression of the one or more polynucleotide gene products is measured, determined, and/or quantified by RNA-Seq. RNA-Seq, also called whole transcriptome shotgun sequencing determines the presence and quantity of RNA in a sample. RNA sequencing methods have been adapted for the most common DNA sequencing platforms [HiSeq systems (Illumina), 454 Genome Sequencer FLX System (Roche), Applied Biosystems SOLID (Life Technologies), IonTorrent (Life Technologies). These platforms require initial reverse transcription of RNA into cDNA. Conversely, the single molecule sequencer HeliScope (Helicos BioSciences) is able to use RNA as a template for sequencing. A proof of principle for direct RNA sequencing on the PacBio RS platform has also been demonstrated (Pacific Bioscience). In some embodiments, the one or more RNA gene products are assessed, measured, determined, and/or quantified by RNA-seq. In some embodiments, the RNA-seq is a tag-based RNA-seq. In tag-based methods, each transcript is represented by a unique tag. Initially, tag-based approaches were developed as a sequence-based method to measure transcript abundance and identify differentially expressed genes, assuming that the number of tags (counts) directly corresponds to the abundance of the mRNA molecules. The reduced complexity of the sample, obtained by sequencing a defined region, was essential to make the Sanger-based methods affordable. When NGS technology became available, the high number of reads that could be generated facilitated differential gene expression analysis. A transcript length bias in the quantification of gene expression levels, such as observed for shotgun methods, is not encountered in tag-based methods. All tag-based methods are by definition strand specific. In particular embodiments, the one or more RNA gene products are assessed, measured, determined, and/or quantified by tag-based RNA-seq.

In some embodiments, the RNA-seq is a shotgun RNA-seq. Numerous protocols have been described for shotgun RNA-seq, but they have many steps in common: fragmentation (which can occur at RNA level or cDNA level, conversion of the RNA into cDNA (performed by oligo dT or random primers), second-strand synthesis, ligation of adapter sequences at 3' and 5' ends (at RNA or DNA level) and final amplification. In some embodiments, RNA-seq can focus only on polyadenylated RNA molecules (mainly mRNAs but also some lncRNAs, snoRNAs, pseudogenes and histones) if poly(A)+ RNAs are selected prior to fragmentation, or may also include non-polyadenylated RNAs if no selection is performed. In the latter case, ribosomal RNA (more than 80% of the total RNA pool) needs to be depleted prior to fragmentation. It is, therefore, clear that differences in capturing of the mRNA part of the transcriptome lead to a partial overlap in the type of detected transcripts. Moreover, different protocols may affect the abundance and the distribution of the sequenced reads. This makes it difficult to compare results from experiments with different library preparation protocols.

In some embodiments, RNA from each sample is obtained, fragmented and used to generate complementary DNA (cDNA) samples, such as cDNA libraries for sequencing. Reads may be processed and aligned to the human genome and the expected number of mappings per gene/isoform are estimated and used to determine read counts. In some embodiments, read counts are normalized by the length of the genes/isoforms and number of reads in a library to yield FPKM normalized, e.g., by length of the genes/isoforms and number of reads in the library, to yield fragments per kilobase of exon per million mapped reads (FPKM) according to the gene length and total mapped reads. In some aspects, between-sample normalization is achieved by normalization, such as 75th quantile normalization, where each sample is scaled by the median of 75th quantiles from all samples, e.g., to yield quantile-normalized FPKM (FPKQ) values. The FPKQ values may be log-transformed (log 2).

In some embodiments, RNA from each sample is obtained, fragmented and used to generate complementary DNA (cDNA) samples, such as cDNA libraries for sequencing. Reads may be processed and aligned to the human genome and the expected number of mappings per gene/isoform are estimated and used to determine read counts. In some embodiments, read counts are normalized by the length of the genes/isoforms and number of reads in a library. In some embodiments, read counts are provided as counts per million (CPM). In some embodiments, the CPM read counts are log-transformed (e.g., log 2).

In some embodiments, relative gene expression is measured by comparing the CPM of a target gene to the CPM of a reference gene, such as a housekeeping gene. In some embodiments, the housekeeping gene is GAPDH. In some embodiments, the relative gene expression of a target gene is determined as the ratio of the CPM of the target gene to CPM of a housekeeping gene (e.g., GAPDH).

In some embodiments, the gene expression levels are obtained using microarray analysis. In some embodiments, the gene expression levels are obtained using RNA sequencing. In some embodiments, the gene expression levels are obtained using both microarray analysis and RNA sequencing. In some embodiments, the RNA sequencing is performed on bulk RNA from a plurality of cells. In some embodiments, bulk RNA sequencing data is obtained from pooled RNA from the plurality of cells. In some embodiments, the RNA sequencing is performed on single cells. In some embodiments, the RNA sequencing is performed on bulk RNA from a plurality of cells and on single cells.

Any suitable methods for obtaining bulk RNA sequencing data can be used (for example, see Chao et al. (2019) *BMC Genomics* 20:571). For instance, total RNA from a sample, e.g., a plurality of cells from a population of cells, can be isolated using TRIZOL, treated with DNase I, and purified. Concentration and quality of isolated RNA can be measured and checked prior to library preparation for total RNA or mRNA. For library preparation, total RNA or mRNA can be fragmented and converted to cDNA using reverse transcription. After construction, amplification, and optional barcoding of double-stranded cDNA, libraries can be processed for next generation sequencing using any suitable library preparation techniques, sequencing platforms, and genomic-alignment tools.

In some embodiments, the gene expression levels are obtained using single-cell RNA sequencing. In some embodiments, the use of single-cell RNA sequencing data affords certain advantages. In some embodiments, the use of single-cell RNA sequencing data allows for characterization of subpopulations of cells, for instance of determined dopaminergic cells within a larger population of cells. In some embodiments, the use of single-cell RNA sequencing data reduces the number of cells required for use in the methods provided herein, e.g., reduces the number of cells needed to obtain data for training a machine learning model. In some embodiments, the use of single-cell RNA sequencing data improves characterization of biological variability across cells. In some embodiments, the use of single-cell RNA sequencing data allows for easier validation and interpretation of gene expression levels.

Any suitable methods for single-cell RNA sequencing can be used (for example, see Zheng et al. (2017) *Nature Communications* 8:14049 and Haque et al. (2017) *Genome Medicine* 9:75). For single-RNA sequencing, single cells from a sample, for instance an in vitro population of cells, can be isolated using flow cytometric cell-sorting, microfluidic platform, or droplet-based methods. Isolated cells are lysed to allow capture of RNA molecules. Poly[T]-primers can be used for the analysis of polyadenylated mRNA molecules specifically, and primed mRNA molecules are converted to cDNA using reverse transcription. In some instances, unique molecular identifiers can be used to mark single mRNA molecules based on cellular origin. The cDNA pool can then amplified, optionally barcoded, and sequenced, for instance using next-generation sequencing (NGS) and with library preparation techniques, sequencing platforms, and genomic-alignment tools similar to those used for bulk RNA samples. In some instances, unbiased cell-type classification within a mixed population of distinct cell types can be achieved with as few as 10,000 to 50,000 reads per cell, and single-cell libraries from various common protocols can be close to saturation when sequenced to a depth of 1,000,000 reads.

In some embodiments, the gene expression levels include bulk RNA sequencing data and single-cell RNA sequencing data. In some embodiments, the bulk RNA sequencing data and the single-cell RNA sequencing data are obtained from the same population of cells. In some embodiments, the single-cell RNA sequencing data can be used to approximate the bulk RNA sequencing data obtained from the same population of cells. In some embodiments, approximated bulk RNA sequencing data is obtained by averaging single-cell RNA sequencing data from cells in the same population of cells. In some embodiments, the gene expression levels include approximated bulk RNA sequencing data.

Methods for Determining Characteristics of Neuronal Progenitor Cells

In some embodiments, the provided methods include using gene expression levels of a plurality of genes for one or more cells of the population of neuronal progenitor cells in order to predict if the population of neuronal progenitor cells will engraft following implantation into a brain of a subject. In other embodiments, the provided methods include using gene expression levels of a plurality of genes for one or more cells of the population of neuronal progenitor cells in order to predict if the population of neuronal progenitor cells produce neuronal cells that produce dopamine following implantation of the neuronal progenitor cells into a brain of a subject.

The provided methods are based on the finding that certain gene expression levels in a neuronal progenitor cell population correlate to predicting desirable characteristics of cells that are derived from such cells following their implantation into a subject. The methods alleviate the variability that may otherwise exist when producing cell products differentiated from pluripotent stem cells. Consistency of an administered cell product is important for maximizing the efficacy of a cell product across multiple different subjects. This is especially true for autologous cell therapies where there can be higher variability due to donor differences and due to the potential of some variability in manufacturing processes. The provided methods result in a more consistent cell product with higher confidence, thus improving treatment options for subjects, particularly those being administered neuronal progenitor cells derived from their own cells. The ability to assess, based on gene expression levels of neuronal progenitor cells before the cells are implanted for therapeutic purposes, whether the progenitor cells will give rise to neuronal cells that have desired characteristics after implantation, is an important advancement towards making pluripotent stem cell-derived cell therapies successful.

Predicting Engraftment

In some embodiments, the invention provides methods for predicting whether a population of neuronal progenitor cells are likely to successfully engraft in a brain region following implantation to a subject. In some embodiments, the prediction indicates the ability of the cells to engraft and form mature dopamine neuron grafts of a certain size after implantation. In some embodiments, cell engraftment of cells derived from the neuronal progenitor cells is predicted using gene expression levels of a one of a plurality of genes in a test sample of a population of neuronal progenitor cells, in which the genes are associated with engraft capability following implantation to a subject (hereinafter called "G genes"). Exemplary G genes are described herein including in Table E1. In some embodiments, the G genes are selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2.

In some embodiments, the methods include predicting the neuronal engraftment capability of the neuronal progenitor cells by correlating the determined gene expression level of the one or more G genes in the test sample with a reference plot for each G gene that associates graft size with gene expression levels of the G gene in a training set that comprises one or more reference samples. In some embodiments, the gene expression levels of the G genes are associated with the ability of the population of neuronal progenitor cells to result in cells that engraft in a brain region of a subject following implantation of the population of neuronal progenitor cells into the brain region. In some embodiments, a population of neuronal progenitor cells is selected for implantation for therapeutic purposes based on the gene expression levels of one or more of the G genes.

In some embodiments, each data point on the reference plot is determined by: (a) measuring the gene expression level of the G gene in a reference sample that includes a population of neuronal progenitor cells; (b) implanting neuronal progenitor cells from the reference sample of into a brain region of a test animal and measuring the size of a graft formed by the implanted neuronal progenitor cells after an incubation period; and (c) plotting the graft size against the expression level of the G gene to obtain a data point for the training sample. As shown herein, certain G genes are associated with the potential of neuronal cells derived from neuronal progenitor cells to engraft to a certain size following their implantation, as demonstrated using a rat model as a surrogate for implantation. Exemplary genes were identified by a machine learning process that was trained based on gene expression using reference neuronal progenitor cell populations that were correlated to producing grafts of certain sizes following their implantation into a brain region.

In some embodiments, the reference plot is obtained by applying the gene expression levels of the one or more G genes in the test sample as input to a machine learning model configured to predict whether neuronal cells derived from a population of neuronal progenitor cells will successfully engraft after the neuronal progenitor cells are implanted into a brain region, wherein the machine learning model is trained using gene expression levels of the G genes in a plurality of reference populations of neuronal progenitor cells.

In some embodiments, the engraftment fitness of a reference population indicates whether or not the reference population engrafted in a brain region of a subject following implantation of the reference population into the brain region. In some embodiments, the engraftment fitness of a reference population indicates the degree to which the reference population engrafted in a brain region of a subject following implantation of the reference population into the brain region.

In some embodiments, the reference populations include populations of neuronal progenitor cells that engrafted following implantation. In some embodiments, the reference populations include populations of neuronal progenitor cells that did not engraft following implantation. In some embodiments, the reference populations include populations of neuronal progenitor cells that engrafted following implantation as well as populations of neuronal progenitor cells that did not engraft following implantation.

In some embodiments, the reference populations have been differentiated from pluripotent stem cells under conditions to neurally differentiate the cells. In some embodiments, the reference populations have been cultured to differentiate cells to determined dopaminergic neuron progenitor cells. In some embodiments, the reference populations includes determined dopaminergic neuron progenitor cells. Exemplary methods of neurally differentiating cells in order to form the reference populations are described herein.

In some embodiments, the reference populations are all formed using the same method of neurally differentiating cells, e.g., using any of the methods described herein. In some embodiments, the reference populations are formed using a number of different methods of neurally differentiating cells, e.g., using a number of any of the methods described herein.

In some embodiments, the engraftment fitness of a reference population is determined based on the number of cells derived from the reference population that are present in the brain region following the implantation. In some embodiments, the number of cells is counted at, about, at least, or at least about 7 days, 14 days, or 21 days following the implantation. In some embodiments, the number of cells is counted at, about, at least, or at least about 7 days following the implantation. In some embodiments, the number of cells is counted at, about, at least, or at least about 14 days following the implantation. In some embodiments, the number of cells is counted at, about, at least, or at least about 21 days following the implantation.

In some embodiments, the population of neuronal progenitor cells is predicted to result in neuronal cells that engraft in the brain region of the subject if cells derived from the implanted neuronal progenitor cells are predicted to form a graft size at or above a threshold graft size value in the brain region following the implantation. In some embodiments, the threshold graft size value is equal to or greater than 1,000 cells in a cross section of the brain region. In some embodiments, the brain region is the substantia nigra and the cross section represents approximately ⅙ of the substantia nigra.

In some embodiments, the methods of predicting cell engraftment capability of neuronal cells obtained from a population of neuronal progenitor cells includes (a) determining, in a test sample that comprises a population of neuronal progenitor cells, a gene expression level for one or more gene associated with engraftment (G genes), wherein the G genes are selected from the group consisting of AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; and (b) comparing the gene expression level in the test sample for each G gene of the one or more G genes to a control level for the expression level of the G gene, thereby predicting whether neuronal cells derived from the neuronal progenitor cells are likely to engraft in a brain region of a subject following implantation of the population of neuronal progenitor cells in the brain region.

In some embodiments, the predicted engraftment capability is determined for at least 2, 3, 4, 5, 6, 7, 8, 9, 10, 11, 12, 13, 14, 15, 16, 17, 18, 19 or 20 of the G genes and an overall engraftment capability prediction for the test sample is based on a combined assessment of the predicted engraftment capabilities obtained for each of the two or more G genes. In some embodiments, the combined assessment involves determining a mean or a median predicted engraftment capability.

In some embodiments, the G genes are selected from the group consisting of TTR, PRR16, CMTM8, APOA1, CD47, CDO1, KIR26A and CNTN2. In some embodiments, the G genes are three of more G genes selected from the group consisting of TTR, PRR16, CMTM8, APOA1, CD47, CD01, KIR26A and CNTN2. In some embodiments, the one or more G genes are selected from the group consisting of TTR, PRR16 and CD47. In some embodiments, G genes are TTR, PRR16 and CD47.

In some embodiments, the invention provides methods of predicting whether a population of neuronal progenitor cells are likely to successfully engraft when implanted into a brain region, in which the methods involve: (a) determining a gene expression level for one or more genes associated with engraftment (G genes) in a test sample that comprises a population of neuronal progenitor cells, wherein the one or more G genes are selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; and (b) comparing the expression level of each of the one or more G genes in the test population of neuronal progenitor cells to a predetermined threshold value for the particular G gene, wherein high engraftment capability of the neuronal progenitor cells is indicated if the expression level is either: (i) above the predetermined threshold value for that G gene; or (ii) below the predetermined threshold value for that G gene; wherein "above" or "below" is defined by the known biological relevance of the G gene in the context of engraftment capability.

In some of these embodiments, the predetermined threshold value for the particular G gene is based on the expression level of the G gene in a training sample that includes neuronal progenitor cells that are known to exhibit high engraftment levels when implanted into a brain, and a gene expression level for the G gene in the test sample that is similar to the expression level of the G gene in the training sample is predictive of high engraftment potential for neuronal cells derived from the neuronal progenitor cells in the test sample. In other embodiments, the predetermined threshold value for the particular G gene is based on the expression level of the G gene in a training sample that includes neuronal progenitor cells that are known to exhibit low engraftment levels when implanted into a brain, and a gene expression level for the G gene in the test sample that is similar to the expression level of the G gene in the control sample is predictive of low engraftment potential for neuronal cells derived from the neuronal progenitor cells in the test sample.

In some embodiments, the prediction is made by comparing the gene expression level in the test sample for each G gene of the one or more G genes to a control level for the expression level of the G gene. In some embodiments, the control expression level is obtained by performing the assay used for determining gene expression level on a control sample. In some embodiments, the control sample comprises a known quantity of a nucleotide that encodes at least a portion of the G gene. In some embodiments, the control sample comprises a reference sample of neuronal progenitor cells. In some embodiments, the reference sample comprises a pooled sample of neuronal progenitor cells from multiple donors. In some embodiments, the reference sample comprises neuronal progenitor cells that are known to produce neuronal cells that exhibit high engraftment levels, and a gene expression level for the G gene in the test sample that is similar to the expression level of the G gene in the control sample is predictive of high engraftment potential for neuronal cells derived from the neuronal progenitor cells. In some embodiments, the reference sample comprises neuronal progenitor cells that are known to produce neuronal cells that exhibit low engraftment levels, and a gene expression level for the G gene in the test sample that is similar to the expression level of the G gene in the control sample is predictive of low engraftment potential for neuronal cells derived from the neuronal progenitor cells.

In some embodiments, the control expression level is a predetermined threshold value, such as based on a threshold expression level that correlates (positively or negatively) to whether neuronal cells derived from the neuronal progenitor cells have a high engraftment capability in the brain region. In some embodiments, neuronal cells derived from the neuronal progenitor cells are predicted to engraft in the brain region if: (i) the gene expression level of at least one first G gene selected from the group consisting of AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2 is lower than the predetermined threshold value for the first G gene; and/or (ii) the gene expression levels of at least one second G gene selected from the group consisting of DYNLL2, ITGA3, RPS6KL1, CHRNB2, SULT4A1, PTPN3, LZTS1, RUNX1T1, TMEM145, EPHA10, CAR-MIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2 is greater than the predetermined threshold value for the second G gene.

In some embodiments, the gene expression level is the ratio of the relative expression level of the G gene in the test sample to a reference gene and the predetermined threshold value is a threshold value of the ratio. In some embodiments, each ratio is calculated as counts per million (CPM) of [Gene]/CPM of reference gene. In some embodiments, each ratio is calculated as log CPM of [Gene]/log CPM of reference gene. In some embodiments, each ratio is calculated by qPCR as a relative expression of a target gene to a reference gene, such as a housekeeping gene. In some embodiments, the reference gene is a housekeeping gene. In some embodiments, the reference gene is selected from PRS18, IPO8, RPL113A, HSP90AB1, UBC, PSMC4, SDHA, HPRT1, HMBS, TFRC, PPIA, RPL30, GUSB, ACTB, LDHA, RPS17, GAPDH, PPIH, NONO, PUM1, HBB, G6PD, TBP, ALAS1, PGK1, CDKN1A, YWHAZ, POP4, RPLP0 or B2M. In some embodiments, the reference gene is a housekeeping gene such as GAPDH.

In some embodiments, the predetermined threshold value for the particular G gene is based on a ratio of the relative expression levels in the test sample of a) the G gene, and b) a control gene. For example, in some embodiments, the control gene is GAPDH and the predetermined threshold value is selected from the group consisting of: (a) a ratio of AC000120.3 to GAPDH expression of less than about 0.14; (b) a ratio of KRT77 to GAPDH expression of less than about 0.68; (c) a ratio of TTR to GAPDH expression of less than about 1.11; (d) a ratio of PRR16 to GAPDH expression of less than about 0.43; (e) a ratio of MEGF10 to GAPDH expression of less than about 0.79; (f) a ratio of PDE3A to GAPDH expression of less than about 1.00; (g) a ratio of GDPD2 to GAPDH expression of less than about 0.78; (h) a ratio of CMTM8 to GAPDH expression of less than about 1.02; (i) a ratio of APOA1 to GAPDH expression of less than about 0.68; (j) a ratio of CMTM7 to GAPDH expression of less than about 0.88; (k) a ratio of CDHR3 to GAPDH expression of less than about 1.09; (1) a ratio of CORIN to GAPDH expression of less than about 1.24; (m) a ratio of VTN to GAPDH expression of less than about 0.98; (n) a ratio of CPNE8 to GAPDH expression of less than about 0.79; (o) a ratio of EFEMP1 to GAPDH expression of less than about 0.83; (p) a ratio of CD47 to GAPDH expression of less than about 1.16; (q) a ratio of SPARC to GAPDH expression of less than about 1.29; (r) a ratio of JAM2 to GAPDH expression of less than about 0.82; (s) a ratio of CDO1 to GAPDH expression of less than about 1.00; (t) a ratio of PLXDC2 to GAPDH expression of less than about 1.00; (u) a ratio of DYNLL2 to GAPDH expression of greater than about 0.56; (v) a ratio of ITGA3 to GAPDH expression of greater than about 0.26; (w) a ratio of RPS6KL1 to GAPDH expression of greater than about 0.21; (x) a ratio of CHRNB2 to GAPDH expression of greater than about 0.23; (y) a ratio of SULT4A1 to GAPDH expression of greater than about 0.22; (z) a ratio of PTPN3 to GAPDH expression of greater than about 0.03; (aa) a ratio of LZTS1 to GAPDH expression of greater than about 0.19; (ab) a ratio of RUNX1T1 to GAPDH expression of greater than about 0.24; (ac) a ratio of TMEM145 to GAPDH expression of greater than about 0.05; (ad) a ratio of EPHA10 to GAPDH expression of greater than about 0.16; (ae) a ratio of CARMIL3 to GAPDH expression of greater than about 0.16; (af) a ratio of MANEAL to GAPDH expression of greater than about 0.24; (ag) a ratio of TMEM176B to GAPDH expression of greater than about 0.11; (ah) a ratio of MPP3 to GAPDH expression of greater than about 0.12; (ai) a ratio of DRAXIN to GAPDH expression of greater than about 0.27; (aj) a ratio of ADGRB1 to GAPDH expression of greater than about 0.07; (ak) a ratio of KIF26A to GAPDH expression of greater than about 0.23; (al) a ratio of CELF5 to GAPDH expression of greater than about 0.25; (am) a ratio of CNTN2 to GAPDH expression of greater than about 0.23; (an) a ratio of ASPHD1 to GAPDH expression of greater than about 0.08; (ao) a ratio of SVOP to GAPDH expression of greater than about 0.16; (ap) a ratio of ANGPT2 to GAPDH expression of greater than about 0.06; (aq) a ratio of SLC22A15 to GAPDH expression of greater than about 0.04; (ar) a ratio of SRRM3 to GAPDH expression of greater than about 0.17; (as) a ratio of GRIN2D to GAPDH expression of greater than about 0.02; (at) a ratio of DACH2 to GAPDH expression of greater than about 0.06; (au) a ratio of CHST1 to GAPDH expression of greater than about 0.04; (av) a ratio of GRIN1 to GAPDH expression of greater than about 0.26; (aw) a ratio of LHX5 to GAPDH expression of greater than about 0.06; and (ax) a ratio of NOS2 to GAPDH expression of greater than about 0.08.

In some embodiments, the predetermined threshold value is selected from the group consisting of: (i) a ratio of TTR to GAPDH expression of less than about 1.11; (ii) a ratio of PRR16 to GAPDH expression of less than about 0.43; (iii) a ratio of CMTM8 to GAPDH expression of less than about 1.02; (iv) a ratio of APOA1 to GAPDH expression of less than about 0.68; (v) a ratio of CD47 to GAPDH expression of less than about 1.16; (vi) a ratio of CDO1 to GAPDH expression of less than about 1.00; (vii) a ratio of KIF26A to GAPDH expression of greater than about 0.23; and (viii) a ratio of CNTN2 to GAPDH expression of greater than about 0.23. In some embodiments, the predetermined threshold value is selected from at least two, three, four, five, six, or seven ratios from among (i) to (viii).

In some embodiments, the predetermined first threshold levels values are selected from: a ratio of TTR to GAPDH expression of less than about 1.11; and/or a ratio of PRR16 to GAPDH expression of less than about 0.43; and/or a ratio of CD47 to GAPDH expression of less than about 1.16.

In some embodiments, the predetermined first threshold values are: a ratio of TTR to GAPDH expression of less than about 1.11; a ratio of PRR16 to GAPDH expression of less than about 0.43; and a ratio of CD47 to GAPDH expression of less than about 1.16.

The invention also provides, in some embodiments, methods for training a machine learning model for predicting whether a population of neuronal progenitor cells are likely to successfully engraft when implanted into a brain region. These methods can include: (a) obtaining gene expression levels for one or more genes in each of a plurality of reference populations of neuronal progenitor cells; (b) receiving engraftment fitness information for each of the plurality of reference populations, wherein the engraftment fitness information of a reference population indicates whether or not, or the degree to which, neuronal progenitor cells of the reference population engrafted in a brain region of a subject following implantation of the neuronal progenitor cells into the brain region; and (c) applying the gene expression levels of (a) and applying the engraftment fitness information of (b) as input to train a machine learning model, wherein the machine learning model is trained to predict based on the gene expression levels of the plurality of genes if a population of neuronal progenitor cells will engraft in a brain region of a subject following implantation of the population of neuronal progenitor cells into the brain region.

Predicting Dopamine Production

In some embodiments, the invention provides methods of predicting whether neuronal cells derived from a population of neuronal progenitor cells will produce dopamine. In some embodiments, the methods relate to predicting whether neuronal cells resulting or derived from the neuronal progenitor cells will produce dopamine, such as a threshold level of dopamine. In some embodiments, the prediction is based on the ability of the cells to produce dopamine in a particular amount as determined on a per cell basis.

In some embodiments, dopamine production from cells derived from the neuronal progenitor cells is predicted using gene expression levels of a one of a plurality of genes in a test sample of a population of neuronal progenitor cells, in which the genes are associated with the ability neuronal cells that arise from the neuronal progenitor cells to produce or release dopamine (hereinafter called "D genes"). Exemplary D genes are described herein including in Table E2. In some embodiments, provided methods involve: (a) determining a gene expression level for one or more gene associated with predicted dopamine production (D genes) in a test sample that comprises a population of neuronal progenitor cells, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; and (b) predicting the dopamine production capability of neuronal cells derived from the neuronal progenitor cells by correlating the determined gene expression level of the one or more D genes in the test sample with a reference plot for each D gene that associates dopamine production by the neuronal cells with gene expression levels of the D gene in a training set that comprises one or more reference samples. In some embodiments, a population of neuronal progenitor cells is selected for implantation for therapeutic purposes based on the gene expression levels of one or more of the D genes.

In some embodiments, each data point on the reference plot is determined by: (a) measuring the gene expression level of the D gene in a reference sample that includes a population of neuronal progenitor cells; (b) differentiating the neuronal progenitor cells to produce neuronal cells and measuring the amount of dopamine produced by neuronal cells derived from the neuronal progenitor cells; and (c) plotting the dopamine production against the expression level of the D gene to obtain a data point for the training sample. In some embodiments, the reference plot includes a plurality of data points that are obtained for each of a plurality of reference samples.

In some embodiments, the reference plot is obtained by applying the gene expression levels of the one or more D genes in the test sample as input to a machine learning model configured to predict whether neuronal cells derived from a population of neuronal progenitor cells will produce dopamine, wherein the machine learning model is trained using gene expression levels of the D genes in a plurality of reference populations of neuronal progenitor cells As shown herein, certain D genes are associated with the potential of neuronal progenitor cells to give rise to neuronal cells that produce dopamine, such as demonstrated by a surrogate assay involving long-term in vitro culture of the neuronal progenitor cells under conditions in which the cells mature to dopaminergic neurons in culture. In particular, the long-term culture is to prepare a preparation of mature dopamine neurons in vitro by culture of the neuronal progenitor cells for about 60 days (including the initial culture to differentiate iPSCs to neuronal progenitor cells and about 60 additional days to generate mature dopamine neurons). Exemplary genes were identified by a machine learning process that was trained based on gene expression using reference neuronal progenitor cell populations that were correlated to dopamine production at a particular threshold amount following the culture to prepare mature dopamine neurons. In some embodiments, in addition to dopamine neurotransmitter data as well as measure of serotonin also can be determined as an alternative, or in addition to, dopamine production in a culture preparation of mature dopamine neurons. In some embodiments, dopamine production and serotonin production can be assessed after stimulation of the mature dopamine neurons with potassium chloride (KCl). In some embodiments, neurotransmitter release can be assessed by liquid chromatography mass spectrometry (LC-MS).

In some embodiments, the dopamine release of a reference population of mature dopamine neurons derived from a reference neuronal progenitor cell population indicates whether or not the reference population is capable of producing neuronal cells that produce dopamine. In some embodiments, the fitness for dopamine production of a reference population indicates the degree to which the reference population is able to produce dopamine-producing neuronal cells.

In some embodiments, the reference populations include populations of neuronal progenitor cells that differentiate to mature dopaminergic neurons and produce dopamine. In some embodiments, the reference populations include populations of neuronal progenitor cells that differentiate to neuronal cells that do not produce dopamine. In some embodiments, the reference populations include populations of neuronal progenitor cells that differentiate to mature dopaminergic neurons and produce dopamine as well as populations of neuronal progenitor cells that differentiate to neuronal cells that do not produce dopamine.

In some embodiments, the population of neuronal progenitor cells is predicted to result in cells that exhibit dopamine production if neuronal cells derived from the implanted neuronal progenitor cells are predicted to result in dopamine production at or above a threshold dopamine value. In some embodiments, the threshold dopamine value of dopamine is equal to or greater than 15 nM dopamine/$10^5$ cells.

In some embodiments, the methods of predicting dopamine production by neuronal cells obtained from a population of neuronal progenitor cells includes (a) determining, in a test sample that comprises a population of neuronal progenitor cells, a gene expression level for one or more gene associated with dopamine production (D genes), wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; and (b) comparing the gene expression level in the test sample for each D gene of the one or more D genes to a predetermined threshold value for the particular D gene, wherein high engraftment capability of the neuronal progenitor cells is indicated if the expression level is either: (i) above the predetermined threshold value for that D gene; or (ii) below the predetermined threshold value for that D gene; wherein "above" or "below" is defined by the known biological relevance of the D gene in the context of dopamine production capability.

In some of these embodiments, the predetermined threshold value for the particular D gene is based on the expression level of the D gene in a training sample that includes neuronal progenitor cells that are known to produce neuronal cells that produce high amounts of dopamine, and a gene expression level for the D gene in the test sample that is similar to the expression level of the D gene in the training sample is predictive of dopamine production potential for neuronal cells derived from the neuronal progenitor cells in the test sample. In other embodiments, the predetermined threshold value for the particular D gene is based on the expression level of the D gene in a training sample that includes neuronal progenitor cells that are known to give rise to neuronal cells that produce low amounts of dopamine, and a gene expression level for the D gene in the test sample that is similar to the expression level of the D gene in the control sample is predictive of low dopamine production potential for neuronal cells derived from the neuronal progenitor cells in the test sample.

In some embodiments, the dopamine production capability is determined for at least 2, 3, 4, 5, 6, 7, 8, 9, 10, 11, 12, 13, 14, 15, 16, 17, 18, 19 or 20 of the D genes and an overall dopamine production capability prediction for the test sample is based on a combined assessment of the predicted dopamine production capabilities obtained for each of the two or more D genes. In some embodiments, the combined assessment involves determining a mean or a median predicted dopamine production capability.

In some embodiments the D genes are selected from the group consisting of CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the D genes are three of more D genes selected from the group consisting of CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the one or more D genes are B3GALT5, FRMPD3, and GREM2.

In some embodiments, the prediction is by comparing the gene expression level in the test sample for each D gene of the one or more D genes to a control level for the expression level of the D gene. In some embodiments, the control expression level is obtained by performing the assay used for determining gene expression level on a control sample. In some embodiments, the control sample comprises a known quantity of a nucleotide that encodes at least a portion of the D gene. In some embodiments, the control sample includes a reference sample of neuronal progenitor cells. In some embodiments, the reference sample includes a pooled sample of neuronal progenitor cells from multiple donors. In some embodiments, the reference sample includes neuronal progenitor cells that are known to produce neuronal cells that exhibit high dopamine production levels, and a gene expression level for the D gene in the test sample that is similar to the expression level of the D gene in the control sample is predictive of high dopamine production potential for neuronal cells derived from the neuronal progenitor cells. In some embodiments, the reference sample includes neuronal progenitor cells that are known to produce neuronal cells that exhibit low dopamine production levels, and a gene expression level for the D gene in the test sample that is similar to the expression level of the d gene in the control sample is predictive of low dopamine production potential for neuronal cells derived from the neuronal progenitor cells.

In some embodiments, the control expression level is a predetermined threshold value, such as based on a threshold expression level that correlates (positively or negatively) to whether neuronal cells derived from the neuronal progenitor cells are likely to produce dopamine. In some embodiments, neuronal cells derived from the neuronal progenitor cells are predicted to produce dopamine if: (i) the gene expression level of at least one first D gene selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1 and ZHX1 is lower than the predetermined threshold value for the first D gene; and/or (ii) the gene expression levels of at least one second D gene selected from the group consisting of BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1 is higher than the predetermined threshold value for the second D gene.

In some embodiments, the gene expression level is the ratio of the relative expression level of the D gene in the test sample to a reference gene and the predetermined threshold value is a threshold value of the ratio. In some embodiments, each ratio is calculated as counts per million (CPM) of [Gene]/CPM of reference gene. In some embodiments, each ratio is calculated as log CPM of [Gene]/log CPM of reference gene. In some embodiments, each ratio is calculated by qPCR as a relative expression of a target gene to a reference gene, such as a housekeeping gene. In some embodiments, the reference gene is a housekeeping gene. In some embodiments, the reference gene is selected from PRS18, IPO8, RPL113A, HSP90AB1, UBC, PSMC4, SDHA, HPRT1, HMBS, TFRC, PPIA, RPL30, GUSB, ACTB, LDHA, RPS17, GAPDH, PPIH, NONO, PUM1, HBB, G6PD, TBP, ALAS1, PGK1, CDKN1A, YWHAZ, POP4, RPLP0 or B2M. In some embodiments, the reference gene is a housekeeping gene such as GAPDH.

In some embodiments, the predetermined threshold value for the particular D gene is based on a ratio of the relative expression levels in the test sample of a) the D gene, and b) a control gene. For example, in some embodiments, the control gene is GAPDH and the predetermined threshold value is selected from the group consisting of: (a) a ratio of CNTNAP5 to GAPDH expression of less than about 0.12; (b) a ratio of KLHL1 to GAPDH expression of less than about 0.10; (c) a ratio of NHLH2 to GAPDH expression of less than about 0.56; (d) a ratio of GREM2 to GAPDH expression of less than about 0.35; (e) a ratio of BRINP2 to GAPDH expression of less than about 0.97; (f) a ratio of GRIN3A to GAPDH expression of less than about 0.48; (g) a ratio of LRRC4C to GAPDH expression of less than about 0.39; (h) a ratio of IRX3 to GAPDH expression of less than about 0.55; (i) a ratio of CPNE4 to GAPDH expression of less than about 0.28; (j) a ratio of PTPN3 to GAPDH expression of less than about 0.25; (k) a ratio of PMEL to GAPDH expression of less than about 0.29; (1) a ratio of PCDH20 to GAPDH expression of less than about 0.20; (m) a ratio of LRRC37A2 to GAPDH expression of less than about 0.68; (n) a ratio of TMEM246 to GAPDH expression of less than about 0.53; (o) a ratio of B3GALNT1 to GAPDH expression of less than about 0.67; (p) a ratio of ZHX1 to GAPDH expression of less than about 0.55; (q) a ratio of BCAS4 to GAPDH expression of greater than about 0.42; (r) a ratio of SLC25A37 to GAPDH expression of greater than about 0.38; (s) a ratio of GRINA to GAPDH expression of greater than about 0.60; (t) a ratio of MID1 to GAPDH expression of greater than about 0.62; (u) a ratio of FRMD4A to GAPDH expression of greater than about 0.57; (v) a ratio of PARP10 to GAPDH expression of greater than about 0.25; (w) a ratio of WHAMMP2 to GAPDH expression of greater than about 0.37; (x) a ratio of EYA1 to GAPDH expression of greater than about 0.32; (y) a ratio of CORO2B to GAPDH expression of greater than about 0.40; (z) a ratio of WHAMMP3 to GAPDH expression of greater than about 0.34; (aa) a ratio of B3GALT5 to GAPDH expression of greater than about 0.40; (ab) a ratio of GPR35 to GAPDH expression of greater than about 0.19; (ac) a ratio of ABCD2 to GAPDH expression of greater than about 0.35; (ad) a ratio of ITIH3 to GAPDH expression of greater than about 0.17; (ae) a ratio of AC107464.1 to GAPDH expression of greater than about 0.20; (af) a ratio of CAMK2N1 to GAPDH expression of greater than about 0.52; (ag) a ratio of CAMK2A to GAPDH expression of greater than about 0.37; (ah) a ratio of PRPS1 to GAPDH expression of greater than about 0.52; (ai) a ratio of GOLGA6L10 to GAPDH expression of greater than about 0.21; (aj) a ratio of AMOT to GAPDH expression of greater than about 0.50; (ak) a ratio of SULT1A1 to GAPDH expression of greater than about 0.18; (al) a ratio of CD83 to GAPDH expression of greater than about 0.29; (am) a ratio of SPON1 to GAPDH expression of greater than about 0.76; (an) a ratio of FRMPD3 to GAPDH expression of greater than about 0.31; (ao) a ratio of AC096570.1 to GAPDH expression of greater than about 0.14; (ap) a ratio of TCAF2 to GAPDH expression of greater than about 0.30; (aq) a ratio of GOLGA8M to GAPDH expression of greater than about 0.003; (ar) a ratio of VWA5B2 to GAPDH expression of greater than about 0.22; (as) a ratio of CA8 to GAPDH expression of greater than about 0.19; (at) a ratio of AC017050.1 to GAPDH expression of greater than about 0.08; (au) a ratio of KRT77 to GAPDH expression of greater than about 0.14; (av) a ratio of AP000350.6 to GAPDH expression of greater than about 0.31; (aw) a ratio of LINC02751 to GAPDH expression of greater than about 0.19; and (ax) a ratio of ARHGAP5-AS1 to GAPDH expression of greater than about 0.26.

In some embodiments, the predetermined threshold value is selected from the group consisting of: the predetermined threshold value is selected from the group consisting of: (i) a ratio of CNTNAP5 to GAPDH expression of less than about 0.12; (ii) a ratio of NHLH2 to GAPDH expression of less than about 0.56; (iii) a ratio of GREM2 to GAPDH expression of less than about 0.35; (iv) a ratio of PMEL to GAPDH expression of less than about 0.29; (v) a ratio of PCDH20 to GAPDH expression of less than about 0.20; (vi) a ratio of LRRC37A2 to GAPDH expression of less than about 0.68; (vii) a ratio of SLC25A37 to GAPDH expression of greater than about 0.38; (viii) a ratio of MID1 to GAPDH expression of greater than about 0.62; (ix) a ratio of EYA1 to GAPDH expression of greater than about 0.32; (x) a ratio of B3GALT5 to GAPDH expression of greater than about 0.40; (xi) a ratio of GPR35 to GAPDH expression of greater than about 0.19; (xii) a ratio of AC107464.1 to GAPDH expression of greater than about 0.20; (xiii) a ratio of CAMK2N1 to GAPDH expression of greater than about 0.52; (xiv) a ratio of CAMK2A to GAPDH expression of greater than about 0.37; (xv) a ratio of GOLGA6L10 to GAPDH expression of greater than about 0.21; (xvi) a ratio of FRMPD3 to GAPDH expression of greater than about 0.31; (xvii) a ratio of VWA5B2 to GAPDH expression of greater than about 0.22; (xviii) a ratio of AC017050.1 to GAPDH expression of greater than about 0.08; and (xix) a ratio of LINC02751 to GAPDH expression of greater than about 0.19. In some embodiments, the predetermined threshold value is selected from at least two, three, four, five, six, seven, eight, nine or ten ratios from among (i) to (xix).

In some embodiments, the predetermined first threshold levels values are selected from: a ratio of SLC25A37 to GAPDH expression of greater than about 0.38; and/or a ratio of GPR35 to GAPDH expression of greater than about 0.19; and/or a ratio of CAMK2N1 to GAPDH expression of greater than about 0.52.

In some embodiments, the predetermined first threshold values are: a ratio of a ratio of SLC25A37 to GAPDH expression of greater than about 0.38; a ratio of GPR35 to GAPDH expression of greater than about 0.19; and a ratio of CAMK2N1 to GAPDH expression of greater than about 0.52.

In some embodiments, the invention provides methods of training a machine learning model for predicting whether neuronal cells derived from a population of neuronal progenitor cells will produce dopamine. These methods can include: (a) obtaining gene expression levels for one or more genes in each of a plurality of reference populations of neuronal progenitor cells; (b) receiving dopamine production information for neuronal cells derived from each of the plurality of reference populations, wherein the dopamine production information of a reference population indicates whether or not, or the degree to which, cells derived from the neuronal progenitor cells produced dopamine; and (c) applying the gene expression levels of (a) and applying the dopamine production information of (b) as input to train a machine learning model, wherein the machine learning model is trained to predict based on the gene expression levels of the plurality of genes if neuronal cells derived from a population of neuronal progenitor cells will produce dopamine.

Potency Assay Matrix

In some embodiments, the methods provided by the invention can aid selecting particular lots of in vitro neuronal progenitor cells that are likely to have efficacy in treating neurodegenerative diseases such as Parkinson's Disease. In some embodiments, the provided methods for predicting successful engraftment and dopamine production can be used as part of a potency assay matrix. In some embodiments, the potency assay matrix can also include additional assays.

In some embodiments, the methods include, in addition to testing for predicted engraftment capability and/or dopamine production, assessing whether a cell population has a desired differentiation state, e.g., the differentiation state of a neuronal progenitor cell, such as a determined dopaminergic neuronal progenitor cell. In some embodiments, these methods include any method as described in PCT/US2020/043627 entitled "METHODS OF IDENTIFYING DOPAMINERGIC NEURONS AND PROGENITOR CELLS," PCT/US2022/073974 entitled "METHODS OF DIFFERENTIATING NEURAL CELLS AND PREDICTING ENGRAFTMENT THEREOF," and US Patent Publication 2023/0377685 entitled "METHODS OF CLASSIFING THE DIFFERENTIATION STATE OF CELLS AND RELATED COMPOSITIONS OF DIFFERENTIATED CELLS," which are each incorporated by reference in their entirety.

In some embodiments, the invention provides a potency assay matrix for determining potency of a population of neuronal progenitor cells for treatment of a neurodegenerative disease. The potency assay matrix includes subjecting the population of neuronal progenitor cells to a method that includes at least two of the following steps (a), (b) and (c):

(a) Desired differentiation state: classifying an in vitro population of neuronal progenitor cells to determine whether the neural progenitor cells comprise determined dopaminergic precursor cells by: (i) receiving as input a test dataset that comprises expression levels for one or more genes that are expressed in a first test sample that comprises the neuronal progenitor cells; (ii) calculating a first similarity score for the first test sample using the test dataset and a first reference dataset, wherein: (1) the first reference dataset comprises a representation of gene expression levels for one or more genes that are differentially expressed between cells at a first differentiation state and cells at a second differentiation state, wherein the second differentiation state is that of a determined dopaminergic neuronal cell, and wherein the first differentiation state is earlier or later in a stem cell differentiation pathway than the second differentiation state; (2) the expression levels in the test dataset comprise expression levels for one or more of the genes for which a representation of expression levels are included in the first reference dataset, and (3) the first similarity score indicates whether the differentiation state of the test cells is more similar to the first differentiation state or to the second differentiation state; (iii) determining a novelty score for the neuronal progenitor cells in the first test sample, wherein the novelty score indicates the degree to which the gene expression levels in the test dataset deviate from gene expression levels in the reference database; and (iv) determining, based on the similarity score and the novelty score, whether the first test sample comprises determined dopaminergic neuronal cells;

(b) Engraftment: predicting whether the neuronal progenitor cells are likely to successfully engraft when implanted into a brain region by: (i) determining a gene expression level for one or more genes associated with predicted engraftment potential (G genes) in a second test sample that comprises the neuronal progenitor cells, wherein the one or more G genes are selected from the group consisting of: AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; and (ii) predicting the neuronal engraftment capability of the neuronal progenitor cells by correlating the determined gene expression level of the one or more G genes in the second test sample with a reference plot for each G gene that associates graft size with gene expression levels of the G gene in a training set that comprises one or more reference samples; and (c) Dopamine production: predicting whether neuronal cells derived from the population of neuronal progenitor cells will produce dopamine by: (i) determining a gene expression level for one or more gene associated with predicted dopamine production (D genes) in a third test sample that comprises a population of neuronal progenitor cells, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; and (ii) predicting the dopamine production capability of neuronal cells derived from the neuronal progenitor cells by correlating the determined gene expression level of the one or more D genes in the third test sample with a reference plot for each D gene that associates dopamine production by the neuronal cells with gene expression levels of the D gene in a training set that comprises one or more reference samples of neuronal progenitor cells.

In some embodiments, the potency matrix assay includes at least two of: (a) predicting successful engraftment, (b) predicting dopamine production, and (c) determining the differentiation state, of a population of neuronal progenitor cells to determine the suitability of the population of neuronal progenitor cells for therapeutic use. In some embodiments, the potency assay matrix includes methods (a) and (b). In some embodiments, the potency assay matrix includes methods (a) and (c). In some embodiments, the potency assay matrix includes methods (b) and (c). And in some embodiments, the potency assay matrix includes all three of (a), (b) and (c).

In some embodiments, the potency assay matrix includes step (b) and the G genes are selected from the group consisting of TTR, PRR16, CMTM8, APOA1, CD47, CD01, KIR26A and CNTN2. In some embodiments, the one or more G genes are TTR, PRR16 and CD47.

In some embodiments, the potency assay matrix includes step (c) and the one or more D genes are selected from the group consisting of CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the one or more D genes are B3GALT5, FRMPD3, and GREM2.

In some embodiments, the methods relate to methods of determining expression levels of both G genes and D genes to thereby identify neuronal progenitor cells that are predicted to result in cells that are capable of both engraftment and dopamine production. In some embodiments, the gene expression levels of the G gene and D genes are associated with the ability of the population of neuronal progenitor cells to successfully form grafts following implantation of the population of neuronal progenitor cells in the brain region of a subject, and to produce neuronal cells that can produce dopamine, respectively. In some embodiments, a population of neuronal progenitor cells is selected for implantation based on the gene expression levels of one or more of the G genes and one or more of the D genes.

In some embodiments, the methods can be carried out by any methods that is able to assess gene expression levels. In some embodiments, the methods relate to PCR analysis (e.g., qPCR) of one or more genes (e.g., G genes and/or D genes) in a population of neuronal progenitor cells. In some embodiments, the methods relate to RNAseq analysis of one or more genes (e.g., G genes and/or D genes) in a population of neuronal progenitor cells. In some embodiments, one or more G genes and one or more D genes are assessed by the methods. In some embodiments, 2, 3, 4, 5, 6, 7, 8, 9, 10, 11, 12, 13, 14, 15, 16, 17, 18, 19, 20 or more genes are assessed. In some embodiments, the provided methods relate to a PCR-based method for the assessment of 2, 3, 4, 5 or 6 genes. In some embodiments, the PCR can be a multi-plexed PCR. In some embodiments, the PCR can further include gene expression levels of a housekeeping gene (e.g., GAPDH) to facilitate normalization of the gene expression levels. In some embodiments, gene expression levels, such as by RNAseq analysis, of a test sample can be carried out and the expression levels can be provided in a dataset as input to a process configured to carry out the prediction by a machine learning model trained using gene expression levels for the respective genes. In some embodiments, the process is configured to predict whether neuronal cells derived from the neuronal progenitor cells are likely to engraft in a brain region of a subject following implantation of the population of neuronal progenitor cells in the brain region, wherein the machine learning model is trained using gene expression levels of the G genes for a plurality of reference populations of neuronal progenitor cells. In some embodiments, the process is configured to predict whether neuronal cells derived from the neuronal progenitor cells are capable of dopamine production such as following implantation of the population of neuronal progenitor cells in the brain region, wherein the machine learning model is trained using gene expression levels of the D genes for a plurality of reference populations of neuronal progenitor cells. In some embodiments, the process can be configured to predict both capability of engraftment and dopamine production based on the G genes and D genes, respectively.

Machine Learning Models and Computing Devices

Exemplary Machine Learning Models

In some embodiments, the provided methods include predicting if a population of neuronal progenitor cells has a characteristic associated with a function, activity or differentiation state. In some embodiments, the predicting is by applying gene expression levels of a plurality of genes for one or more cells of the population of neuronal progenitor cells as input to a process configured to predict if the population of neuronal progenitor cells will or neuronal cells derived from such cells has the function, activity or differentiation state. In some embodiments, the process includes a machine learning model. In some embodiments, the process, e.g., machine learning model, is trained using gene expression levels of one or more of the plurality of genes for a plurality of reference populations of neuronal progenitor cells. In some embodiments, the process, e.g., machine learning model, is trained also using information about fitness of cells of the plurality of reference populations for the particular characteristic.

Various machine learning models are suitable for use in accord with the provided methods based on gene expression levels and are within the scope of the disclosure. Machine learning models that can be used in accordance with the provided methods include supervised, unsupervised, and semi-supervised machine learning models. In some embodiments, the process, e.g., machine learning model, is or includes a supervised machine learning model. In some embodiments, the process, e.g., machine learning model, is or includes an unsupervised machine learning model. In some embodiments, the process, e.g., machine learning model, is or includes a semi-supervised machine learning model. In some embodiments, the process, e.g., machine learning model, includes performance of one or more data preprocessing techniques. In some embodiments, the process, e.g., machine learning model, includes performance of one or more dimensionality reduction methods. In some examples, the machine learning approach comprises a classical machine learning method, such as, but not limited to, support vector machine (SVM) (e.g., one-class SVM, linear or radial kernels, etc.), K-nearest neighbor (KNN), isolation forest, random forest, logistic regression, AdaBoost classifier, extra trees classifier, extreme gradient boosting, gaussian process classifier, gradient boosting classifier, light gradient boosting, linear discriminant analysis, naïve Bayes, quadratic discriminant analysis, ridge classifier, or any combination thereof. In some examples, the machine learning approach comprises a deep leaning method (e.g., deep neural network (DNN)), such as, but not limited to a fully-connected network, convolutional neural network (CNN) (e.g., one-class CNN), recurrent neural network (RNN), transformer, graph neural network (GNN), convolutional graph neural network (CGNN), multi-level perceptron (MLP), or any combination thereof.

Any suitable method for training the machine learning models can be used, including any as described in Hastie et al. (2016) *The Elements of Statistical Learning*; and Abu-Mostafa et al. (2012) Learning from Data (2012). Exemplary machine learning models are also described in Hastie et al. (2016) *The Elements of Statistical Learning*; and Abu-Mostafa et al. (2012) *Learning from Data*.

In some embodiments, a classical ML method comprises one or more algorithms that learns from existing observations (i.e., known features) to predict outputs. In some embodiments, the one or more algorithms perform clustering of data. In some examples, the classical ML algorithms for clustering comprise K-means clustering, mean-shift clustering, density-based spatial clustering of applications with noise (DBSCAN), expectation-maximization (EM) clustering (e.g., using Gaussian mixture models (GMM)), agglomerative hierarchical clustering, or any combination thereof. In some embodiments, the one or more algorithms perform classification of data. In some examples, the classical ML algorithms for classification comprise logistic regression, naïve Bayes, KNN, random forest, isolation forest, decision trees, gradient boosting, support vector machine (SVM), or any combination thereof. In some examples, the SVM comprises a one-class SMV or a multi-class SVM. Classical ML methods may be preferable for small to medium datasets due to greater interpretability, while deep learning models may be preferred for larger datasets due to their ability to capture complex patterns.

In some embodiments, the process, e.g., machine learning model, is or includes a regression model. In some embodiments, the process, e.g., machine learning model, is or includes a classification model. In some embodiments, the process, e.g., machine learning model, is or includes a binary classification model. In some embodiments, the process, e.g., machine learning model, is or includes a multiclass classification model.

In some embodiments, the process, e.g., machine learning model, is or includes a logistic regression model. In some embodiments, the process, e.g., machine learning model, is or includes a linear regression model. In some embodiments, the process, e.g., machine learning model, is or includes a multiple linear regression model. In some embodiments, the process, e.g., machine learning model, is or includes a polynomial regression model. In some embodiments, the process, e.g., machine learning model, is or includes a quantile regression model. In some embodiments, the process, e.g., machine learning model, is or includes a principal components regression model. In some embodiments, the process, e.g., machine learning model, is or includes a partial least regression model. In some embodiments, the process, e.g., machine learning model, is or includes a support vector regression model. In some embodiments, the process, e.g., machine learning model, is or includes an ordinal regression model. In some embodiments, the process, e.g., machine learning model, is or includes a Poisson regression model. In some embodiments, the process, e.g., machine learning model, is or includes a negative binomial regression model. In some embodiments, the process, e.g., machine learning model, is or includes a quasi Poisson regression model. In some embodiments, the process, e.g., machine learning model, is or includes a linear discriminant analysis (LDA) model. In some embodiments, the process, e.g., machine learning model, is or includes a Naïve Bayes classifier. In some embodiments, the process, e.g., machine learning model, is or includes a perceptron. In some embodiments, the process, e.g., machine learning model, is or includes a support vector machine (SVM). In some embodiments, the process, e.g., machine learning model, is or includes a quadratic classifier. In some embodiments, the process, e.g., machine learning model, is or includes a decision tree. In some embodiments, the process, e.g., machine learning model, is or includes a random forest. In some embodiments, the process, e.g., machine learning model, is or includes a neural network. In some embodiments, the process, e.g., machine learning model, is or includes an ensemble model comprising any of the foregoing models.

In some embodiments, the process, e.g., machine learning model, is or includes a penalized machine learning model. A penalized machine learning model is one in which coefficient estimates are regularized or constrained towards zero. In some embodiments, the process, e.g., machine learning model, is or includes a ridge regression model. In some embodiments, the process, e.g., machine learning model, is or includes a lasso regression model. In some embodiments, the process, e.g., machine learning model, is or includes an elastic net regression model. In some embodiments, the process, e.g., machine learning model, is or includes a lasso logistic regression model.

In some embodiments, the process, e.g., machine learning model, is or includes a clustering method. In some embodiments, the process, e.g., machine learning model, is or includes a connectivity-based clustering method. In some embodiments, the process, e.g., machine learning model, is or includes hierarchical clustering. In some embodiments, the process, e.g., machine learning model, is or includes a centroid-based clustering method. In some embodiments, the process, e.g., machine learning model, is or includes k-means clustering. In some embodiments, the process, e.g., machine learning model, is or includes a distribution-based clustering method. In some embodiments, the process, e.g., machine learning model, is or includes Gaussian mixture modeling. In some embodiments, the process, e.g., machine learning model, is or includes a density-based clustering method. In some embodiments, the process, e.g., machine learning model, is or includes DBSCAN. In some embodiments, the process, e.g., machine learning model, is or includes OPTICS. In some embodiments, the process, e.g., machine learning model, is or includes a grid-based clustering method. In some embodiments, the process, e.g., machine learning model, is or includes STING. In some embodiments, the process, e.g., machine learning model, is or includes CLIQUE.

In some embodiments, the process, e.g., machine learning model, is or includes factor analysis. In some embodiments, the process, e.g., machine learning model, is or includes network component analysis. In some embodiments, the process, e.g., machine learning model, is or includes linear discriminant analysis. In some embodiments, the process, e.g., machine learning model, is or includes independent component analysis (ICA). In some embodiments, the process, e.g., machine learning model, is or includes principal component analysis (PCA). In some embodiments, the process, e.g., machine learning model, is or includes sparse PCA. In some embodiments, the process, e.g., machine learning model, is or includes robust PCA.

In some embodiments, the process, e.g., machine learning model, is or includes non-negative matrix factorization (NMF). In some embodiments, the process, e.g., machine learning model, is or includes conventional NMF. In some embodiments, the process, e.g., machine learning model, is or includes discriminant NMF. In some embodiments, the process, e.g., machine learning model, is or includes regularized NMF. In some embodiments, the process, e.g., machine learning model, is or includes graph regularized NMF. In some embodiments, the process, e.g., machine learning model, is or includes bootstrapping sparse NMF.

In some embodiments, the process, e.g., machine learning model, is or includes kernel PCA. In some embodiments, the process, e.g., machine learning model, is or includes generalized discriminant analysis (GDA). In some embodiments, the process, e.g., machine learning model, is or includes an autoencoder. In some embodiments, the process, e.g., machine learning model, is or includes T-distributed Stochastic Neighbor Embedding (t-SNE). In some embodiments, the process, e.g., machine learning model, is or includes a manifold learning technique. In some embodiments, the process, e.g., machine learning model, is or includes Isomap. In some embodiments, the process, e.g., machine learning model, is or includes locally linear embedding (LLE). In some embodiments, the process, e.g., machine learning model, is or includes Hessian LLE. In some embodiments, the process, e.g., machine learning model, is or includes Laplacian eigenmaps. In some embodiments, the process, e.g., machine learning model, is or includes graph-based kernel PCA. In some embodiments, the process, e.g., machine learning model, is or includes uniform manifold approximation and projection (UMAP).

In some embodiments, in connection with the methods for classifying by prediction the differentiation state of neuronal cells, the machine learning models of the first and second reference datasets are the same type of machine learning model, e.g., are both logistic regression models. In some embodiments, the machine learning models of the first and second reference datasets are different types of machine learning models, e.g., one logistic regression model and one support vector machine classifier. Similarly, the first and second machine learning models trained according to any of the provided methods can be the same or different types of machine learning models.

In some embodiments, the machine learning model includes an ensemble model that includes a plurality of any combination of any of the foregoing models. Ensemble model techniques such as model stacking and boosting can improve prediction accuracy by combining the strengths of different models, particularly in cases of heterogeneous gene expression data.

In some embodiments, the methods include selecting based on an output of the process, e.g., machine learning model, the population of neuronal progenitor cells as a population of neuronal progenitor cells that have the desired predicted characteristic.

Computing Devices

The present disclosure provides computer systems that are programmed to implement methods of the disclosure.

In some embodiments, the invention provides computing device configured to predict the engraftment potential of a population of neuronal progenitor cells when the neuronal progenitor cells are implanted into a brain region, the computing device comprising: (a) a processor; (b) a memory comprising instructions executable by the processor, the instructions configured to execute the steps of: (i) receiving a test sample that includes gene expression data for one or more genes associated with predicted engraftment potential (G genes) in a population of neuronal progenitor cells, wherein the one or more G genes are selected from the group consisting of AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2; (ii) determining, based on the test sample, a gene expression level for each of the one or more G genes; (iii) comparing the determined gene expression level for each of the one or more G genes in the test sample to a reference plot for each respective G gene, wherein each reference plot correlates gene expression levels of the G gene with graft size data obtained from a training set comprising one or more reference samples; and (iv) predicting the neuronal engraftment capability of the neuronal progenitor cells in the test sample by correlating the determined gene expression levels of the one or more G genes in the test sample with the reference plot data, thereby generating a predictive assessment of engraftment potential for the population of neuronal progenitor cells.

Figure 4:
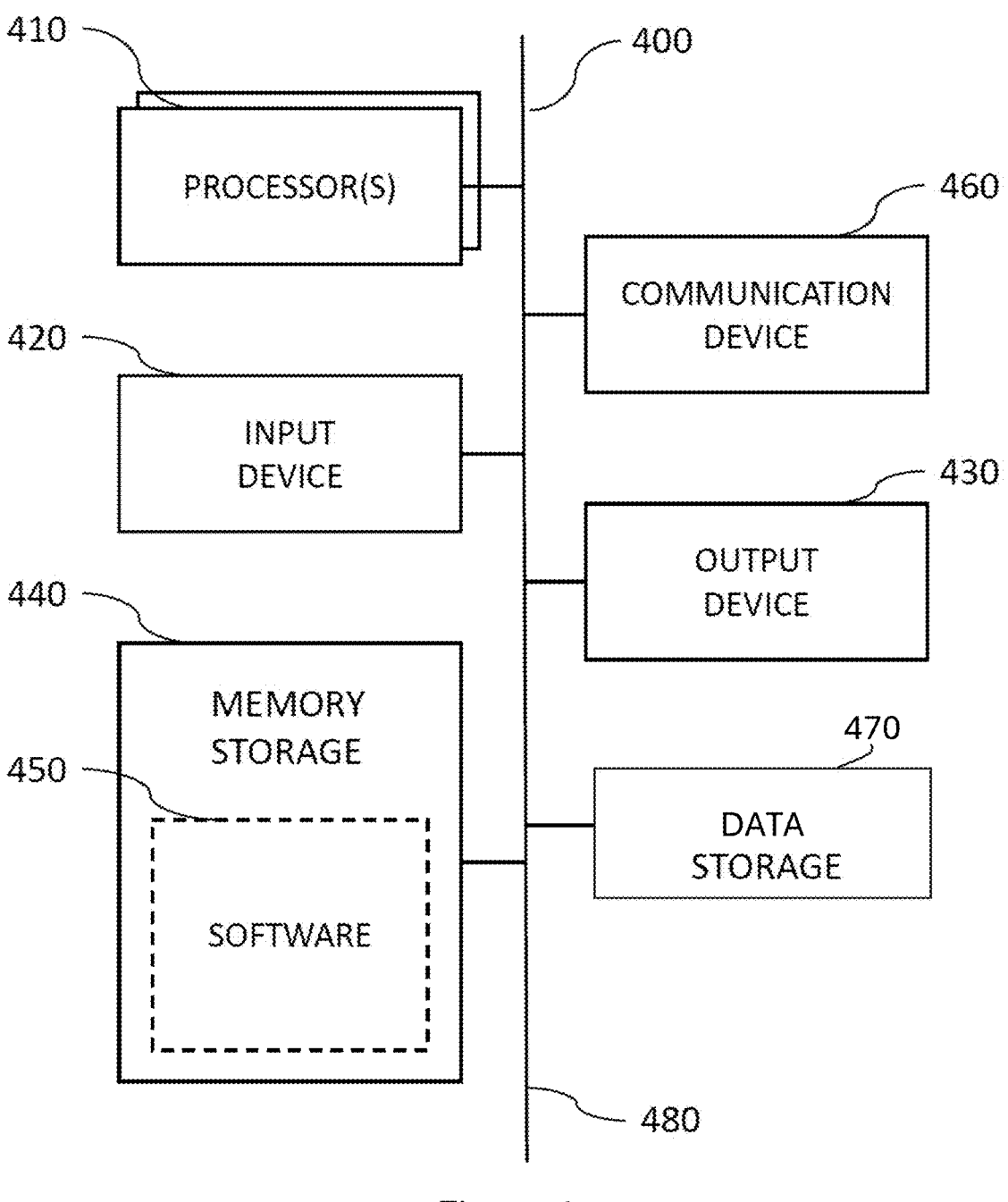
FIG. 4 depicts an exemplary computing device or system, in accordance with some embodiments of the present disclosure.
Figure 5:
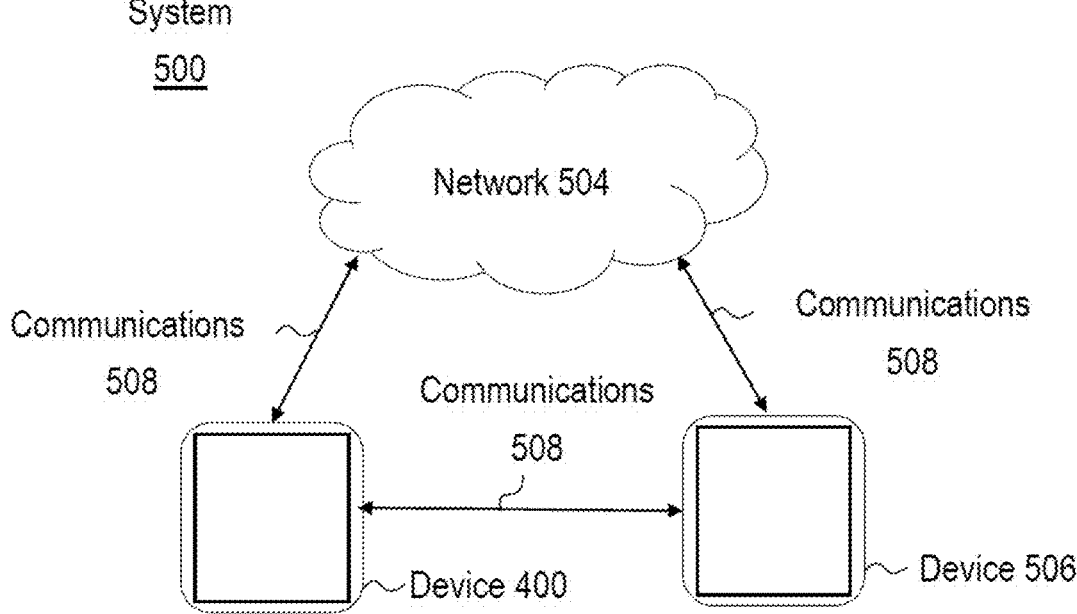
FIG. 5 depicts an exemplary computer system or computer network, in accordance with some instances of the systems described herein.

In some embodiments, the invention provides a computing device configured to predict whether neuronal cells differentiated from a population of neuronal progenitor cells will produce dopamine. The computing device includes: (a) a processor; (b) a memory comprising instructions executable by the processor, the instructions configured to execute the steps of: (i) receiving a test sample that includes gene expression data for one or more genes associated with predicted dopamine production potential (D genes) in a population of neuronal progenitor cells, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1; (ii) determining, based on the test sample, a gene expression level for each of the one or more D genes; (iii) comparing the determined gene expression level for each of the one or more D genes in the test sample to a reference plot for each respective D gene, wherein each reference plot correlates gene expression levels of the D gene with dopamine production levels obtained from a training set comprising one or more reference samples; and (iv) predicting the dopamine production capability of neuronal cells derived from the neuronal progenitor cells in the test sample by correlating the determined gene expression levels of the one or more D genes with the reference plot data, thereby generating a predictive assessment of dopamine production potential for the derived neuronal cells FIG. 4 shows one example of a computer system that is programmed or otherwise configured to perform the methods described herein for characterizing populations of neuronal progenitor cells. The computer system includes a central processing unit (CPU, also "processor" and "computer processor" herein) 410, which can be a single core or multi core processor, or a plurality of processors for parallel processing. The computer system also includes memory or memory location 440 (e.g., random-access memory, read-only memory, flash memory), communication interface 460 (e.g., network adapter) for communicating with one or more other systems, and peripheral devices 430, such as cache, other memory, data storage and/or electronic display adapters. The memory 440, interface 460 and peripheral devices 430 are in communication with the CPU 410 through a communication bus (solid lines), such as a motherboard. The storage unit 470 can be a data storage unit (or data repository) for storing data. The computer system can be operatively coupled to a computer network ("network") 504 (FIG. 5) with the aid of the communication interface 460. The network 504 can be the Internet, an internet and/or extranet, or an intranet and/or extranet that is in communication with the Internet. The network 504 in some cases is a telecommunication and/or data network. The network 504 can include one or more computer servers, which can enable distributed computing, such as cloud computing. The network 504, in some cases with the aid of the computer system, can implement a peer-to-peer network, which may enable devices coupled to the computer system to behave as a client or a server.

The CPU 410 can execute a sequence of machine-readable instructions, which can be embodied in a program or software. The instructions may be stored in a memory location, such as the memory 440. The instructions can be directed to the CPU 410, which can subsequently program or otherwise configure the CPU 410 to implement methods of the present disclosure. Examples of operations performed by the CPU 410 can include fetch, decode, execute, and writeback.

The CPU 410 can be part of a circuit, such as an integrated circuit. One or more other components of the system can be included in the circuit. In some cases, the circuit is an application specific integrated circuit (ASIC).

A graphics processing unit (GPU) is a specialized processing unit, electronic circuit, module, or computer chip, etc., that can accelerate many applications, and is often present either as a discrete video card, or embedded on motherboards, or as integrated graphics on a CPU. Similarly, chip modules are known that can perform machine learning prediction (sometimes referred to as inference). Such chips include, for example, language processing units (LPUs), cloud tensor processing units (TPUs), neural engines, AI coprocessors, AI accelerators, and neural processing units (NPUs). In some embodiments, a GPU or other chip module performs at least some of the functions that could otherwise be performed by a CPU.

The storage unit 470 can store files, such as drivers, libraries and saved programs. The storage unit can store user data, e.g., user preferences and user programs. The computer system in some cases can include one or more additional data storage units 470 that are external to the computer system, such as located on a remote server that is in communication with the computer system through an intranet or the Internet. In some embodiments, the computing device includes a memory that includes a provided dataset of gene expression levels. In some embodiments, the dataset is a reference dataset from one or more reference populations of neuronal progenitor cells. In some embodiments, the dataset is a dataset of expression levels of G genes from one or more reference neuronal progenitor cell populations. In some embodiments, the dataset is a dataset of expression levels of D genes from one or more reference neuronal progenitor cell populations. In some embodiments, the memory further includes one or more additional reference datasets. In some embodiments, the one or more additional reference datasets include any of the first and second reference datasets described herein. In some embodiments, the memory further includes a control dataset as described herein.

The computer system can communicate with one or more remote computer systems through the network 504. For instance, the computer system can communicate with a remote computer system of a user (e.g., a lab technician who is formulating neuronal progenitor cells for therapeutic use). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system via the network 504.

Methods as described herein can be implemented by way of machine (e.g., computer processor) executable code stored on an electronic storage location of the computer system, such as, for example, on the memory 440 or electronic storage unit 470. The machine executable or machine readable code can be provided in the form of software. During use, the code can be executed by the processor 410. In some cases, the code can be retrieved from the storage unit 470 and stored on the memory 440 for ready access by the processor 410. In some situations, the electronic storage unit can be precluded, and machine-executable instructions are stored on memory 440.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk 470. "Storage" type media 470 can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system can include or be in communication with an electronic display that comprises a user interface (UI) 430 for providing, for example, evaluation of a population of neuronal progenitor cells. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 410. The algorithm can, for example, automatically characterize populations of neuronal progenitor cells with respect to their likelihood of successfully engrafting when implanted into the brain of a subject, to give rise to neuronal cells that produce dopamine, and/or to determine whether the cells are at a desired differentiation state.

Compositions and Formulations

In embodiments of the provided methods, neuronal progenitor cells identified by the methods provided herein can be harvested or collected, such as for formulation and use as therapeutic agents, such as for use as a cell therapy in the treatment of a neurodegenerative disease. In some embodiments, the dose of cells comprising neuronal progenitor cells (e.g., determined DA neuronal progenitor cells), is provided as a composition or formulation, such as a pharmaceutical composition or formulation. Such compositions can be used in accord with the provided methods, such as in the prevention or treatment of neurodegenerative disorders, including Parkinson's disease.

In some embodiments, the provided methods further include selecting cells that are predicted to result in cells having the capability to engraft and/or to produce dopamine. In some embodiments, the selected population is harvested according to any of the methods described herein. In some embodiments, the harvesting is carried out between about day 13 and about day 20. In some embodiments, the harvesting is carried out at about day 16 or later. In some embodiments, the selected population at harvest is at about day 16 or later of culture. In some embodiments, the harvesting is carried out between about day 18 and about day 24. In some embodiments, the selected population at harvest is at between about day 18 and about day 23 of culture. In some embodiments, the harvesting is carried out at or about at day 18, day 19, day 20, day 21, day 22, or day 23. In some embodiments, the selected population at harvest is at or about at day 18, day 19, day 20, day 21, day 22, or day 23 of culture. In some embodiments, the harvesting is carried out at or about at day 20. In some embodiments, the selected population at harvest is at or about day 20 of culture.

Also provided herein are compositions comprising populations of cells produced or selected according to the provided methods. Also provided herein are methods of treating a subject having a neurodegenerative disease, wherein the subject is treated by implanting any of the provided compositions.

The provided embodiments relate to methods for producing a cell therapy of differentiated neuronal progenitor cells that are suitable for administration to a subject for treating a neurodegenerative disease. In particular embodiments, the methods provided herein improve the ability to produce therapeutic cell compositions of differentiated neuronal progenitor cells that result in cells that are more likely to engraft, such as also innervate, the brain region of a subject with the neurodegenerative disease and/or that are capable of dopamine production. In some particular embodiments, the neurodegenerative disease is Parkinson's disease (PD). In some embodiments, the provided methods address problems related to characteristics of Parkinson's disease (PD), including the selective degeneration of midbrain dopamine (mDA) neurons in patients' brains. Because PD symptoms are primarily due to the selective loss of DA neurons in the substantia nigra of the ventral midbrain, PD is considered suitable for cell replacement therapeutic strategies.

In some embodiments, the provided therapeutic compositions are pharmaceutical compositions containing a pharmaceutically acceptable carrier. In some embodiments, the dose of cells including cells classified by any of the methods disclosed herein is provided as a composition or formulation, such as a pharmaceutical composition or formulation. Such compositions can be used in accord with the provided methods, articles of manufacture, and/or with the provided compositions, such as in the prevention or treatment of diseases, conditions, and disorders, such as neurodegenerative disorders.

In some embodiments, the provided methods further include formulating the harvested cells with a cryoprotectant. In some embodiments, the harvested cells are formulated according to any of the methods described herein. In some embodiments, the provided methods further include cryopreserving the formulated cells. In some embodiments, the formulated cells are cryopreserved according to any of the methods described herein. In some embodiments, the cryopreserving includes controlled rate freezing.

In some cases, the cells are processed in one or more steps for manufacturing, generating or producing a cell therapy and/or differentiated cells may include formulation of cells, such as formulation of differentiated cells resulting from the methods. In some cases, the cells can be formulated in an amount for dosage administration, such as for a single unit dosage administration or multiple dosage administration.

In certain embodiments, one or more compositions of differentiated cells are formulated. In particular embodiments, one or more compositions of differentiated cells are formulated after the one or more compositions have been produced. In some embodiments, the one or more compositions have been previously cryopreserved and stored, and are thawed prior to the administration.

Articles of Manufacture and Kits

In some embodiments, provided herein are kits for carrying out any of the provided methods. In some embodiments, the kit includes one or more primer sets for amplification of a gene (e.g., G gene or D gene) and optionally a probe. In some embodiments, each primer set and the probe is specific for the gene to be amplified.

In some embodiments, provided herein is a kit comprising one or more of pairs of oligonucleotide primers that are useful for predicting engraftment, where each pair of oligonucleotide premiers is specific for a gene selected from the group consisting of AC000120.3, KRT77, TTR, PRR16, MEGF10, PDE3A, GDPD2, CMTM8, APOA1, CMTM7, CDHR3, CORIN, VTN, CPNE8, EFEMP1, CD47, SPARC, JAM2, CDO1, PLXDC2, DYNLL2, ITGA3, RPS6KL1, CHRNB2, SULT4A1, PTPN3, LZTS1, RUNX1T1, TMEM145, EPHA10, CARMIL3, MANEAL, TMEM176B, MPP3, DRAXIN, ADGRB1, KIF26A, CELF5, CNTN2, ASPHD1, SVOP, ANGPT2, SLC22A15, SRRM3, GRIN2D, DACH2, CHST1, GRIN1, LHX5, and NOS2. In some embodiments, the kit includes two pairs of oligonucleotide primers specific for any two of the above genes. In some embodiments, the kit includes three pairs of oligonucleotide primers specific for any two of the above genes. In some embodiments, the kit includes four pairs of oligonucleotide primers specific for any two of the above genes. In some embodiments, the kit includes five pairs of oligonucleotide primers specific for any two of the above genes. In some embodiments, the kit includes six pairs of oligonucleotide primers specific for any two of the above genes. In any of such embodiments, the kit can further include an oligonucleotide probe for each set of primer pairs. In some embodiments, the kit is for predicting engraftment potential of neuronal cells derived from neuronal progenitor cells.

In some embodiments, provided herein is a kit comprising three primer pairs, comprising a first pair of oligonucleotide primers suitable for amplification of a first gene, a second pair of oligonucleotide primers suitable for amplification of a second gene, and a third pair of oligonucleotide primers suitable for amplification of a third gene. In some embodiments, the first gene, the second gene, and the third gene are each selected from the group consisting of: TTR, PRR16, CMTM8, APOA1, CD47, CD01, KIR26A and CNTN2. In some embodiments, the first gene is TTR, the second gene is PRR16, and the third gene is CD47. In any of such embodiments, the kit can further include an oligonucleotide probe for each set of primer pairs. In some embodiments, the kit is for predicting engraftment potential of neuronal cells derived from neuronal progenitor cells.

In some embodiments, provided herein is a kit comprising one or more of pairs of oligonucleotide primers that are useful for predicting dopamine production, where each pair of oligonucleotide premiers is specific for a gene selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1. In some embodiments, the kit includes two pairs of oligonucleotide primers specific for any two of the above genes. In some embodiments, the kit includes three pairs of oligonucleotide primers specific for any two of the above genes. In some embodiments, the kit includes four pairs of oligonucleotide primers specific for any two of the above genes. In some embodiments, the kit includes five pairs of oligonucleotide primers specific for any two of the above genes. In some embodiments, the kit includes six pairs of oligonucleotide primers specific for any two of the above genes. In any of such embodiments, the kit can further include an oligonucleotide probe for each set of primer pairs. In some embodiments, the kit is for predicting dopamine production of neuronal cells derived from neuronal progenitor cells.

In some embodiments, provided herein is a kit comprising three primer pairs, comprising a first pair of oligonucleotide primers suitable for amplification of a first gene, a second pair of oligonucleotide primers suitable for amplification of a second gene, and a third pair of oligonucleotide primers suitable for amplification of a third gene. In some embodiments, the first gene, the second gene, and the third gene are each selected from the group consisting of: CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751. In some embodiments, the first gene is B3GALT5, the second gene is GREM2, and the third gene is FRMPD3. In any of such embodiments, the kit can further include an oligonucleotide probe for each set of primer pairs. In some embodiments, the kit is for predicting engraftment potential of neuronal cells derived from neuronal progenitor cells.

In some embodiments, each of the oligonucleotide primers are operably linked to a detectable marker. In some embodiments, the detectable marker is a fluorescent label.

In some embodiments, the kit further comprises a probe for each pair of oligonucleotide primers. In some embodiments, the probe comprises a reporter dye and a quencher. In some embodiments, the reporter dye of each probe in the kit is different. In some embodiments, the reporter dye is a fluorescent label.

Also provided herein in some embodiments are articles of manufacture that include any of the provided therapeutic compositions. Also provided herein in some embodiments are kits including (i) any of the provided therapeutic compositions and (ii) instructions for administering the therapeutic composition to a subject.

In some embodiments, the articles of manufacture or kits include one or more containers, typically a plurality of containers, packaging material, and a label or package insert on or associated with the container or containers and/or packaging. In some embodiments, the instructions provide directions or specify methods for assessing if a subject, prior to receiving a cell therapy, is likely or suspected of being likely to respond and/or the degree or level of response following administration of cells for treating a disease or disorder. In some aspects, the articles of manufacture can contain a dose or a composition of differentiated cells.

The articles of manufacture provided herein contain packaging materials. Packaging materials for use in packaging the provided materials are well known to those of skill in the art. See, for example, U.S. Pat. Nos. 5,323,907, 5,052,558 and 5,033,252, each of which is incorporated herein in its entirety. Examples of packaging materials include, but are not limited to, blister packs, bottles, tubes, inhalers, pumps, bags, vials, containers, syringes, disposable laboratory supplies, e.g., pipette tips and/or plastic plates, or bottles. The articles of manufacture or kits can include a device so as to facilitate dispensing of the materials or to facilitate use in a high-throughput or large-scale manner, e.g., to facilitate use in robotic equipment. Typically, the packaging is non-reactive with the therapeutic compositions contained therein.

In some embodiments, the compositions are packaged separately. In some embodiments, each container can have a single compartment. In some embodiments, other components of the articles of manufacture or kits are packaged separately, or together in a single compartment.

Methods of Treatment

Provided herein in some embodiments are methods of using any of the provided therapeutic compositions for treating a disease or condition in a subject in need thereof. In some embodiments, the provided methods include implanting a population of neuronal progenitor having one or more desired characteristics into a subject. In some embodiments, a subject has a neurodegenerative disease. In some embodiments, the neurodegenerative disease comprises the loss of dopamine neurons in the brain. In some embodiments, the subject has lost dopamine neurons in the substantia nigra (SN). In some embodiments, the subject has lost dopamine neurons in the substantia nigra pas compacta (SNc). In some embodiments, the subject exhibits rigidity, bradykinesia, postural reflect impairment, resting tremor, or a combination thereof. In some embodiments, the subject exhibits abnormal [18F]-L-DOPA PET scan. In some embodiments, the subject exhibits [18F]-DG-PET evidence for a Parkinson's Disease Related Pattern (PDRP).

In some embodiments, the neurodegenerative disease is Parkinsonism. In some embodiments, the neurodegenerative disease is Parkinson's disease. In some embodiments, the neurodegenerative disease is idiopathic Parkinson's disease. In some embodiments, the neurodegenerative disease is a familial form of Parkinson's disease. In some embodiments, the subject has mild Parkinson's disease. In some embodiments, the subject has a Movement Disorder Society-Unified Parkinson's Disease Rating Scale (MDS-UPDRS) motor score of less than or equal to 32. In some embodiments, the subject has moderate or advanced Parkinson's disease. In some embodiments, the subject has mild Parkinson's disease. In some embodiments, the subject has a MDS-UPDRS motor score of between 33 and 60.

In some embodiments, the dose of cells is administered to the striatum of the subject. In some embodiments, the dose of cells is administered to one hemisphere of the subject's striatum. In some embodiments, the dose of cells is administered to both hemispheres of the subject's striatum. In some embodiments, the dose of cells is between at or about 1 million cells per hemisphere and at or about 30 million cells per hemisphere. In some embodiments, the dose of cells is between at or about 5 million cells per hemisphere and at or about 20 million cells per hemisphere. In some embodiments, the dose of cells is between at or about 10 million cells per hemisphere and at or about 15 million cells per hemisphere.

EXAMPLES

The following examples are included for illustrative purposes only and are not intended to limit the scope of the invention.

Two types of models are described in the following examples. The first is a PCA-based model and the second is a gene-based model. The PCA-based model can be used for predicting graft size from bulk gene expression levels of dopaminergic neuronal progenitor cells (DANPCs), or for predicting the amount of dopamine released by a DANPC in vitro during extended culture, upon addition of KCl. Similarly, the gene-based model can also be used for predicting graft size from bulk gene expression levels of DANPCs, or for predicting the amount of dopamine released by a DANPC in vitro during extended culture, upon addition of KCl. The following examples describe how the two different models can be used to predict graft size or the amount of dopamine released.

Example 1—PCA-Based Model for Predicting Graft Size

Figure 6:
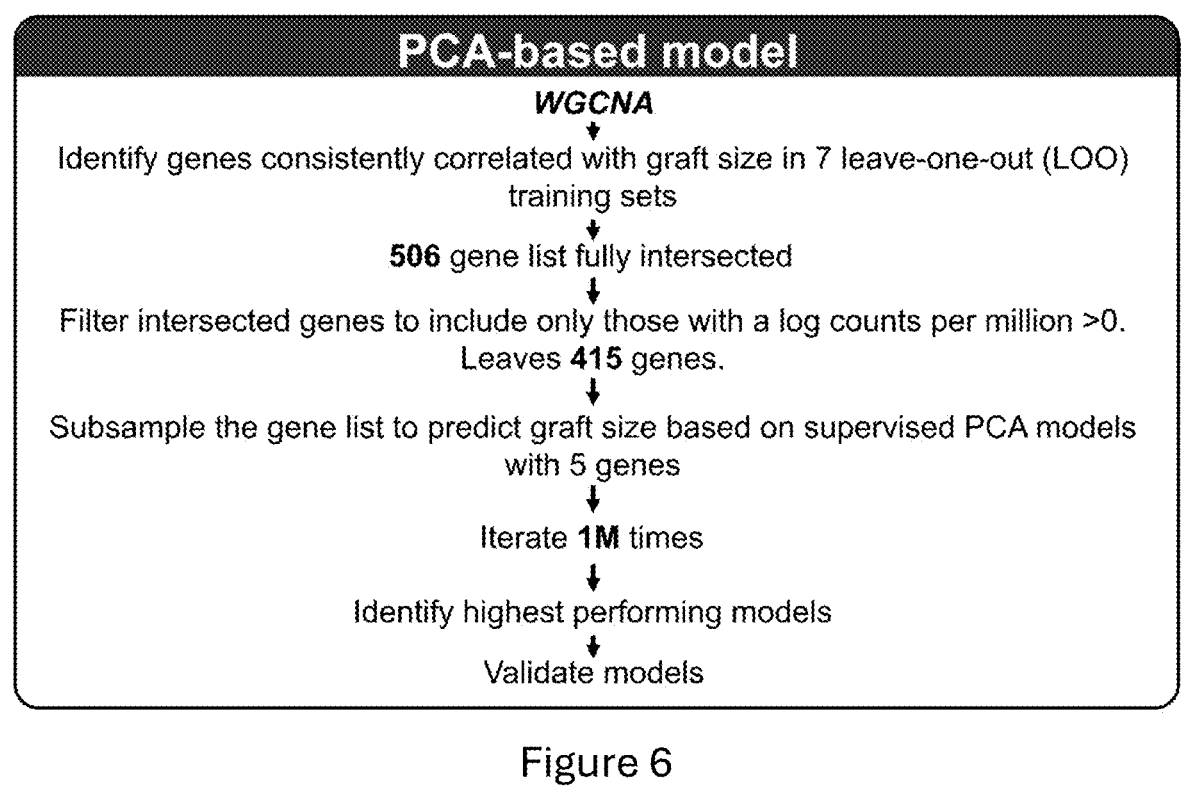

A machine learning method for predicting the outcome of grafting DANPCs, based on gene expression levels of DANPCs, was developed. To do so, bulk gene expression levels from a fraction of cells of a population of human DANPCs differentiated from in vitro pluripotent stem cells (iPSCs) were ascertained. A remaining fraction of cells from the same population of human DANPCs were stereotactically injected, either unilaterally or bilaterally, into the striatum of a rat. The injected DANPCs were then quantified via an image processing software, to derive various features related to the DANPCs' grafting outcomes. Of these grafting outcomes, the graft size of the injected DANPCs were ascertained. Thus, from a given population of human DANPCs, population-specific bulk gene expression levels and a population-specific graft size was obtained. Population-specific bulk gene expression levels and population-specific graft sizes were obtained for DANPC populations deriving from multiple human subjects. The PCA-based model described in the present example used DANPC gene expression levels to predict the graft sizes of injected DANPCs. FIG. 6 depicts a schematic workflow of the PCA-based model for using bulk gene expression data from DANPCs to predict graft size. Of note, the methods described herein need not be limited to predicting the graft size of grafted DANPCs, but can generalize to a) predicting any kind of grafting outcome, such as grafting outcomes that are not graft size, and b) other cell types that are not DANPCs.

The training data and test data used for training and testing the machine learning model included bulk RNA sequencing (RNAseq) data of the DANPCs. The bulk gene expression levels were then correlated against the graft size of the corresponding DANPCs. The strength of the correlations between the graft size and the corresponding DANPCs' RNAseq expression were quantified by metrics, e.g., the Pearson's correlation coefficient, in accordance with the Weighted Correlation Network Analysis (WGCNA) software package in the R programming language.

A. Splitting the Data, by Donor, into Training and Test Fractions

The resulting data regarding the correlations between the bulk RNAseq data and the corresponding DANPCs' graft size were split into a training data fraction and a test data fraction, via a leave-one-out (LOO) methodology, for the same number of iterations as the number of donors represented in the correlation data, e.g., 7 iterations. The LOO method is a type of cross-validation method. The purpose of cross-validation is to control for the undesirable possibility that the training data fraction may not be representative of the variable of interest for prediction, and thus, the model fails to generalize, because the model is trained on unusual data. The training data fraction may, by random chance, comprise a highly unusual composition of data, and training a model based on such an unusual composition may result in a model that does not generalize across all or most instances of the variable of interest for prediction. To limit such artifacts, cross-validation is used. Cross-validation entails generating many pairs of training and test data fractions. In the case of LOO cross-validation, a single data point is reserved as the test data, and the remaining data is considered the training data. In the present example, DANPCs derived from 7 subjects, and thus 7 iterations of LOO were used for cross-validation: 1 subject (e.g., subject A) for test data and the remaining 6 subjects (subjects B-G) for training data; 1 subject (e.g., subject B) for test data and the remaining 6 subjects (subjects A, C-G) for training data . . . 1 subject (e.g., subject G) for test data and the remaining 6 subjects (subjects A-F) for training data. LOO cross-validation is useful in the case where the sample size of independent and individually distributed (IID) random variables is small. The present example considers the relevant sample size to be the number of subjects, unlike many other methods which consider the relevant sample size to be the number of cells to be grafted, e.g., DANPCs. Although using the number of subjects as the relevant sample size will often result in a smaller sample size than if the number of cells were used, opting for the number of subjects as the relevant sample size during cross-validation can result in a machine learning model with improved predictive power. Some methods, however, opt to use the number of cells as the sample size, because doing so often inflates the sample size, and the experimenter may believe that a higher sample size is unconditionally favorable. Methods that use the number of cells to be grafted as the relevant sample size, however, can often lead to a machine learning model with poor predictive power, because in cases where the cells to be grafted derive from common donors, the cells that derive from a common donor are not truly IID-cells from a common donor likely have much more in common than if they were compared to cells from another donor. In addition, by considering the relevant sample size to be the number of subjects, rather than the number of cells to be grafted, splitting of the data into training and test fractions during cross-validation does not result in cells from a given donor to be present in both the training and test fractions. Such a model design choice is especially important when using RNAseq data from donor cells because most of the unique signatures in donor cell RNAseq data is indicative of the idiosyncrasies of the donor subject, rather than being indicative of a more general variable of interest common to most donors, such as a cell grafting outcome, e.g., graft size. For the reasons above, the methods described in the present example opt to use the number of subjects, and not the number of cells for grafting, as the relevant sample size for cross-validation, even though doing so may result in a smaller number of iterations for cross-validation. Accordingly, the cross-validation method used in the present example is limited to a cross-validation method that is compatible with a small sample size, and thus, LOO is used.

B. Performing PCA on Five Randomly Sampled Genes

For each of the seven iterations, LOO was performed on the correlation data (i.e., the correlation data regarding the correlations between a given gene's expression levels from DANPC bulk RNAseq data, and the corresponding DANPCs' graft sizes), the correlation data in the training fraction was ranked, and the top 2000 correlation values were selected from each iteration's training fraction. For each iteration's training fraction, the 2000 genes corresponding to the 2000 correlation values were selected, and the genes that were common to all seven iterations were identified. The genes common to all seven iterations were then filtered for expression levels greater than 0 log counts per million (log CPM). Four hundred fifteen genes were identified to be common to the training fractions of all 7 LOO iterations and survived expression filtering. Of the 415 identified genes, five genes were randomly selected and principal component analysis (PCA) was run on the five genes. The random selecting of five genes from the 415 identified genes, followed by PCA on the 5 randomly selected genes, was done a million times, resulting in a million PCA outcomes (e.g., the percentage of variance of the data explained by each principal component resulting from each PCA, etc.). An $R^2$ value was also determined for each training data fraction used for generating each of the million PCA outcomes (i.e., an $R^2$ value between the RNAseq levels for the 5 selected genes and the corresponding graft size). The result of the 1 million PCAs was a dataset comprising 1 million rows, where each row comprised the corresponding $R^2$ value, and the percentage of variance of the data explained by each principal component (PC) resulting from each PCA. Of note, running the million PCAs represents an aspect of increased computational efficiency, when compared to the complete number of PCAs that would be required for investigating every possible selection of 5 genes from the 415 identified genes. The total number of possible combinations of 5 genes drawn from 415 possible genes is $$\binom{415}{5} = 100,128,170,583$$

possible combinations, and thus, randomly using only one million five-gene sets for PCA, of the 100,128,170,583 possible combinations, saves on roughly six orders of magnitude in computational efficiency. In addition, the selection of using very few genes, e.g., five genes, from the total number of possible 415 genes, controls the otherwise outsized influence that a particular donor subject would have when training the machine learning model, e.g., model derived from the PCAs. If a large number of genes was selected from the total number of possible 415 genes, and PCA was then performed on the large number of genes, most of the variance captured by the PCA would relate not to general grafting outcome, i.e., a grafting outcome common or agnostic to the donor subjects, but rather, would relate mostly to the idiosyncrasies of the particular donor subject. Thus, to avoid overfitting the PCAs onto the training data, only a small number of genes, e.g., five genes, were repeatedly selected from the 415 possible genes.

C. Generating Linear Regression Models from PC1 and Known Graft Sizes

Figure 7:
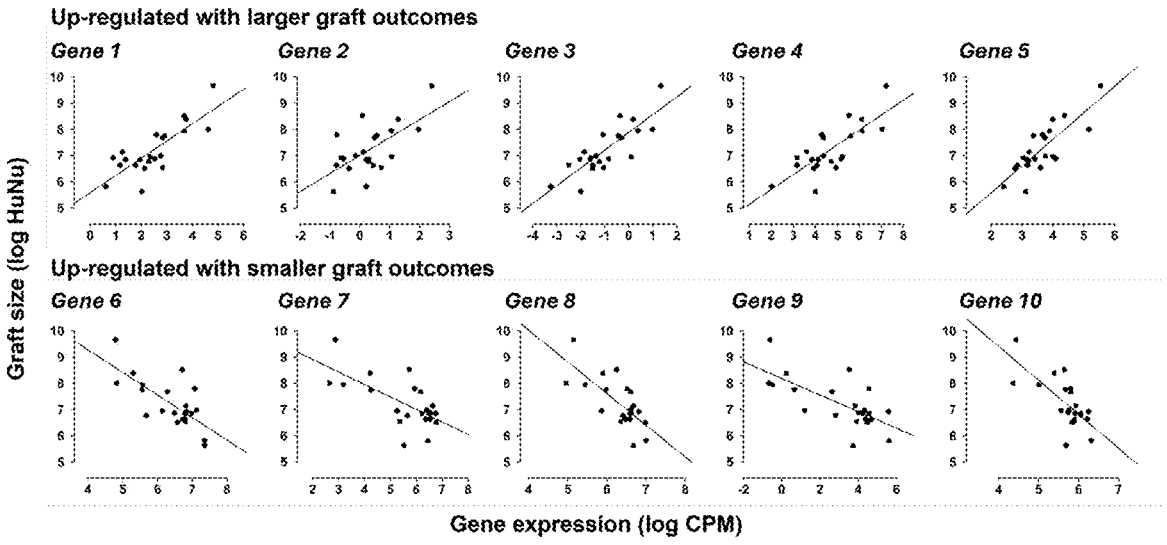
FIG. 7 depicts a non-limiting example of data that depicts five genes (Genes 1-5) for which upregulated expression corresponds to larger predicted graft sizes, and five genes (Genes 6-10) for which upregulated expression corresponds to smaller predicted graft sizes.
Figure 8:
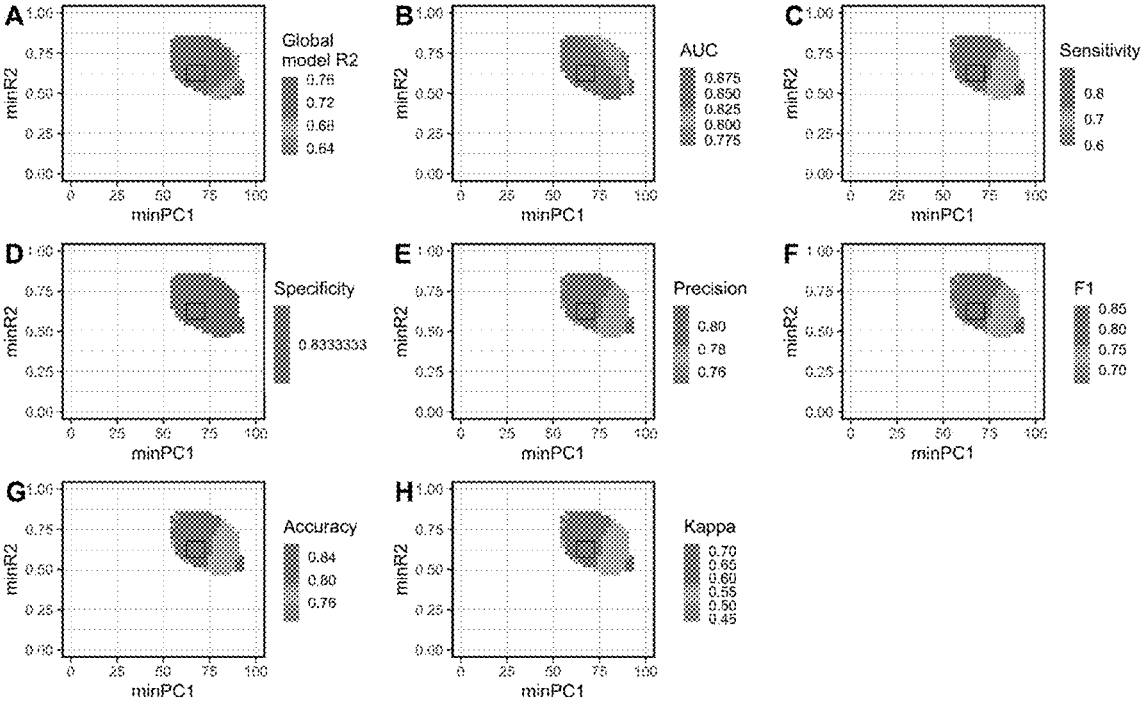
FIGS. 8A-H depict a non-limiting example of data that depicts linear regression models derived from PCA, that are predictive of the size of grafts obtained from a population of neuronal progenitor cells when the neuronal progenitor cells are implanted into a subject brain, based on gene expression levels of the neuronal progenitor cells, wherein the models are organized according to their $R^2$ value and their percentage of variance explained by PC1 (PC1%).

Each row of the 1 million row dataset, which describes the results of a PCA, was used to predict the graft size from the test fraction, via linear regression. Some of the results of each PCA of the 1 million PCAs can be described as a matrix of 22 cell lots×5 PCs, of which only the column vector describing the first PC (i.e., PC1) results are of interest, i.e., 22 cells lots×PC1. The elements of the 22 cells lots×PC1 vector are, more specifically, the projections of the gene expression (e.g., bulk RNAseq) data onto PC1 (i.e., the first set of co-ordinates in PC space). The 22 projections onto PC1 were plotted against the graft sizes of the 22 corresponding cell lots from the training fraction, and linear regression was performed, i.e., a predictive linear model of the form y=mx+b was generated, where y is the predicted graft size. The test data fraction was then inputted into the predictive linear models (informed by the training data fraction) to generate predicted graft sizes. Thus, each PCA corresponds to a set of 5 genes from the possible 506 genes, and a resulting predicted graft size, via a linear relationship. The resulting linear relationship is depicted for 10 genes in FIG. 7, where the x-axis of each plot in FIG. 7 is the gene expression of the gene of interest, and the y-axis of each plot in FIG. 7 is the graft size. Of note, an $R^2$ value describing the fit of the linear regression onto the 22 data points was also computed. The methods described in the present example resulted in 1 million PCAs that informed 1 million predictive linear regressions (i.e., regress the data projected onto PC1 against the known graft size from the training fraction), which predicted 1 million graft sizes. For genes 1-5, increased gene expression was associated with larger graft size, and for genes 6-10, increased gene expression was associated with smaller graft size.

D. Model Grouping, Collapsing, and Ranking

The best model was then selected from the 1 million linear regression models. To do so, a grid comprising an x-axis of the percentage of variance explained by PC1 (PC1%) and a y-axis of the $R^2$ values was generated. The PC1% ranged from 0 to 100%, and the $R^2$ values ranged from 0 to 1. Up to 1000 linear regression models informed by a) PC1% values between 0 and 10%, and b) $R^2$ values between 0 and 0.1, were examined for their predicted graft sizes, and these predicted graft sizes were averaged, and the cross-validation statistics such as the AUC (area under the curve for a receiver-operator curve) were computed. In this way, up to 1000 linear regression models were grouped by their corresponding PC1% values and $R^2$ values, and those linear regression models were collapsed together, by averaging their predicted graft sizes, and by computing, for the collapsed linear regression models, single cross-validation summary statistics, such as a single accuracy and AUC value (as well as $R^2$, sensitivity, specificity, precision, recall, and F1 values). The averaging of the predicted graft sizes buffers much of the variation seen across the predicted graft sizes for the individual models.

The process described above is repeated, but with different ranges of PC1% and $R^2$ values grouping up to 1000 linear regression models. Namely, the ranges of the PC1% increment by 2.5 percentage points. Thus, the second group of up to 1000 linear regression models comprise a) PC1% ranges between 2.5% and 12.5%, and b) $R^2$ values that remain between 0 and 0.1. Again, up to 1000 linear regression models within the specified PC1% and $R^2$ value ranges were collapsed, by averaging the models' predicted graft sizes, and by computing for all the collapsed models, single cross-validation statistics, such as a single accuracy and AUC value, as well as the other metrics stated above. The group of up to 1000 linear regression models continues to increment in units of 2.5% along the x-axis of the grid (and at every distinct group of PC1% and $R^2$ ranges, the predicted graft sizes are averaged, and the cross-validation statistics are computed across the entire group), until the PC1% range becomes at least 90% (given that the window size is 10%, the window does not move beyond 90%, or else the effective window size will become less than 10%, and reasonable comparisons cannot be made against other collapsed models), for the group of up to 1000 linear regression models. Then, the next group of up to 1000 linear regression models comprises a) PC1% ranges between 2.5% and 12.5%, and b) $R^2$ values between 0.025 and 0.125, and again, the up to 1000 models' predicted graft sizes are averaged, and the cross-validation statistics are computed across the entire group. The iterative process of grouping up to 1000 linear regression models based on a range of PC1% values and $R^2$ values continues until the entire space of 0% to 100% PC1% values and 0 to 1 $R^2$ values are tiled. As seen above, each group of linear regression models either increments their PC1% values by 2.5 percentage points or increments their $R^2$ values by 0.025 (i.e., both the x- and y-axes increment by 2.5%). Once the entire space of PC1% values and $R^2$ values has been tiled, the group of collapsed, at most, 1000 linear regression models can be compared via a group statistic, e.g., cross-validation statistic, of interest.

Of note, when the up to 1000 models were collapsed, the predicted graft sizes were averaged. The predicted graft sizes need not, strictly speaking, be averaged, but may be subject to a different form of central tendency, such as a median. The median predicted graft size could be more robust to any outliers present in data in the cell lots, than the mean.

FIGS. 8A-H show the results of grouping, at most, 1000 linear regression models, based on their PC1% and $R^2$ values. Each plot in FIGS. 8A-H is heat-mapped, with respect to a group statistic of interest, where the x-axis is the PC1% and the y-axis is the $R^2$ of the linear regression model, i.e., each plot in FIGS. 8A-H depicts the grid of PC1% by $R^2$ space, described above. That is, FIGS. 8A-H heat-maps, in corresponding order, the $R^2$, AUC, sensitivity, specificity, precision, F1, accuracy, and kappa values of the grouped models. In FIGS. 8A-H, the black-outlined circle in each plot indicates the model (collapsed from the group of models with similar PC1% and $R^2$ values) with the highest AUC and highest accuracy. The present example ranked the best groups of up to 1000 linear regression models, to be the groups of models ranked first by the highest accuracy, and then ranked by the highest AUC.

FIGS. 9A-B shows the predictive characteristics of a group of PCA-based linear regression models. FIG. 9A depicts, for the (collapsed) model with, first, the highest AUC and, second, the highest accuracy, the relationship between predicted graft size, according to an arbitrary scale normalized from 0 to 1 arbitrary units, and measured graft size, also according to an arbitrary scale normalized from 0 to 1 arbitrary units. FIG. 9B depicts for the model with the highest AUC and highest accuracy, the receiver operator characteristic curve (ROC curve), and its corresponding AUC.

Figures 9, 10:
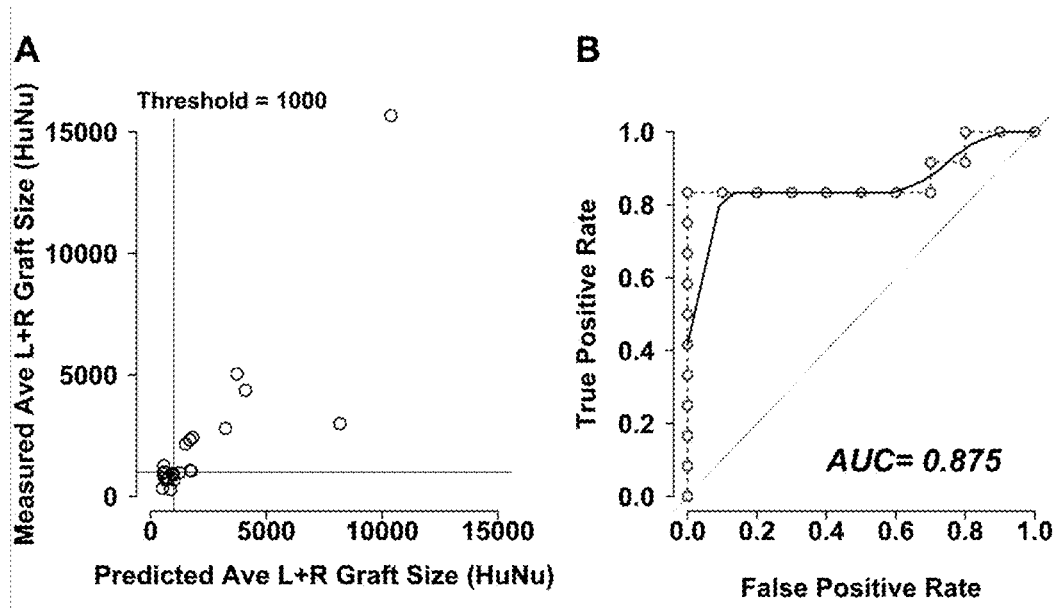
FIG. 9 depicts a non-limiting example of data that depicts the prediction performance of a linear regression model derived from PCA, that is predictive of the size of grafts obtained from a population of neuronal progenitor cells when the neuronal progenitor cells are implanted into a subject brain, based on gene expression levels of the neuronal progenitor cells.
FIG. 10 depicts a non-limiting example of data that depicts the summary statistics of a linear regression model derived from PCA, that is predictive of the size of grafts obtained from a population of neuronal progenitor cells when the neuronal progenitor cells are implanted into a subject brain, based on gene expression levels of the neuronal progenitor cells.

FIG. 10 depicts various characteristics of the model with, first, the highest AUC and, second, highest accuracy, i.e., the best model (recall that this model is derived from collapsing, at most, 1000 models with similar $R^2$ and PC1% values). The best model comprises an accuracy of 0.8636, an AUC of 0.875, a $R^2$ of 0.7353, a sensitivity of 0.9, a specificity of 0.8333, a precision of 0.8182, a recall of 0.9, and an F1 of 0.8571.

A desired number of highest ranking groups of the up to 1000 linear regression models can be selected according to any desired criteria, such that a desired number of unique genes from those groups of models' corresponding 5-gene sets can be identified.

Example 2—Non-PCA-Based Model for Predicting Graft Size

A machine learning method for predicting the outcome of grafting dopaminergic neuronal progenitor cells (DANPCs), based on gene expression levels of DANPCs, was developed. To do so, bulk gene expression levels from a fraction of cells of a population of human DANPCs differentiated from in vitro pluripotent stem cells (iPSCs) were ascertained. A remaining fraction of cells from the same population of human DANPCs were stereotactically injected, either unilaterally or bilaterally, into the striatum of a rat. The injected DANPCs were then quantified via an image processing software, to derive various features related to the DANPCs' grafting outcomes. Of these grafting outcomes, the graft size of the injected DANPCs were ascertained. Thus, from a given population of human DANPCs, population-specific bulk gene expression levels and a population-specific graft size was obtained. Population-specific bulk gene expression levels and population-specific graft sizes were obtained for DANPC populations deriving from multiple human subjects. The non-PCA-based model described in the present example used DANPC gene expression levels to predict the graft sizes of injected DANPCs.

The training data and test data used for training and testing the machine learning model included bulk RNA sequencing (RNAseq) data of the DANPCs. The bulk gene expression levels were then modeled against the graft size of the corresponding DANPCs, via the edgeR software package in the R programming language. The edgeR software package modeled the relationship between individual gene expression and the response variable, graft size, with an overdispersed Poisson model, such that each gene received its own estimate from a generalized linear model likelihood ratio test. Based on the overdispersed Poisson model, the top 1000 genes associated with graft size was identified, for a given training fraction.

A. Splitting the Data, by Donor, into Training and Test Fractions

The resulting data regarding the associations between the bulk RNAseq data and the corresponding DANPCs' graft size were split into a training data fraction and a test data fraction, via a leave-one-out (LOO) methodology, for the same number of iterations as the number of donors represented in the edgeR-modelled data, e.g., 7 iterations. The LOO method is a type of cross-validation method. The purpose of cross-validation is to control for the undesirable possibility that the training data fraction may not be representative of the variable of interest for prediction, and thus, the model fails to generalize, because the model is trained on unusual data. The training data fraction may, by random chance, comprise a highly unusual composition of data, and training a model based on such an unusual composition may result in a model that does not generalize across all or most instances of the variable of interest for prediction. To limit such artifacts, cross-validation is used. Cross-validation entails generating many pairs of training and test data fractions. In the case of LOO cross-validation, a single data point is reserved as the test data, and the remaining data is considered the training data. In the present example, DANPCs derived from 7 subjects, and thus 7 iterations of LOO were used for cross-validation: one subject (e.g., subject A) for test data and the remaining six subjects (subjects B-G) for training data; one subject (e.g., subject B) for test data and the remaining six subjects (subjects A, C-G) for training data . . . one subject (e.g., subject G) for test data and the remaining six subjects (subjects A-F) for training data. LOO cross-validation is useful in the case where the sample size of independent and individually distributed (IID) random variables is small. The present example considers the relevant sample size to be the number of subjects, unlike many other methods which consider the relevant sample size to be the number of cells to be grafted, e.g., DANPCs. Although using the number of subjects as the relevant sample size will often result in a smaller sample size than if the number of cells were used, opting for the number of subjects as the relevant sample size during cross-validation can result in a machine learning model with improved predictive power. Some methods, however, opt to use the number of cells as the sample size, because doing so often inflates the sample size, and the experimenter may believe that a higher sample size is unconditionally favorable. Methods that use the number of cells to be grafted as the relevant sample size, however, can often lead to a machine learning model with poor predictive power, because in cases where the cells to be grafted derive from common donors, the cells that derive from a common donor are not truly IID-cells from a common donor likely have much more in common than if they were compared to cells from another donor. In addition, by considering the relevant sample size to be the number of subjects, rather than the number of cells to be grafted, splitting of the data into training and test fractions during cross-validation does not result in cells from a given donor to be present in both the training and test fractions. Such a model design choice is especially important when using RNAseq data from donor cells because most of the unique signatures in donor cell RNAseq data is indicative of the idiosyncrasies of the donor subject, rather than being indicative of a more general variable of interest common to most donors, such as a cell grafting outcome, e.g., graft size. For the reasons above, the methods described in the present example opt to use the number of subjects, and not the number of cells for grafting, as the relevant sample size for cross-validation, even though doing so may result in a smaller number of iterations for cross-validation. Accordingly, the cross-validation method used in the present example is limited to a cross-validation method that is compatible with a small sample size, and thus, LOO is used.

B. Computing on Three Randomly Sampled Genes

Based on the edgeR-based modeled gene expression data and their associations with graft size, the top 1000 genes associated with graft size was identified, for each of the seven training fractions. The intersecting genes across each of the seven training fractions was then identified. In addition to the genes being intersecting, each gene needed to possess at least 40 reads mapped to the gene, in at least six of the training fraction RNAseq libraries. 98 intersecting genes were identified, based on these criteria. The 98 genes were then further filtered using the 40 reads mapped to a given gene in at least six of the training fraction RNAseq libraries, such that only the more highly expressed genes remained. After filtering for the highly expressed genes, 62 genes remained. FIG. 11 depicts a schematic workflow of the non-PCA-based model for using bulk gene expression data from DANPCs to predict graft size.

From the remaining 62 genes, 3 genes were randomly sampled. The total number of possible combinations of 3 genes drawn from 62 possible genes is $$\binom{62}{3} = 37820$$

possible combinations. To achieve greater computational efficiency, sets of 3 genes were randomly sampled only 20000 times from the 37820 possibilities, and thus, approximately a near four-fold efficiency in computation was gained. In addition, the selection of using very few genes, e.g., 3 genes, from the total number of possible 62 genes, controls the otherwise outsized influence that a particular donor subject would have when generating one or more models for predicting graft size. If a large number of genes was selected from the total number of possible 62 genes, most of the predictive power informed by the gene expression data would relate not to general grafting outcome, i.e., a grafting outcome common or agnostic to the donor subjects, but rather, would relate mostly to the idiosyncrasies of the particular donor subject. Thus, to avoid generating a model that is based on overfitting the training data, only a small number of genes, e.g., 3 genes, were repeatedly selected from the 62 possible genes.

C. Generating Linear Regression Models from Gene Expression and Known Graft Sizes To generate a model predictive of graft size for each of the randomly sampled 3 gene combinations, the gene expression levels of each of the 3 genes were linearly regressed against the graft sizes of the 22 cell lots, to generate a linear regression model of the form y=mx+b. Recall that the dataset analyzed in the present example comprises 22 cell lots deriving from 7 donor subjects, where each cell lot has corresponding bulk RNAseq data, which includes expression data for the top 62 genes. Thus, each linear regression model was derived from a sample size of 22 cell lots, where the predictor variable was the bulk gene expression of one of the three randomly selected genes, for a given cell lot, and the response variable was the graft size for a given cell lot.

Figure 12:
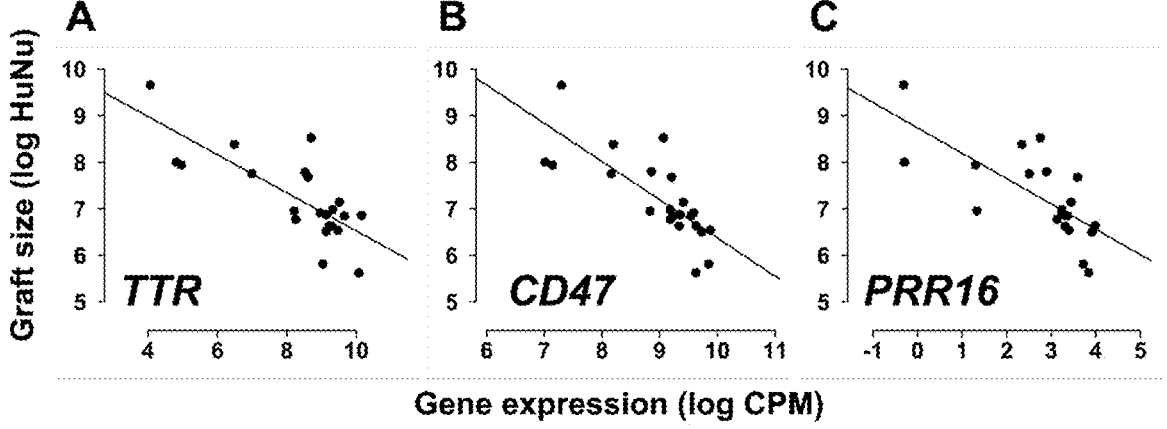
FIGS. 12A-C depict a non-limiting example of data for a set of linear regressions for a linear regression model derived without using PCA, to predict whether a population of neuronal progenitor cells are likely to successfully engraft when implanted into a region of a brain, based on gene expression levels of three genes.

FIGS. 12A-C depicts linear regression models for each of three randomly selected genes from the list of 62 genes. The x-axis of each plot in FIGS. 12A-C is the gene expression of the one of the three randomly selected genes (in this case, TTR (FIG. 12A), CD47 (FIG. 12B), and PRR16 (FIG. 12C), and the y-axis of each of the plots is the graft size of the cell lot. Each datapoint on each of the plots corresponds to one of the 22 cell lots. To emphasize, each linear regression model in the present example is based on data from the training fraction. The linear regression models can then be used to predict graft sizes, based on gene expression data from the test fraction. For each set of three linear regression models corresponding to the set of three randomly selected genes, the three predicted graft sizes were averaged, to generate a single predicted graft size. Of note, the averaging can be replaced with some other kind of central tendency calculation, such as the median, which can tend to be more robust than the mean, to outliers. Each set of three linear regression models were collapsed together, and for the collapsed model, a single accuracy, a single AUC and other single cross-validation summary statistics were determined.

Figure 13:
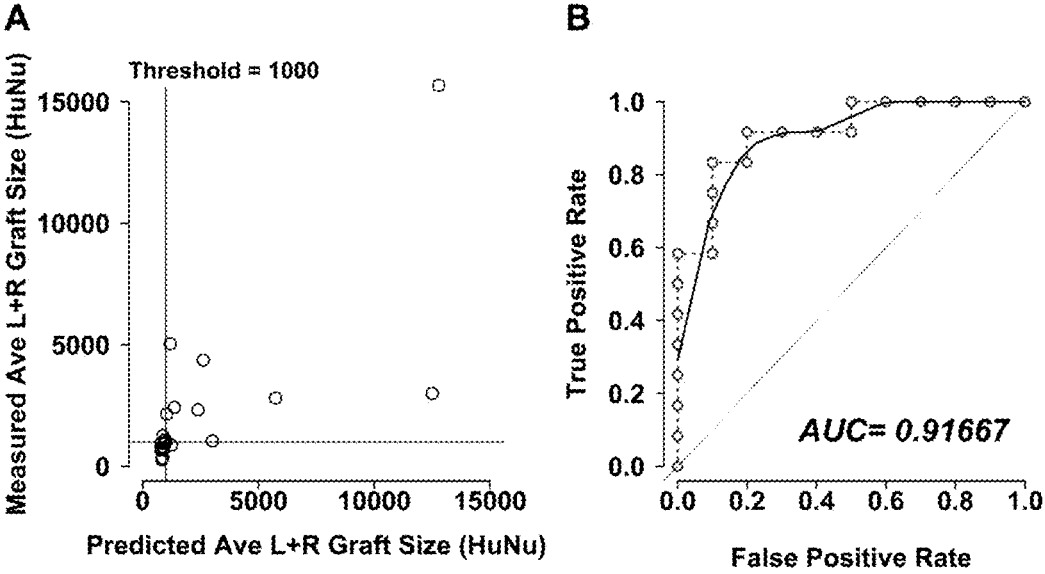
FIG. 13 depicts a non-limiting example of data that depicts the predictive performance of a linear regression model without using PCA, that is predictive of the size of grafts obtained from implantation of neuronal progenitor cells into a subject brain, based on gene expression levels in the neuronal progenitor cells.

FIG. 13A depicts the relationship between the measured and the predicted graft sizes obtained using a gene-based model, and FIG. 13B depicts the receiver-operating characteristic (ROC) curve, as well as its associated AUC value, for the 3-gene model based on TTR, CD47, and PRR16, as shown in FIGS. 12A-C. FIG. 14 depicts a number of summary statistics associated with the collapsed model depicted in FIG. 13A-B, including the AUC depicted in FIG. 13B. The best collapsed linear regression models were ranked according to decreasing accuracy. Given that each set of three linear regression models corresponded to three randomly selected genes from a list of 62 genes, the most accurate models corresponded to a list of genes that informed those most accurate models. Further analysis, such as the application of a threshold cutoff can further curate the list of informative genes, to identify some number of genes of interest, to be used for e.g., biomedical or clinical applications.

Figure 15:
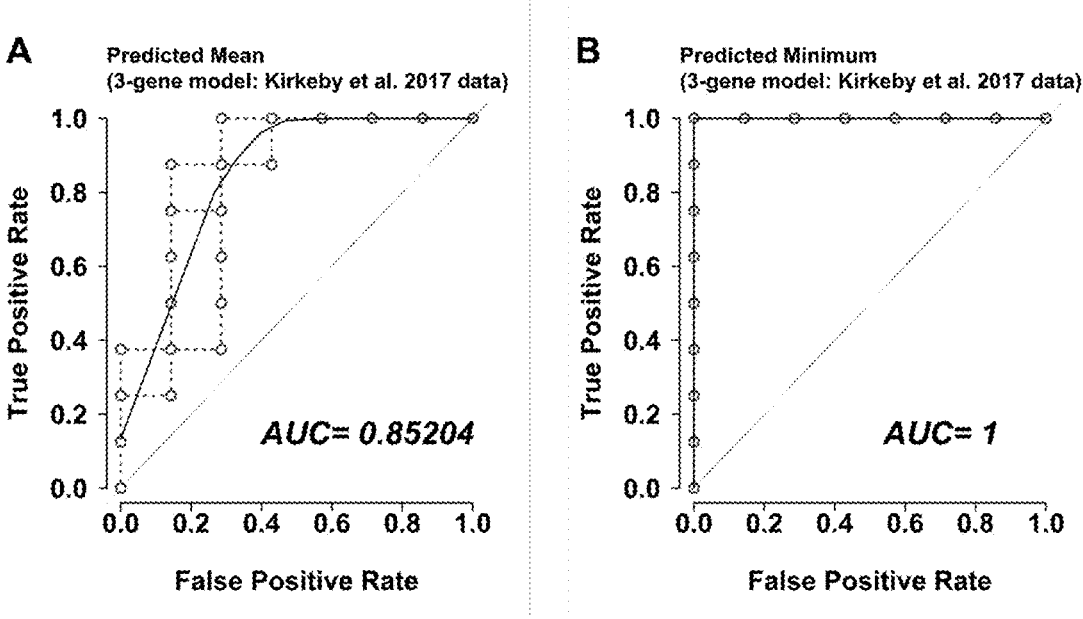
FIGS. 15A-B depict a non-limiting example of data that validates the performance of linear regression models derived without using PCA, to predict the size of grafts obtained from implantation of neuronal progenitor cells into a subject brain, based on gene expression levels in the neuronal progenitor cells. Out-of-sample data and labels are from Kirkeby et al. (2017) *Cell Stem Cell* 20 (1): 135-148. Number of Th+ cells in graft/100,000 injected cells informed the "DA Yield" label (DA high/DA low; n=15 predictions. All graft measures for a single cell line (H9 ESC).

FIGS. 15A-B shows the results of deploying the best collapsed linear regression models on an external dataset, as identified based on the methods described in the present example. The external dataset was derived from Kirkeby et al. (2017) *Cell Stem Cell* 20(1): 135-148. The external dataset comprised of cells that were classified as high in dopamine, or low in dopamine, depending on how much tyrosine hydroxylase there was, per 100,000 transplanted cells (tyrosine hydroxylase is a necessary enzyme for synthesizing dopamine, and thus, a biomarker for identifying dopaminergic cells). The gene expression data from the cells that were high in dopamine were used as inputs to the 7 best models, where each of the 7 best models corresponded to the best model from each of the 7 training data fractions (i.e., the best model from the training fraction of each of the 7 folds of the cross-validation). For each of the 7 models, the grafting outcome was predicted by either computing the mean graft size from the 3 genes used for one of the 7 models, or by computing the minimum graft size from the 3 genes used for one of the 7 models. Accordingly, the AUC for each of the 7 models was determined for when the mean graft size from the 3 genes was used, and for when the minimum graft size from the 3 genes was used. The mean AUC, when using the mean predicted graft size, is depicted in FIG. 15A, with a mean AUC of 0.85204 across the 7 models. The mean AUC, when using the minimum predicted graft size, is depicted in FIG. 15B, with a mean AUC of 1.00.

One key advantage of the methods described in the present example is the ability to rank lots based on their predicted capacity to engraft and make functional connections in the host brain. FIGS. 16A-F shows the extent to which rank orders of graft size were resolved using the models generated by the methods described in the present example. For simplicity, results related to the 3-gene-based models are shown here. FIGS. 16A-F show the normalized graft sizes for predicted size and actual measured size. Out of the six samples that were tested, and among which lots from the same differentiation set could be compared (donors 1-6), there was a clear effect of magnitude of difference in the models' ability to resolve the correct rank order. In other words, if the measured differences between lots were large, the model was able to successfully predict the correct size rank order. In cases where grafts were very similar in measured size, the model performed less well. This concept is shown in FIGS. 16A-F. The plots in FIGS. 16A-F depict, for each plot, two lots from a donor, for which the lot sizes were measured and predicted, and the data were normalized to the largest value. A fixed-radius circle was overlaid on each of the plots, to provide visualization of the scale of difference, and how well the models performed. Grey circles show sample differences greater than one radius distance (i.e., 0.2 normalized value). White circles show where both samples are within a circle of radius 0.2 normalized value. The direction of the line joining the two data points in each of the sample plots (FIGS. 16A-F). If the line connecting the data has a positive coefficient, the model was able to resolve the rank orders correctly (donors 1 (FIG. 16A), 2 (FIG. 16B), 3 (FIG. 16C), 5 (FIG. 16E), denoted as gray circles). In cases where the line is near vertical or has a negative coefficient, the model did not correctly predict the rank order (donors 4 (FIG. 16D) and 6 (FIG. 16F), denoted as white circles). These cases are related to the magnitude of the difference between the large and small grafts. When data are very similar in magnitude (on a normalized scale), the two data are within a 0.2 radius circle of the largest graft and these cases were not correctly resolved. When one datum was in the circle and the other datum is outside of the circle, the model always correctly predicted the rank orders. In short, regarding the model's ability to predict the likelihood of a DANPC lot to graft into a host, the model performs better when the two DANPC lots were further apart in the predicted graft size vs. measured graft size space. In other words, the models generated by the methods described in the present example are more likely to correctly detect large magnitude differences and are less likely to correctly detect small magnitude differences, in the space of predicted and measured graft sizes.

Figure 16:
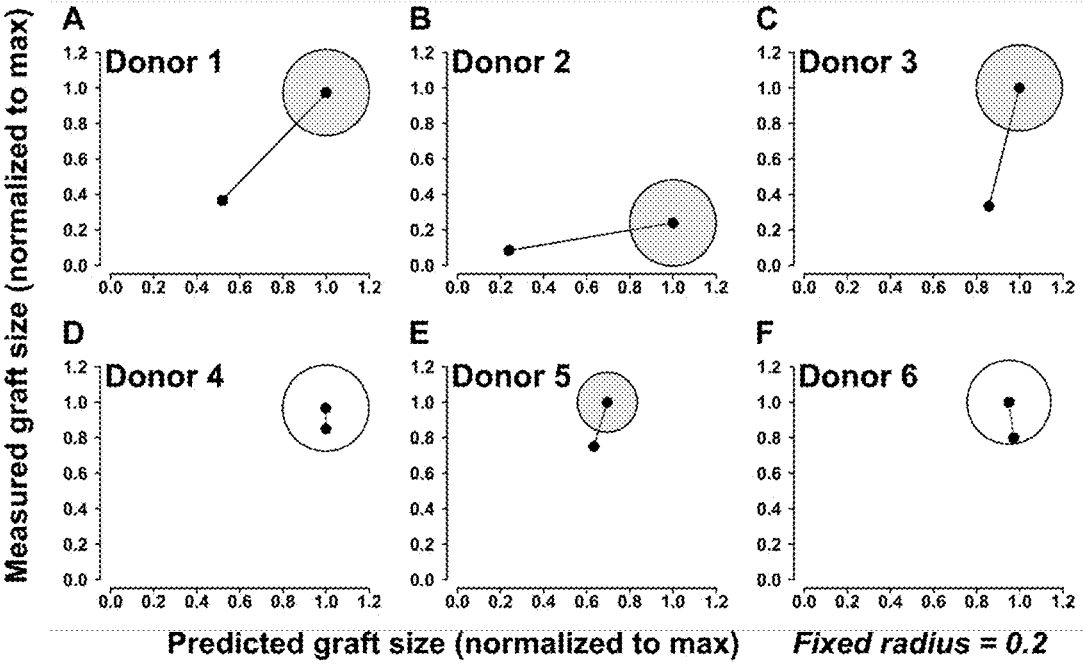
FIGS. 16A-F depict a non-limiting example of data that depicts the concordance between measured and predicted graft sizes, for cell lots of six donors, when predicted using linear regression models derived without using PCA.
Figure 17:
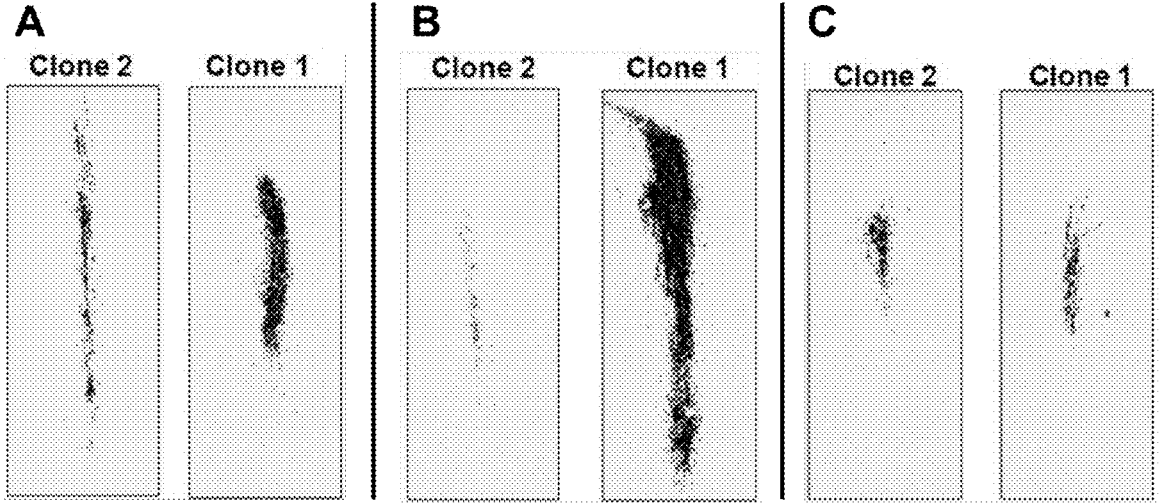
FIGS. 17A-C depict a non-limiting example of data that depicts images of grafts obtained from implantation of neuronal progenitor cells into rodent host brains. Cell nuclei are shown.
Figure 18:
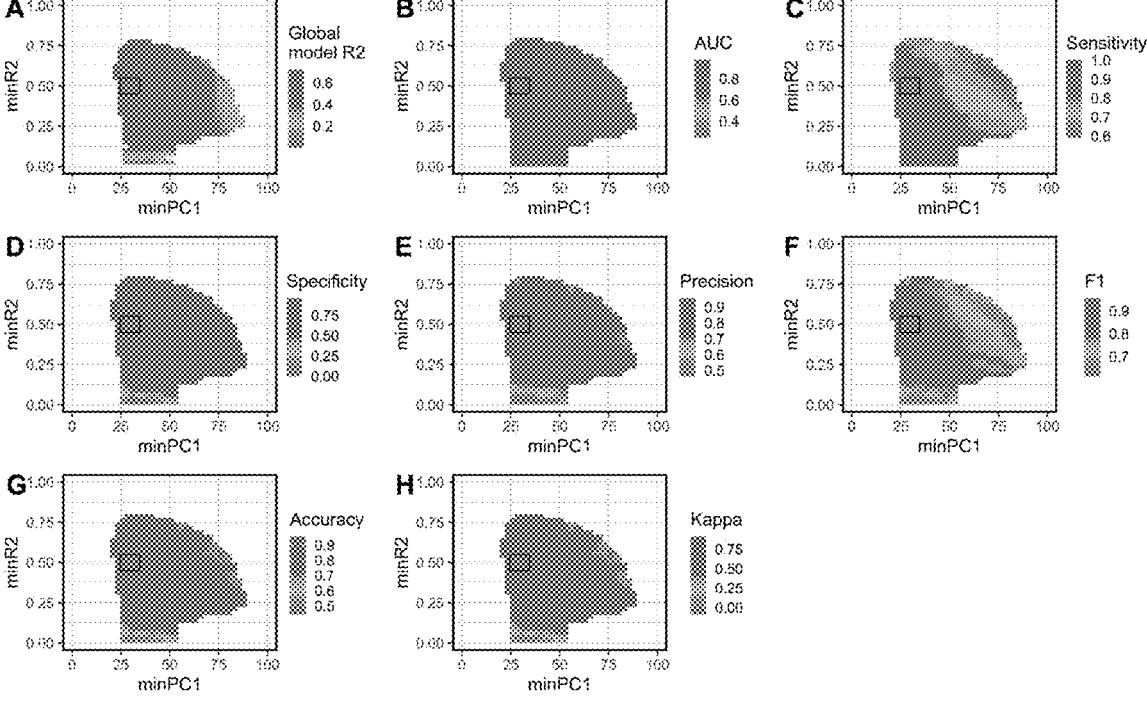
FIGS. 18A-H depicts a non-limiting example of data that depicts linear regression models derived from PCA, that are predictive of amounts of dopamine released by neuronal cells derived from a population of neuronal progenitor cells after the neuronal progenitor cells are implanted into a subject brain, based on gene expression levels in the neuronal progenitor cells, wherein the models are organized according to their $R^2$ value and their percentage of variance explained by PC1 (PC1%).

FIG. 17A-C shows microscopy images of three pairs of DANPC clone graft nucleii after being grafted for 21 days. Each pair of clones corresponds to a pair of clones for which their predicted and actual graft sizes were plotted and analyzed, as shown in FIG. 16. More specifically, the two clones depicted in FIG. 17A corresponds to the two clones depicted for donor 1 in FIG. 16A; the two clones depicted in FIG. 17B corresponds to the two clones depicted for donor 2 in FIG. 16B; and the two clones depicted in FIG. 17C corresponds to the two clones depicted for donor 3 in FIG. 16C.

The methodology described in the present example can be performed with different parameter values, and with different and/or additional downstream filtering steps. For example, the 20000 random selections of 3 genes from the 62 possible genes, need not be 20000 random selections. The number of random selections can instead be e.g., 20000 random selections of 3 genes from the 62 possible genes. In one variation of the methodology described above, 20000 random selections of 3 genes were selected from the 62 possible genes identified above. From each of the 20000 random selections of 3 genes, 3 linear regression models were identified and collapsed together, according to the methods described above. The 20000 collapsed linear regression models were then filtered, such that only models with accuracies greater than 0.7 were selected. 2766 models remained after the filtering. All genes that appeared in the 2766 models were combined and ranked by their accuracy. The top 50 genes associated with the ranked 2766 models were then identified. The expression levels of the top 50 genes were then quantified, by normalizing the counts per million (CPM) for a gene of interest, normalized by the CPM for a reference gene, such as the house-keeping gene, GAPDH. The expression levels were also alternatively quantified, by taking the base 2 logarithm of the CPM for a gene of interest, normalized by the base 2 logarithm of the CPM for a reference gene, such as the house-keeping gene, GAPDH. The results of the top 50 identified genes are listed in Table E1.

TABLE E1

Top 50 genes and their conditional ratio value associated with grafts ≥ 1,000 HuNu cell counts.

| Gene ID | Greater graft sizes are consistent with $\log_2$CPM Gene/$\log_2$CPM GAPDH | CPM Gene$_x$/ CPM GAPDH | $\log_2$CPM Gene/$\log_2$CPM GAPDH |
|---|---|---|---|
| AC000120.3 | less than | 0.001299 | 0.112210552 |
| KRT77 | less than | 0.048527 | 0.561259341 |
| TTR | less than | 0.612923 | 0.93090804 |
| PRR16 | less than | 0.011352 | 0.357654078 |
| MEGF10 | less than | 0.122763 | 0.69578207 |
| PDE3A | less than | 0.3178 | 0.833720314 |
| GDPD2 | less than | 0.089861 | 0.650550417 |
| CMTM8 | less than | 0.356002 | 0.85018473 |
| APOA1 | less than | 0.04558 | 0.564243666 |
| CMTM7 | less than | 0.154602 | 0.736523536 |
| CDHR3 | less than | 0.538684 | 0.91026302 |
| CORIN | less than | 1.25561 | 1.03301952 |
| VTN | less than | 0.289372 | 0.820128861 |
| CPNE8 | less than | 0.091004 | 0.655875492 |
| EFEMP1 | less than | 0.115467 | 0.688392724 |
| CD47 | less than | 0.78273 | 0.964464764 |
| SPARC | less than | 1.711454 | 1.077949438 |
| JAM2 | less than | 0.114641 | 0.685857276 |
| CDO1 | less than | 0.323823 | 0.836443369 |
| PLXDC2 | less than | 0.323926 | 0.836489607 |
| DYNLL2 | greater than | 0.106623 | 0.699701493 |
| ITGA3 | greater than | 0.007227 | 0.286173205 |
| RPS6KL1 | greater than | 0.007978 | 0.319066588 |
| CHRNB2 | greater than | 0.004137 | 0.264950388 |
| SULT4A1 | greater than | 0.006746 | 0.276261679 |
| PTPN3 | greater than | 0.000742 | 0.040041013 |
| LZTS1 | greater than | 0.003655 | 0.24133104 |
| RUNX1T1 | greater than | 0.007274 | 0.306124055 |
| TMEM145 | greater than | 0.001514 | 0.064495481 |
| EPHA10 | greater than | 0.003506 | 0.207192524 |
| CARMIL3 | greater than | 0.003923 | 0.198691695 |
| MANEAL | greater than | 0.005622 | 0.304989973 |
| TMEM176B | greater than | 0.00026 | -0.135615672 |
| MPP3 | greater than | 0.002434 | 0.151863277 |
| DRAXIN | greater than | 0.009884 | 0.337025763 |
| ADGRB1 | greater than | 0.001824 | 0.090421905 |
| KIF26A | greater than | 0.00657 | 0.291873902 |

TABLE E1-continued

Top 50 genes and their conditional ratio value associated with
grafts ≥ 1,000 HuNu cell counts.

| Gene ID | Greater graft sizes are consistent with log₂CPM Gene/log₂CPM GAPDH | CPM Gene$_x$/ CPM GAPDH | Log₂CPM Gene/log₂CPM GAPDH |
|---|---|---|---|
| CELF5 | greater than | 0.009017 | 0.3179975 |
| CNTN2 | greater than | 0.005065 | 0.291862989 |
| ASPHD1 | greater than | 0.001317 | 0.106895349 |
| SVOP | greater than | 0.002579 | 0.202285412 |
| ANGPT2 | greater than | 0.000418 | −0.07458534 |
| SLC22A15 | greater than | 0.000965 | 0.051296136 |
| SRRM3 | greater than | 0.003358 | 0.219114339 |
| GRIN2D | greater than | 0.001205 | 0.032905084 |
| DACH2 | greater than | 0.000278 | −0.080786018 |
| CHST1 | greater than | 0.000499 | −0.05809988 |
| GRIN1 | greater than | 3.44E−05 | −0.331836948 |
| LHX5 | greater than | 0.000411 | −0.082452256 |
| NOS2 | greater than | 0.000352 | −0.10138678 |

Example 3—PCA-Based Model for Predicting
Dopamine Release Quantities

A machine learning method for predicting the amount of released dopamine from cultured DANPCs, upon the addition of potassium chloride (KCl), based on gene expression levels of DANPCs, was developed. To do so, bulk gene expression levels from a fraction of cells of a population of human DANPCs differentiated from in vitro pluripotent stem cells (iPSCs) were ascertained. A remaining fraction of cells from the same population of human DANPCs were cultured in vitro for approximately 60 days. KCl was then added to the DANPCs, to stimulate the release of dopamine (as well as serotonin). The amount of released dopamine (and serotonin) from the cultured DANPCs was obtained by liquid chromatography-mass spectrometry (LC-MS). Thus, from a given population of human DANPCs, population-specific bulk gene expression levels and a population-specific amount of released dopamine was obtained. Population-specific bulk gene expression levels and population-specific amounts of released dopamine were obtained for DANPC populations deriving from multiple human subjects. The PCA-based model described in the present example used DANPC gene expression levels to predict the amount of dopamine released by the cultured DANPCs. FIG. 6 depicts a schematic workflow of the PCA-based model for using bulk gene expression data from DANPCs to predict graft size, but the same general workflow can be applied to predicting the amount of dopamine released from cultured DANPCs. Of note, the methods described herein need not be limited to predicting the amount of dopamine released by DANPCs, but can generalize to a) predicting the amount of any released biological compound, e.g., neurotransmitter, such as dopamine or serotonin, provided that the relevant training data is used, and; b) other cell types that are not DANPCs.

The training data and test data used for training and testing the machine learning model included bulk RNA sequencing (RNAseq) data of the DANPCs. The bulk gene expression levels were then correlated against the amount of dopamine released by the corresponding DANPCs. The strength of the correlations between the amount of released dopamine and the corresponding DANPCs' RNAseq expression were quantified by metrics, e.g., the Pearson's correlation coefficient, in accordance with the Weighted Correlation Network Analysis (WGCNA) software package in the R programming language.

A. Splitting the Data, by Donor, into Training and Test Fractions

The resulting data regarding the correlations between the bulk RNAseq data and the corresponding amount of dopamine released by the DANPCs were split into a training data fraction and a test data fraction, via a leave-one-out (LOO) methodology, for the same number of iterations as the number of donors represented in the correlation data, e.g., 8 iterations. The LOO method is a type of cross-validation method. The purpose of cross-validation is to control for the undesirable possibility that the training data fraction may not be representative of the variable of interest for prediction, and thus, the model fails to generalize, because the model is trained on unusual data. The training data fraction may, by random chance, comprise a highly unusual composition of data, and training a model based on such an unusual composition may result in a model that does not generalize across all or most instances of the variable of interest for prediction. To limit such artifacts, cross-validation is used. Cross-validation entails generating many pairs of training and test data fractions. In the case of LOO cross-validation, a single data point is reserved as the test data, and the remaining data is considered the training data. In the present example, DANPCs derived from 8 subjects, and thus 8 iterations of LOO were used for cross-validation: 1 subject (e.g., subject A) for test data and the remaining 7 subjects (subjects B-H) for training data; 1 subject (e.g., subject B) for test data and the remaining 7 subjects (subjects A, C-H) for training data . . . 1 subject (e.g., subject H) for test data and the remaining 7 subjects (subjects A-G) for training data. LOO cross-validation is useful in the case where the sample size of independent and individually distributed (IID) random variables is small. The present example considers the relevant sample size to be the number of subjects, unlike many other methods which consider the relevant sample size to be the number of cultured cells, e.g., DANPCs. Although using the number of subjects as the relevant sample size will often result in a smaller sample size than if the number of cells were used, opting for the number of subjects as the relevant sample size during cross-validation can result in a machine learning model with improved predictive power. Some methods, however, opt to use the number of cultured cells as the sample size, because doing so often inflates the sample size, and the experimenter may believe that a higher sample size is unconditionally favorable. Methods that use the number of cells as the relevant sample size, however, can often lead to a machine learning model with poor predictive power, because in cases where the cells derive from common donors, the cells that derive from a common donor are not truly IID-cells from a common donor likely have much more in common than if they were compared to cells from another donor. In addition, by considering the relevant sample size to be the number of subjects, rather than the number of cultured cells (e.g., cell lots), splitting of the data into training and test fractions during cross-validation does not result in cells from a given donor to be present in both the training and test fractions. Such a model design choice is especially important when using RNAseq data from donor cells because most of the unique signatures in donor cell RNAseq data is indicative of the idiosyncrasies of the donor subject, rather than being indicative of a more general variable of interest common to most donors, such as the amount of released dopamine. For the reasons above, the methods described in the present example opt to use the number of subjects, and not the number of cells or cell lots, as the relevant sample size for LOO, even though doing so may result in a smaller number of iterations for LOO. Accordingly, the cross-validation method used in the present example is limited to a cross-validation method that is compatible with a small sample size, and thus, LOO is used.

B. Performing PCA on Five Randomly Sampled Genes

For each of the eight iterations, LOO was performed on the correlation data (i.e., the correlation data regarding the correlations between a given gene's expression levels from DANPC bulk RNAseq data, and the corresponding DANPCs' amounts of released dopamine), the correlation data in the training fraction was ranked, and the top 2000 correlation values were selected from each iteration's training fraction. For each iteration's training fraction, the 2000 genes corresponding to the 2000 correlation values were selected, and the genes that were common to all eight iterations were identified. The genes common to all eight iterations were then filtered for expression levels greater than 0 log counts per million (log CPM). Three hundred fifty-eight genes were identified to be common to the training fractions of all 8 LOO iterations and survived expression filtering. Of the 358 identified genes, five genes were randomly selected and principal component analysis (PCA) was run on the five genes. The random selecting of five genes from the 358 identified genes, followed by PCA on the five randomly selected genes, was done a million times, resulting in a million PCA outcomes (e.g., the percentage of variance of the data explained by each principal component resulting from each PCA, etc.). An $R^2$ value was also determined for each training data fraction used for generating each of the million PCA outcomes (i.e., an $R^2$ value between the RNAseq levels for the five selected genes and the corresponding amount of released dopamine). The result of the 1 million PCAs was a dataset comprising 1 million rows, where each row comprised the corresponding $R^2$ value, and the percentage of variance of the data explained by each principal component (PC) resulting from each PCA. Of note, running the million PCAs represents an aspect of increased computational efficiency, when compared to the complete number of PCAs that would be required for investigating every possible selection of five genes from the 358 identified genes. The total number of possible combinations of five genes drawn from 358 possible genes is $$\binom{358}{5} = 7,648,760,726$$

possible combinations, and thus, randomly using only one million five-gene sets for PCA, of the 7,648,760,726 possible combinations, saves on roughly six orders of magnitude in computational efficiency. In addition, the selection of using very few genes, e.g., five genes, from the total number of possible 358 genes, controls the otherwise outsized influence that a particular donor subject would have when training the machine learning model, e.g., model derived from the PCAs. If a large number of genes was selected from the total number of possible 534 genes, and PCA was then performed on the large number of genes, most of the variance captured by the PCA would relate not to general amounts of released dopamine, i.e., an amount of released dopamine common or agnostic to the donor subjects, but rather, would relate mostly to the idiosyncrasies of the particular donor subject. Thus, to avoid overfitting the PCAs onto the training data, only a small number of genes, e.g., five genes, were repeatedly selected from the 358 possible genes.

C. Generating Linear Regression Models from PC1 and Known Amount of Released Dopamine Each row of the 1 million row dataset, which describes the results of a PCA, was used to predict the amount of released dopamine from the test fraction, via linear regression. Some of the results of each PCA of the 1 million PCAs can be described as a matrix of 45 cell lots×5 PCs, of which only the column vector describing the first PC (i.e., PC1) results are of interest, i.e., 45 cells lots×PC1. The elements of the 45 cells lots×PC1 vector are, more specifically, the projections of the gene expression (e.g., bulk RNAseq) data onto PC1 (i.e., the first set of co-ordinates in PC space). The 45 projections onto PC1 were plotted against the amount of released dopamine of the 45 corresponding cell lots from the training fraction, and linear regression was performed, i.e., a predictive linear model of the form y=mx+b was generated, where y is the predicted amount of released dopamine. The test data fraction was then inputted into the predictive linear models (informed by the training data fraction) to generate predicted amount of released dopamine. Thus, each PCA corresponds to a set of five genes from the possible 358 genes, and a resulting predicted amount of released dopamine, via a linear relationship. Of note, an $R^2$ value describing the fit of the linear regression onto the 45 data points was also computed. The methods described in the present example resulted in 1 million PCAs that informed 1 million predictive linear regressions (i.e., regress the data projected onto PC1 against the known amount of released dopamine from the training fraction), which predicted 1 million amounts of released dopamine.

D. Model Grouping, Collapsing, and Ranking

The best model was then selected from the 1 million linear regression models. To do so, a grid comprising an x-axis of the percentage of variance explained by PC1 (PC1%) and a y-axis of the $R^2$ values was generated. The PC1% ranged from 0 to 100%, and the $R^2$ values ranged from 0 to 1. Up to 1000 linear regression models informed by a) PC1% values between 0 and 10%, and b) $R^2$ values between 0 and 0.1, were examined for their predicted amounts of released dopamine, and these predicted amounts of released dopamine were averaged, and the cross-validation statistics such as the AUC (area under the curve for a receiver-operator curve) were computed. In this way, up to 1000 linear regression models were grouped by their corresponding PC1% values and $R^2$ values, and those linear regression models were collapsed together, by averaging their predicted amounts of released dopamine, and by computing, for the collapsed linear regression models, single cross-validation summary statistics, such as a single accuracy and AUC value (as well as $R^2$, sensitivity, specificity, precision, recall, and F1 values). The averaging of the predicted amounts of released dopamine buffers much of the variation seen across the predicted amounts of the released dopamine for the individual models.

The process described above is repeated, but with different ranges of PC1% and $R^2$ values grouping up to 1000 linear regression models. Namely, the ranges of the PC1% increment by 2.5 percentage points. Thus, the second group of up to 1000 linear regression models comprise a) PC1% ranges between 2.5% and 12.5%, and b) $R^2$ values that remain between 0 and 0.1. Again, up to 1000 linear regression models within the specified PC1% and $R^2$ value ranges were collapsed, by averaging the models' predicted amounts of released dopamine, and by computing for all the collapsed models, single cross-validation statistics, such as a single accuracy and AUC value, as well as the other metrics stated above. The group of up to 1000 linear regression models continues to increment in units of 2.5% along the x-axis of the grid (and at every distinct group of PC1% and $R^2$ ranges, the predicted amounts of released dopamine are averaged, and the cross-validation statistics are computed across the entire group), until the PC1% range becomes at least 90% (given that the window size is 10%, the window does not move beyond 90%, or else the effective window size will become less than 10%, and reasonable comparisons cannot be made against other collapsed models). Then, the next group of up to 1000 linear regression models comprises a) PC1% ranges between 2.5% and 12.5%, and b) $R^2$ values between 0.025 and 0.125, and again, the up to 1000 models' predicted amounts of released dopamine are averaged, and the cross-validation statistics are computed across the entire group. The iterative process of grouping up to 1000 linear regression models based on a range of PC1% values and $R^2$ values continues until the entire space of 0% to 100% PC1% values and 0 to 1 $R^2$ values are tiled. As seen above, each group of linear regression models either increments their PC1% values by 2.5 percentage points or increments their $R^2$ values by 0.025 (i.e., both the x- and y-axes increment by 2.5%). Once the entire space of PC1% values and $R^2$ values has been tiled, the group of collapsed, at most, 1000 linear regression models can be compared via a group statistic, e.g., cross-validation statistic, of interest.

Of note, when the up to 1000 models were collapsed, the predicted amounts of released dopamine were averaged. The predicted amounts of released dopamine need not, strictly speaking, be averaged, but may be subject to a different form of central tendency, such as a median. The median predicted amount of released dopamine could be more robust to any outliers present in data in the cell lots, than the mean.

FIGS. 18A-H shows the results of grouping, at most, 1000 linear regression models, based on their PC1% and $R^2$ values. Each plot in FIGS. 18A-H is heat-mapped, with respect to a group statistic of interest, where the x-axis is the PC1% and the y-axis is the $R^2$ of the linear regression model, i.e., each plot in FIGS. 18A-H depicts the grid of PC1% by $R^2$ space, described above. That is, FIGS. 18A-H heat-maps, in corresponding order, the $R^2$, AUC, sensitivity, specificity, precision, F1, accuracy, and kappa values of the grouped models. In FIGS. 18A-H, the black-outlined circle in each plot indicates the model (collapsed from the group of models with similar PC1% and $R^2$ values) with the highest AUC and highest accuracy. The present example ranked the best groups of up to 1000 linear regression models, to be the groups of models ranked first by the highest accuracy, and then ranked by the highest AUC.

Figure 19:
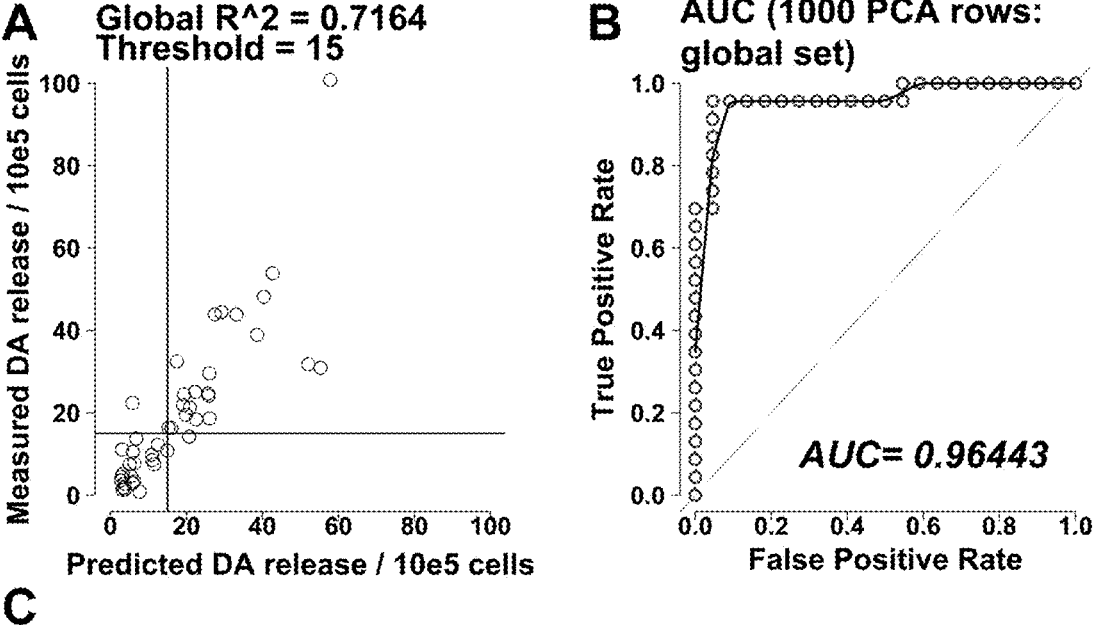
FIG. 19 depicts a non-limiting example of data that depicts the predictive performance of a linear regression model derived from PCA, that is predictive of amounts of dopamine released by neuronal cells derived from a population of neuronal progenitor cells after the neuronal progenitor cells are implanted into a subject brain, based on gene expression levels in the neuronal progenitor cells.

FIGS. 19A-C shows the predictive characteristics of a group of linear regression models. FIG. 19A depicts, for the (collapsed) model with, first, the highest AUC and, second, the highest accuracy, the relationship between predicted amount of released dopamine, according to an arbitrary scale normalized from 0 to 1 arbitrary units, and measured amount of released dopamine, also according to an arbitrary scale normalized from 0 to 1 arbitrary units. FIG. 19B depicts for the model with the highest AUC and highest accuracy, the receiver operator characteristic curve (ROC curve), and its corresponding AUC. FIG. 19C depicts a legend comprising various summary statistics associated with the model with the highest AUC and highest accuracy.

A desired number of highest ranking groups of the up to 1000 linear regression models can be selected according to any desired criteria, such that a desired number of unique genes from those groups of models' corresponding 5-gene sets can be identified.

Example 4—Non-PCA-Based Model for Predicting Dopamine Release Quantities

A machine learning method for predicting the amount of released dopamine from cultured DANPCs, upon the addition of potassium chloride (KCl), based on gene expression levels of DANPCs, was developed. To do so, bulk gene expression levels from a fraction of cells of a population of human DANPCs differentiated from in vitro pluripotent stem cells (iPSCs) were ascertained. A remaining fraction of cells from the same population of human DANPCs were cultured in vitro for approximately 60 days. KCl was then added to the DANPCs, to stimulate the release of dopamine (as well as serotonin). The amount of released dopamine (and serotonin) from the cultured DANPCs was obtained by liquid chromatography-mass spectrometry (LC-MS). Thus, from a given population of human DANPCs, population-specific bulk gene expression levels and a population-specific amount of released dopamine was obtained. Population-specific bulk gene expression levels and population-specific amounts of released dopamine were obtained for DANPC populations deriving from multiple human subjects. The PCA-based model described in the present example used DANPC gene expression levels to predict the amount of dopamine released by the cultured DANPCs. FIG. 11 depicts a schematic workflow of the non-PCA-based model for using bulk gene expression data from DANPCs to predict graft size, but the same general workflow can be applied to predicting the amount of dopamine released from cultured DANPCs. Of note, the methods described herein need not be limited to predicting the amount of dopamine released by DANPCs, but can generalize to a) predicting the amount of any released biological compound, e.g., neurotransmitter, such as dopamine or serotonin, provided that the relevant training data is used, and; b) other cell types that are not DANPCs.

The training data and test data used for training and testing the machine learning model included bulk RNA sequencing (RNAseq) data of the DANPCs. The bulk gene expression levels were then modeled against the amount of released dopamine of the corresponding DANPCs, via the edgeR software package in the R programming language. The edgeR software package modeled the relationship between individual gene expression and the response variable, amount of released dopamine, with an overdispersed Poisson model, such that each gene received its own estimate from a generalized linear model likelihood ratio test. Based on the overdispersed Poisson model, the top 1000 genes associated with the amount of released dopamine was identified, for a given training fraction.

A. Splitting the Data, by Donor, into Training and Test Fractions

The resulting data regarding the associations between the bulk RNAseq data and the corresponding DANPCs' amounts of released dopamine were split into a training data fraction and a test data fraction, via a leave-one-out (LOO) methodology, for the same number of iterations as the number of donors represented in the edgeR-modelled data, e.g., 8 iterations. The LOO method is a type of cross-validation method. The purpose of cross-validation is to control for the undesirable possibility that the training data fraction may not be representative of the variable of interest for prediction, and thus, the model fails to generalize, because the model is trained on unusual data. The training data fraction may, by random chance, comprise a highly unusual composition of data, and training a model based on such an unusual composition may result in a model that does not generalize across all or most instances of the variable of interest for prediction. To limit such artifacts, cross-validation is used. Cross-validation entails generating many pairs of training and test data fractions. In the case of LOO cross-validation, a single data point is reserved as the test data, and the remaining data is considered the training data. In the present example, DANPCs derived from 8 subjects, and thus 8 iterations of LOO were used for cross-validation: 1 subject (e.g., subject A) for test data and the remaining 7 subjects (subjects B-H) for training data; 1 subject (e.g., subject B) for test data and the remaining 7 subjects (subjects A, C-H) for training data . . . 1 subject (e.g., subject H) for test data and the remaining 7 subjects (subjects A-G) for training data. LOO cross-validation is useful in the case where the sample size of independent and individually distributed (IID) random variables is small. The present example considers the relevant sample size to be the number of subjects, unlike many other methods which consider the relevant sample size to be the number of cultured cells or cell lots, e.g., DANPCs. Although using the number of subjects as the relevant sample size will often result in a smaller sample size than if the number of cells were used, opting for the number of subjects as the relevant sample size during cross-validation can result in a machine learning model with improved predictive power. Some methods, however, opt to use the number of cells as the sample size, because doing so often inflates the sample size, and the experimenter may believe that a higher sample size is unconditionally favorable. Methods that use the number of cells or cell lots as the relevant sample size, however, can often lead to a machine learning model with poor predictive power, because in cases where the cultured cells or cell lots derive from common donors, the cells that derive from a common donor are not truly IID-cells from a common donor likely have much more in common than if they were compared to cells from another donor. In addition, by considering the relevant sample size to be the number of subjects, rather than the number of cultured cells, splitting of the data into training and test fractions during cross-validation does not result in cells from a given donor to be present in both the training and test fractions. Such a model design choice is especially important when using RNAseq data from donor cells because most of the unique signatures in donor cell RNAseq data is indicative of the idiosyncrasies of the donor subject, rather than being indicative of a more general variable of interest common to most donors, such as the amount of released neurotransmitter, e.g., the amount of released dopamine. For the reasons above, the methods described in the present example opt to use the number of subjects, and not the number of cultured cells or cell lots, as the relevant sample size for cross-validation, even though doing so may result in a smaller number of iterations for cross-validation. Accordingly, the cross-validation method used in the present example is limited to a cross-validation method that is compatible with a small sample size, and thus, LOO is used.

B. Computing on 3 Randomly Sampled Genes

Based on the edgeR-based modeled gene expression data and their associations with amounts of released dopamine, the top 1000 genes associated with the amounts of released dopamine was identified, for each of the 8 training fractions. The intersecting genes across each of the 8 training fractions was then identified. In addition to the genes being intersecting, each gene needed to possess at least 40 reads mapped to the gene, in at least 6 of the training fraction RNAseq libraries. 173 intersecting genes were identified, based on these criteria. The 173 genes were then further filtered using the 40 reads mapped to a given gene in at least 6 of the training fraction RNAseq libraries, such that only the more highly expressed genes remained. After filtering for the highly expressed genes, 140 genes remained. FIG. 11 depicts a schematic workflow of the non-PCA-based model for using bulk gene expression data from DANPCs to predict amounts of released dopamine.

From the remaining 140 genes, 3 genes were randomly sampled. The total number of possible combinations of 3 genes drawn from 140 possible genes is $$\binom{140}{3} = 447580$$

possible combinations. To achieve greater computational efficiency, sets of 3 genes were randomly sampled only 20000 times from the 447580 possibilities, and thus, approximately a two order of magnitude efficiency in computation was gained. In addition, the selection of using very few genes, e.g., 3 genes, from the total number of possible 140 genes, controls the otherwise outsized influence that a particular donor subject would have when generating one or more models for predicting the amounts of released dopamine. If a large number of genes was selected from the total number of possible 140 genes, most of the predictive power informed by the gene expression data would relate not to general amounts of released dopamine, i.e., amounts of released dopamine common or agnostic to the donor subjects, but rather, would relate mostly to the idiosyncrasies of the particular donor subject. Thus, to avoid generating a model that is based on overfitting the training data, only a small number of genes, e.g., 3 genes, were repeatedly selected from the 140 possible genes.

C. Generating Linear Regression Models from Gene Expression and Known Amounts of Released Dopamine To generate a model predictive of graft size for each of the randomly sampled 3 gene combinations, the gene expression levels of each of the 3 genes were linearly regressed against the graft sizes of the 45 cell lots, to generate a linear regression model of the form y=mx+b. Recall that the dataset analyzed in the present example comprises 45 cell lots deriving from 7 donor subjects, where each cell lot has corresponding bulk RNAseq data, which includes expression data for the top 140 genes. Thus, each linear regression model was derived from a sample size of 45 cell lots, where the predictor variable was the bulk gene expression of one of the three randomly selected genes, for a given cell lot, and the response variable was the amount of released dopamine for a given cell lot.

Figure 20:
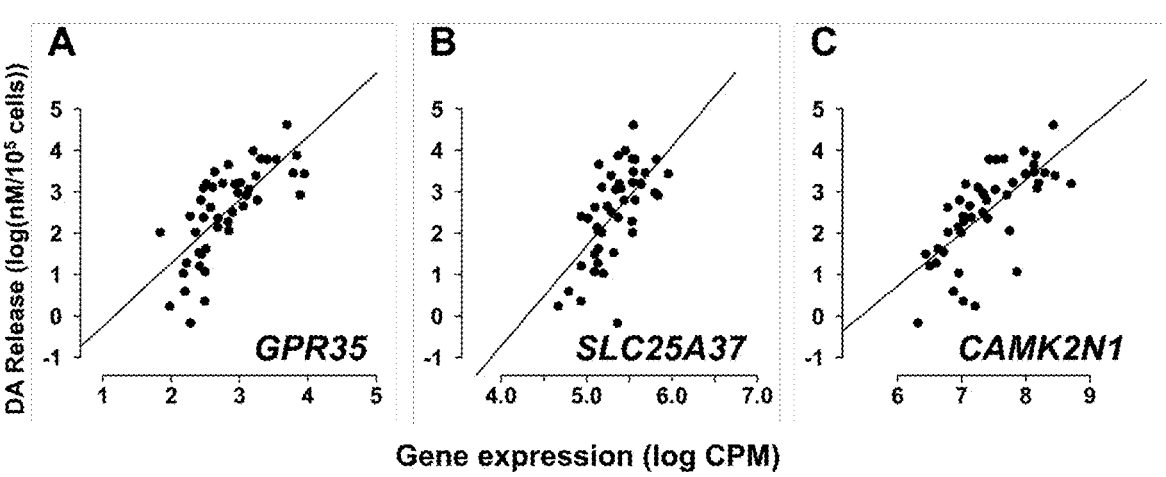
FIGS. 20A-C depict a non-limiting example of data for a set of linear regressions for a linear regression model derived without using PCA, to predict amounts of dopamine released by neuronal cells derived from a population of neuronal progenitor cells after the neuronal progenitor cells are implanted into a subject brain, based on gene expression levels in the neuronal progenitor cells.
Figure 21:
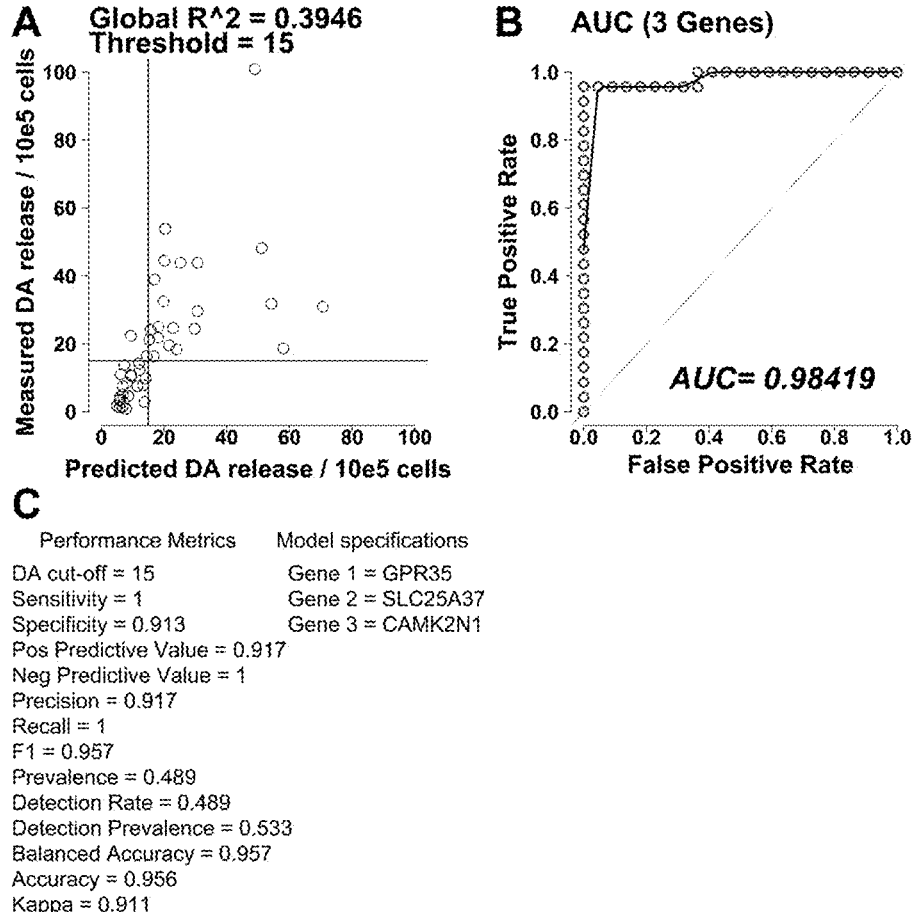
FIG. 21 depicts a non-limiting example of data that depicts the predictive performance of a linear regression model derived without using PCA, that is predictive of amounts of dopamine released by neuronal cells derived from a population of neuronal progenitor cells after the neuronal progenitor cells are implanted into a subject brain, based on gene expression levels in the neuronal progenitor cells.

FIGS. 20A-C depict linear regression models for each of three randomly selected genes from the list of 140 genes. The x-axis of each plot in FIGS. 20A-C is the gene expression of the one of the three randomly selected genes (in this case, GPR35 (FIG. 20A), SLC25A37 (FIG. 20B), and CAMK2N1 (FIG. 20C)), and the y-axis of each of the plots is the amount of released dopamine of the cell lot. Each datapoint on each of the plots corresponds to one of the 45 cell lots. To emphasize, each linear regression model in the present example is based on data from the training fraction. The linear regression models can then be used to predict amounts of released dopamine, based on gene expression data from the test fraction. For each set of three linear regression models corresponding to the set of three randomly selected genes, the three predicted amounts of released dopamine were averaged, to generate a single predicted amount of released dopamine. Of note, the averaging can be replaced with some other kind of central tendency calculation, such as the median, which can tend to be more robust than the mean, to outliers. Each set of three linear regression models were collapsed together, and for the collapsed model, a single accuracy, a single AUC and other single cross-validation summary statistics were determined. FIG. 21A depicts the relationship between the measured and the predicted amounts of released dopamine, for the model with the highest $R^2$ value, and FIG. 21B depicts the receiver-operating characteristic (ROC) curve, as well as its associated AUC value, for the 3-gene model based on GPR35, SLC25A37, and CAMK2N1, as shown in FIG. 20A-C, respectively. FIG. 21C is a legend that depicts a number of summary statistics associated with the collapsed model, including the AUC. The best collapsed linear regression models were ranked according to decreasing accuracy. Given that each set of three linear regression models corresponded to three randomly selected genes from a list of 62 genes, the most accurate models corresponded to a list of genes that informed those most accurate models. Further analysis, such as the application of a threshold cutoff can further curate the list of informative genes, to identify some number of genes of interest, to be used for e.g., biomedical or clinical applications.

The number of genes of interest can be based on a threshold cutoff such as a model accuracy of 0.8. The 20000 models based on random selections of 3 genes from the 140 possible genes were filtered, such that only models with an accuracy of greater than 0.8 were selected. 1406 models remained, after selection. All genes that appeared in the 1406 models were counted and ranked, according to frequency. The top 50 genes, for which their corresponding amounts of dopamine release were at least 15 nM/$10^5$, that were associated with the ranked 1406 models, were then identified. The expression levels of the top 50 genes were then quantified, by normalizing the counts per million (CPM) for a gene of interest, normalized by the CPM for a reference gene, such as the house-keeping gene, GAPDH. The expression levels were also alternatively quantified, by taking the base 2 logarithm of the CPM for a gene of interest, normalized by the base 2 logarithm of the CPM for a reference gene, such as the house-keeping gene, GAPDH. The results of the top 50 identified genes are listed in Table E2.

TABLE E2

Top 50 genes and their conditional ratio value associated with DA release ≥ 15 nM/$10^5$ cells.

| Gene ID | Greater DA release is consistent with $\log_2$CPM Gene/ $\log_2$CPM GAPDH | CPM Gene$_x$/ CPM GAPDH | Log$_2$CPM Gene/log$_2$CPM GAPDH |
|---|---|---|---|
| CNTNAP5 | less than | 0.001491 | 0.100905821 |
| KLHL1 | less than | 0.001331 | 0.085692193 |
| NHLH2 | less than | 0.020257 | 0.4642698 |
| GREM2 | less than | 0.005797 | 0.294782572 |
| BRINP2 | less than | 0.001065 | 0.080488828 |
| GRIN3A | less than | 0.013229 | 0.40007906 |
| LRRC4C | less than | 0.008257 | 0.328014189 |
| IRX3 | less than | 0.019857 | 0.45628914 |
| CPNE4 | less than | 0.003609 | 0.23043853 |

TABLE E2-continued

Top 50 genes and their conditional ratio value associated with DA release ≥ 15 nM/$10^5$ cells.

| Gene ID | Greater DA release is consistent with $\log_2$CPM Gene/ $\log_2$CPM GAPDH | CPM Gene$_x$/ CPM GAPDH | Log$_2$CPM Gene/log$_2$CPM GAPDH |
|---|---|---|---|
| PTPN3 | less than | 0.003327 | 0.209960378 |
| PMEL | less than | 0.004046 | 0.236757224 |
| PCDH20 | less than | 0.00283 | 0.164957081 |
| LRRC37A2 | less than | 0.054044 | 0.569251562 |
| TMEM246 | less than | 0.017462 | 0.43848835 |
| B3GALNT1 | less than | 0.048083 | 0.556054525 |
| ZHX1 | less than | 0.024385 | 0.456895083 |
| BCAS4 | greater than | 0.033794 | 0.533987707 |
| SLC25A37 | greater than | 0.022632 | 0.484783141 |
| GRINA | greater than | 0.153681 | 0.749693971 |
| MID1 | greater than | 0.188371 | 0.776893226 |
| FRMD4A | greater than | 0.118254 | 0.714678383 |
| PARP10 | greater than | 0.009583 | 0.322086665 |
| WHAMMP2 | greater than | 0.019194 | 0.471860731 |
| EYA1 | greater than | 0.012537 | 0.404615415 |
| CORO2B | greater than | 0.025742 | 0.511026833 |
| WHAMMP3 | greater than | 0.014248 | 0.432114078 |
| B3GALT5 | greater than | 0.023324 | 0.49786569 |
| GPR35 | greater than | 0.004122 | 0.238545889 |
| ABCD2 | greater than | 0.015128 | 0.440002167 |
| ITIH3 | greater than | 0.003368 | 0.222940099 |
| AC107464.1 | greater than | 0.006106 | 0.255492459 |
| CAMK2N1 | greater than | 0.075336 | 0.65443566 |
| CAMK2A | greater than | 0.021588 | 0.467859239 |
| PRPS1 | greater than | 0.086244 | 0.659894809 |
| GOLGA6L10 | greater than | 0.005299 | 0.265698268 |
| AMOT | greater than | 0.065592 | 0.629405322 |
| SULT1A1 | greater than | 0.003628 | 0.230545297 |
| CD83 | greater than | 0.011434 | 0.362165438 |
| SPON1 | greater than | 0.706997 | 0.953657503 |
| FRMPD3 | greater than | 0.013355 | 0.394252128 |
| AC096570.1 | greater than | 0.00016 | −0.17710749 |
| TCAF2 | greater than | 0.010164 | 0.376176492 |
| GOLGA8M | greater than | 0.000719 | 0.004207928 |
| VWA5B2 | greater than | 0.005706 | 0.280708507 |
| CA8 | greater than | 0.004126 | 0.239438832 |
| AC017050.1 | greater than | 0.001491 | 0.100905821 |
| KRT77 | greater than | 0.002609 | 0.176722518 |
| AP000350.6 | greater than | 0 | −0.39488338 |
| LINC02751 | greater than | 7.99E−05 | −0.24449344 |
| ARHGAP5-AS1 | greater than | 0.006586 | 0.325083905 |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of preparing a population of neuronal progenitor cells (NPCs) for treating a neurodegenerative disease, the method comprising predicting whether neuronal cells derived from a population of NPCs will produce dopamine by:

a) culturing pluripotent stem cells under conditions to neurally differentiate the pluripotent stem cells to obtain a population of NPCs;

b) determining a gene expression level for one or more gene associated with predicted dopamine production (D genes) in a test sample that comprises an aliquot of the population of NPCs, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1;

c) determining a predicted dopamine production capability of neuronal cells derived from the NPCs by comparing the gene expression level for one or more of the D genes in the test sample of NPCs to gene expression levels for the one or more D genes in a reference population of NPCs;

wherein the D gene is selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1 and ZHX1, and wherein the NPCs in the test sample are predicted to differentiate into neuronal cells that have a high dopamine production capability if the expression level of the D gene in the test sample of NPCs is lower than an empirically determined threshold or range; or wherein the D gene is selected from the group consisting of BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1, and wherein the NPCs in the test sample are predicted to differentiate into neuronal cells that have a high dopamine production capability if the expression level of the D gene in the test sample of NPCs is higher than the empirically derived threshold or range; and d) formulating NPCs having the predicted high dopamine production capability into a pharmaceutical composition.

2. The method of claim 1, wherein the empirically determined threshold or range is determined using a plurality of reference populations of NPCs, wherein for each reference population:

a) the gene expression level of the D gene is determined in an aliquot of each of the plurality of reference populations;

b) NPCs from the aliquot of the reference sample are differentiated into neuronal cells and the amount of dopamine produced by the neuronal cells is measured; and c) the measured dopamine production by the neuronal cells is statistically correlated with the expression level of the D gene in the NPCs of the reference population.

3. The method of claim 2, wherein the empirically determined threshold or range is obtained by performing differential expression analysis or linear regression analysis on the statistically correlated D gene expression levels and measured amount of dopamine production obtained for each of the plurality of reference populations.

4. The method of claim 1, wherein the determining a predicted dopamine capability comprises inputting gene expression levels for one or more of the D genes in NPCs of the test sample into a machine learning model trained to predict dopamine production capability of neuronal cells derived from a population of NPCs, wherein the machine learning model is trained using gene expression levels of the D genes in a plurality of reference populations of neuronal progenitor cells and corresponding measured dopamine production by neuronal cells derived from said reference populations, and wherein the machine learning model outputs the predicted dopamine production capability for neuronal cells derived from the test sample of NPCs based on the input D gene expression levels from the test sample.

5. The method of claim 4, wherein the machine learning model comprises principal component analysis.

6. The method of claim 1, wherein the predicted high dopamine production capability is at least 15 nM dopamine per $10^5$ neuronal cells.

7. The method of claim 1, wherein a composite predicted dopamine production capability score for the population of neuronal progenitor cells is determined by (a) determining a first predicted dopamine production capability by comparing the gene expression level in the test sample of a first D gene to the gene expression level for the first D gene in a reference population of NPCs; (b) determining at least a second predicted dopamine production capability by comparing the gene expression level in the test sample for at least a second D gene to a gene expression level for the second D gene in a reference population of NPCs; and (c) calculating a composite predicted dopamine production capability score for the NPCs in the test sample based on a statistical combination of the predicted dopamine production capabilities obtained for each of the two or more D genes.

8. The method of claim 7, wherein the statistical combination comprises determining a mean or median predicted dopamine production capability.

9. The method of claim 1, wherein the one or more D genes are selected from the group consisting of CNTNAP5, NHLH2, GREM2, PMEL, PCDH20, LRRC37A2, SLC25A37, MID1, EYA1, B3GALT5, GPR35, AC107464.1, CAMK2N1, CAMK2A, GOLGA6L10, FRMPD3, VWA5B2, AC017050.1, and LINC02751.

10. The method of claim 9, wherein the one or more D genes are selected from the group consisting of B3GALT5, FRMPD3 and GREM2.

11. The method of claim 10, wherein the one or more D genes are B3GALT5, FRMPD3 and GREM2.

12. The method of claim 1, wherein the gene expression level of each of the at least one D gene is determined by RNA sequencing (RNAseq).

13. The method of claim 1, wherein the gene expression level of each of the at least one D gene is determined by polymerase chain reaction (PCR).

14. The method of claim 13, wherein the PCR is quantitative PCR (qPCR).

15. The method of claim 14, wherein the gene expression level of the at least one D gene is determined by:

a) obtaining an RNA sample from the test sample of neuronal progenitor cells;

b) synthesizing complementary DNA from the RNA sample using reverse transcription;

c) amplifying a specific nucleic acid fragment corresponding to the D gene using quantitative polymerase chain reaction (qPCR), wherein the qPCR comprises the use of a pair of primers specific to the D gene, and optionally a probe specific to the D gene; and d) determining the expression level of the D gene based on the normalized quantified amount.

16. The method of claim 1, wherein the gene expression level of the one or more D genes is normalized as a ratio of the relative expression level of the D gene to a housekeeping gene, optionally wherein the housekeeping gene is GAPDH.

17. The method of claim 1, wherein the expression levels are determined for at least 2, 3, 4, 5, 6, 7, 8, 9, 10, 11, 12, 13, 14, 15, 16, 17, 18, 19 or 20 of the D genes.

18. The method of claim 1, wherein the reference population comprises a pooled sample of neuronal progenitor cells derived from multiple donors.

19. A method of preparing a pharmaceutical composition for treating a neurodegenerative disease, wherein the method comprises:

a) culturing pluripotent stem cells under conditions to neurally differentiate the pluripotent stem cells to obtain a population of neuronal progenitor cells (NPCs);

b) determining a gene expression level for one or more gene associated with predicted dopamine production (D genes) in a test sample that comprises an aliquot of the population of NPCs, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1;

c) determining a predicted dopamine production capability of neuronal cells derived from the NPCs by comparing the gene expression level for one or more of the D genes in the test sample of NPCs to gene expression levels for the one or more D genes in a reference population of NPCs;

wherein the D gene is selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1 and ZHX1, and wherein the NPCs in the test sample are predicted to differentiate into neuronal cells that have a high dopamine production capability if the expression level of the D gene in the test sample of NPCs is lower than an empirically determined threshold or range; or wherein the D gene is selected from the group consisting of BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1, and wherein the NPCs in the test sample are predicted to differentiate into neuronal cells that have a high dopamine production capability if the expression level of the D gene in the test sample of NPCs is higher than the empirically derived threshold or range; and d) formulating NPCs having the predicted high dopamine production capability into a pharmaceutical composition.

20. The method of claim 19, wherein the predicted high dopamine production capability is equal to or greater than 15 nM dopamine per $10^5$ cells.

21. The method of claim 19, wherein the pharmaceutical composition comprises a cryoprotectant.

22. A method for treating a subject having a neurodegenerative disease, the method comprising administering to a subject having a neurodegenerative disease a pharmaceutical composition that comprises neuronal progenitor cells (NPCs), wherein the pharmaceutical composition is prepared by a method that comprises:

a) culturing pluripotent stem cells under conditions to neurally differentiate the pluripotent stem cells to obtain a population of NPCs;

b) determining a gene expression level for one or more gene associated with predicted dopamine production (D genes) in a test sample that comprises an aliquot of the population of NPCs, wherein the D genes are selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1, ZHX1, BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1;

c) determining a predicted dopamine production capability of neuronal cells derived from the NPCs by comparing the gene expression level for one or more of the D genes in the test sample of NPCs to gene expression levels for the one or more D genes in a reference population of NPCs;

wherein the D gene is selected from the group consisting of CNTNAP5, KLHL1, NHLH2, GREM2, BRINP2, GRIN3A, LRRC4C, IRX3, CPNE4, PTPN3, PMEL, PCDH20, LRRC37A2, TMEM246, B3GALNT1 and ZHX1, and wherein the NPCs in the test sample are predicted to differentiate into neuronal cells that have a high dopamine production capability if the expression level of the D gene in the test sample of NPCs is lower than an empirically determined threshold or range; or wherein the D gene is selected from the group consisting of BCAS4, SLC25A37, GRINA, MID1, FRMD4A, PARP10, WHAMMP2, EYA1, CORO2B, WHAMMP3, B3GALT5, GPR35, ABCD2, ITIH3, AC107464.1, CAMK2N1, CAMK2A, PRPS1, GOLGA6L10, AMOT, SULT1A1, CD83, SPON1, FRMPD3, AC096570.1, TCAF2, GOLGA8M, VWA5B2, CA8, AC017050.1, KRT77, AP000350.6, LINC02751, and ARHGAP5-AS1, and wherein the NPCs in the test sample are predicted to differentiate into neuronal cells that have a high dopamine production capability if the expression level of the D gene in the test sample of NPCs is higher than the empirically derived threshold or range; and d) formulating NPCs having the predicted high dopamine production capability into a pharmaceutical composition.

* * * * *